(12) United States Patent
Kamps et al.

(10) Patent No.: US 8,795,650 B2
(45) Date of Patent: Aug. 5, 2014

(54) DERIVATION OF UNLIMITED QUANTITIES OF NEUTROPHILS OR MONOCYTE/DENDRITIC CELLS

(75) Inventors: Mark Kamps, Carlsbad, CA (US); David Sykes, Boston, MA (US)

(73) Assignee: The Regents of the University of California, Oakland, CA (US)

( * ) Notice: Subject to any disclaimer, the term of this patent is extended or adjusted under 35 U.S.C. 154(b) by 1640 days.

(21) Appl. No.: 11/792,988

(22) PCT Filed: Dec. 9, 2005

(86) PCT No.: PCT/US2005/044673
§ 371 (c)(1),
(2), (4) Date: Nov. 5, 2008

(87) PCT Pub. No.: WO2007/067183
PCT Pub. Date: Jun. 14, 2007

(65) Prior Publication Data
US 2009/0068157 A1 Mar. 12, 2009

Related U.S. Application Data

(60) Provisional application No. 60/635,264, filed on Dec. 9, 2004.

(51) Int. Cl.
*A01N 63/00* (2006.01)
*A01N 65/00* (2009.01)

(52) U.S. Cl.
USPC ........................ 424/93.21; 424/93.1; 424/93.2

(58) Field of Classification Search
USPC ..................................... 424/93.1, 93.2, 93.21
See application file for complete search history.

(56) References Cited

PUBLICATIONS

Perkins et al, (EMBO J, 12: 3835-3846, 1993).*
Luskey et al (Blood, 80(2): 396-402, 1992).*
Calvo et al., "Hoxa9 Immortalizes a Granulocyte-Macrophage Colony-Stimulating Factor-Dependent Promyelocyte Capable of Biphenotypic Differentiation to Neutrophils or Macrophages, Independent of Enforced Meis Expression", *Molecular and Cellular Biology*, 20(9):3274-3285, May 2000.
Calvo et al., "Nup98-HoxA9 immortalizes myeloid progenitors, enforces expression of Hoxa9, Hoxa7 and Meis1, and alters cytokine-specific responses in a manner similar to that induced by retroviral co-expression of Hoxa9 and Meis1", *Oncogene* 21:4247-4256, 2002.
Engelke et al., "Cells Transformed by a v-Myb-Estrogen Receptor Fusion Differentiate into Multinucleated Giant Cells", *Journal of Virology*, 71(5): 3760-3766, May 1997.
Knoepfler et al., "HoxB8 requires its Pbx-interaction motif to block differentiation of primary myeloid progenitors and of most cell line models of myeloid differentiation", *Oncogene* 20:5440-5448, 2001.
Shou et al., "Regulated expansion of hematopoietic progenitor cells by retroviral mediated transfer of a tamoxifen-inducible HOXB4-ERT2 fusion protein", *Blood*, 102(11):498b, Nov. 2003.
Sykes and Kamps, "Estrogen-regulated Conditional Oncoproteins: Tools to Address Open Questions in Normal Myeloid Cell Function, Normal Myeloid Differentiation, and the Genetic Basis of Differentiation Arrest in Myeloid Leukemia", *Leukemia & Lymphoma*, vol. 44(7):1131-1139, 2003.
Sykes and Kamps, "Estrogen-dependent E2a/Pbx1 myeloid cell lines exhibit conditional differentiation that can be arrested by other leukemic oncoproteins", *Blood* 98:2308-2318, 2001.

* cited by examiner

*Primary Examiner* — Marcia S Noble
*Assistant Examiner* — Magdalene Sgagias
(74) *Attorney, Agent, or Firm* — Sughrue Mion, PLLC

(57) ABSTRACT

A method to generate unlimited numbers of macrophage/dendritic cells or neutrophils from mice, using conditional Hox oncoproteins is disclosed. The invention further includes the establishment of a system to investigate immune responses to microorganisms or diseases involving chronic inflammation.

2 Claims, 8 Drawing Sheets

SEQUENCE LISTING

<160> NUMBER OF SEQ ID NOS: 17

<210> SEQ ID NO 1
<211> LENGTH: 2694
<212> TYPE: DNA
<213> ORGANISM: Mus musculus

<400> SEQUENCE: 1

```
aagctttaaa tatgactacc tcgttgtttg aaaatatgtt taggagagga agctgtatga      60
tctgataact tgtattaaaa taccaattac atttatagga ccttttaaaa ctcggtgcaa     120
ttaaaccgtg ttcttttaca tttttccgaa gcgaccctga catttagaaa gactccaatt     180
gcctcgttaa aatcgcgaaa ttaacagcgt gcctacgccc aggctcagcg ttgtggatgt     240
gtgtgtatgg tgttttccg tgactccccc acatcagtct ttgggggtgg tctgcgaagg      300
tatttgattt gttgtgaggc aagagatatc tcattaatgt aggtagttaa acagatttaa     360
tccgtattcg ttctctctct ctccccctc cctctcccc cctctccccc tctttctccc       420
tgggtgtttt tttctcttcc cctccttttt ttctgccctc tcctcactcc ctggcgctct     480
ctcgctctag ctctctctcg cactcgctct ctctcgctct caccctcgct ctgcgttctg     540
tccgggagag tacccagaag ccaataggat gcggggtctc taatggatgc aaatgatggt     600
gaaaagacgg ggcaaaatat gaaacaactc atttggaggg aagtaaatca ccgaaaactg     660
tttatgaact ggcatcccctt cttcgaaatg taaagcgagg acctctttaa gtggcggtat    720 attttttgttt ggggggtggg gggtgggggg agggcgagcg agccgcggct gccatgcagg    780
cttagacttt tgcaggcttc gctcttctat tcctggaaat cacaaaaagt gtggcggctt     840
tgagatcttc ttcgtctttt ctttcttttc cttccttcct tctttttttt ccctcctcc     900 cttttcctct cctttcctgg cgagggtgac taggagccgg cgaatccgcg ttttttttc     960 tctctctctc cctcccttt ccccctcccc accccctccc caacagcccc caactacagc      1020
ctgcgccgcc gccgccgccg cctcaaaatt caataaaatg agctcttatt tcgtcaactc     1080
actgttctcc aaatacaaaa ccggggagtc cctgcgcccc aattattatg actgcggctt    1140
cgcccaggac ctgggcggcc gacccaccgt ggtgtacggt cccagcagcg gcggcagctt    1200
ccagcaccct tcgcaaatcc aggagttcta ccacgggcca tcgtcgctgt ccacagctcc    1260
ctaccagcag aacccgtgcg ccgtggcgtg ccacggcgac cccggcaact tctacggcta    1320
cgaccctctg cagcgccaga gcctgttcgg tgcgcaggat ccagacctgg tgcagtacgc    1380
agactgcaag ctcgcggcag ccagcggcct gggcgaggag gccgaggggt ctgagcagag    1440
cccgtcgccc acacagctct ttccctggat gcgcccctcaa gcagccgccg gacgcaggcg    1500
aggccgccag acctacagtc gctaccagac cctggagctg gagaaggagt tcctatttaa    1560
tccctatctg actcgcaagc ggaggatcga ggtatcgcac gcgctgggac tgacagagag    1620
acaggtcaaa atctggttcc agaatcggag aatgaagtgg aaaaaggaga acaacaaaga    1680
caagtttccc agcagtaaat gcgagcagga ggagctggaa aaagagaagc tggagcgggc    1740
accagagacc gccgagcagg gcgatgcgca aagggtgac aagaagtagg ctccagctgg    1800
gactgctcgg gccggactag acccgcacgt ccgccggtcc ccccgcgac cacgccgccg    1860 ccgcccgccc cccgcctccg agagctcggc cccgcgagcg acgcaggagc tgggcctccc    1920
acagcagcgt cccccgccgc gccagtcccc gctagtggta gtatctcgta atagcttctg    1980
tgtgtgagct accgtggatc tccttccctt gcttctgtgt gtgagctacc gtggatctcc    2040
ttcccttctc ttgggggtcc gggggaaaa aagaaaagg attttaagca aggactctta     2100
agcaaggact ccctcgtcct gcgagggtga tcgactgcgg cctggcagaa cccctcgcc    2160 cccgcccat gtaaaaaagc ctccttgtgc aatggtctgt ttcctttgaa cgtgcttctt     2220
tgtaatgacc gaggtaccga ttttgctaa gttttcccaa caacatgaaa ctgcctattc     2280
acgccgtaat tctttctgtc tcccgctcac tttctctctt tctctcgctc tctttctctc    2340
```

```
accgcgtccc catctttcct cgcaacccccc tctccccgct gccctcccta gctggctttc    2400
tctcttgctt ctctcttttc ctcctctccc cccacccccca ccccctttgg tttgacaatt    2460
ttgtcttaag tgtttctcaa aagagattac tttagttagc atgcgcgctg tgagcattgt    2520
taaaaatgtt cttaggttta ctgtgaagag aatgtatcct gtatctgtga attgctttat    2580 ggggggagg  gagggctaat tatatatttt gttgttcctc tatactttgt tctgttgtct    2640
gcgcctgaaa agggcggaag agttacaata aagtttacaa gcagagaacc cgag          2694
```

<210> SEQ ID NO 2
<211> LENGTH: 243
<212> TYPE: PRT
<213> ORGANISM: Mus musculus

<400> SEQUENCE: 2

```
Met Ser Ser Tyr Phe Val Asn Ser Leu Phe Ser Lys Tyr Lys Thr Gly
1               5                   10                  15
Glu Ser Leu Arg Pro Asn Tyr Tyr Asp Cys Gly Phe Ala Gln Asp Leu
                20                  25                  30
Gly Gly Arg Pro Thr Val Val Tyr Gly Pro Ser Ser Gly Gly Ser Phe
            35                  40                  45
Gln His Pro Ser Gln Ile Gln Glu Phe Tyr His Gly Pro Ser Ser Leu
        50                  55                  60
Ser Thr Ala Pro Tyr Gln Gln Asn Pro Cys Ala Val Ala Cys His Gly
65                  70                  75                  80
Asp Pro Gly Asn Phe Tyr Gly Tyr Asp Pro Leu Gln Arg Gln Ser Leu
                85                  90                  95
Phe Gly Ala Gln Asp Pro Asp Leu Val Gln Tyr Ala Asp Cys Lys Leu
            100                 105                 110
Ala Ala Ala Ser Gly Leu Gly Glu Glu Ala Glu Gly Ser Glu Gln Ser
        115                 120                 125
Pro Ser Pro Thr Gln Leu Phe Pro Trp Met Arg Pro Gln Ala Ala Ala
    130                 135                 140
Gly Arg Arg Arg Gly Arg Gln Thr Tyr Ser Arg Tyr Gln Thr Leu Glu
145                 150                 155                 160
Leu Glu Lys Glu Phe Leu Phe Asn Pro Tyr Leu Thr Arg Lys Arg Arg
                165                 170                 175
Ile Glu Val Ser His Ala Leu Gly Leu Thr Glu Arg Gln Val Lys Ile
            180                 185                 190
Trp Phe Gln Asn Arg Arg Met Lys Trp Lys Lys Glu Asn Asn Lys Asp
        195                 200                 205
Lys Phe Pro Ser Ser Lys Cys Glu Gln Glu Glu Leu Glu Lys Glu Lys
    210                 215                 220
Leu Glu Arg Ala Pro Glu Thr Ala Glu Gln Gly Asp Ala Gln Lys Gly
225                 230                 235                 240
Asp Lys Lys
```

<210> SEQ ID NO 3
<211> LENGTH: 1839
<212> TYPE: DNA
<213> ORGANISM: Artificial sequence
<220> FEATURE:
<223> OTHER INFORMATION: Synthetic construct: fusion protein
<220> FEATURE:
<221> NAME/KEY: misc_feature
<222> LOCATION: (1774)..(1774)
<223> OTHER INFORMATION: n is a, c, g, or t
<220> FEATURE:

<221> NAME/KEY: misc_feature
<222> LOCATION: (1825)..(1826)
<223> OTHER INFORMATION: n is a, c, g, or t

<400> SEQUENCE: 3

```
gctctcttcc tcatccgccc cgtctctccc ccttgaacct cctcgttcga ccccgcctcg      60
atcctccctt tatccagccc tcactccttc tctaggcgcc ggaattcgcc accatgggat     120
acccatacga tgttccggat tacgctacgc gttctgctgg agacatgaga gctgccaacc     180
tttggccaag cccgctcatg atcaaacgct ctaagaagaa cagcctggcc ttgtccctga     240
cggccgacca gatggtcagt gccttgttgg atgctgagcc ccccatactc tattccgagt     300
atgatcctac cagaccccttc agtgaagctt cgatgatggg cttactgacc aacctggcag     360
acagggagct ggttcacatg atcaactggg cgaagagggt gccaggcttt gtggatttga     420
ccctccatga tcaggtccac cttctagaat gtgcctggct agagatcctg atgattggtc     480
tcgtctggcg ctccatggag cacccagtga agctactgtt tgctcctaac ttgctcttgg     540
acaggaacca gggaaaatgt gtagagggca tggtggagat cttcgacatg ctgctggcta     600
catcatctcg gttccgcatg atgaatctgc agggagagga gtttgtgtgc ctcaaatcta     660
ttatttgct taattctgga gtgtacacat ttctgtccag cacctgaag tctctggaag     720
agaaggacca tatccaccga gtcctggaca agatcacaga cactttgatc cacctgatgg     780
ccaaggcagg cctgaccctg cagcagcagc accagcggct ggcccagctc ctcctcatcc     840
tctcccacat caggcacatg agtaacaaag gcatggagca tctgtacagc atgaagtgca     900
agaacgtggt gccctctat gacctgctgc tggagatgct ggacgccac cgcctacatg     960
cgcccactag ccgtggaggg gcatccgtgg aggagacgga ccaaagccac ttggccactg    1020
cgggctctac ttcatcgcat tccttgcaaa agtattacat cacggggag gcagagggtt    1080
tccctgccac agtcacgcgt ggaagctctt atttcgtcaa ctcactgttc tccaaataca    1140
aaaccgggga gtccctgcgc cccaattatt atgactgcgg cttcgcccag gacctgggcg    1200
gccgacccac cgtggtgtac ggtcccagca gcggcggcag cttccagcac ccttcgcaaa    1260
tccaggagtt ctaccacggg ccatcgtcgc tgtccacagc tccctaccag cagaacccgt    1320
gcgccgtggc gtgccacggc gaccccggca acttctacgg ctacgaccct ctgcagcgcc    1380
agagcctgtt cggtgcgcag gatccagacc tggtgcagta cgcagactgc aagctcgcgg    1440
cagccagcgg cctgggcgag gaggccgagg gtctgagca gagcccgtcg cccacacagc    1500
tctttccctg gatgcgccct caagccgccg gacgcaggcg aggccgccag acctacagtc    1560
gctaccagac cctggagctg gagaaggagt tcctatttaa tccctatctg aatcgcaagc    1620
ggaggatcga ggtatcgcac gcgctgggac tgacagagag acaggtcaaa atctggttcc    1680
agaatcggag aatgaagtgg aaaaaggaga acaacaaaga caagtttccc agcagtaaat    1740
gcgagcagga ggagctggag aaagagaagc tggngcgggc accagagacc gccgagcagg    1800
gcgatgcgca gaagggtgac aagannngtag taactcgag                         1839
```

<210> SEQ ID NO 4
<211> LENGTH: 2271
<212> TYPE: DNA
<213> ORGANISM: Mus musculus

<400> SEQUENCE: 4

```
gaaaaaacag aagagggaag gataccagag cggttcatac agggcccaga aactaggcga      60
ggtgacccct cagcaagaca aacacctctt gatgttgact ggcgattttc cccatctcca     120
```

```
gtctggggag cgggactagg catacagatg atggagctta gaacccgctg gctagggaat    180
aaaattcgct gggcagtttg tgctcaaaga agtgggccag ggcgcttgtg acacaatcag    240
ggcgtttgtg acacaaaccc ttgagggttg gcagttctct ccttggcggt tgctctggtt    300
gctctgtggg gccttccctg tggagcaagg gtgatctggc cgatgtgcaa cgcctggct    360 ggctttccag tctgactagg gtcggtagcc cattttaggt ggttgtatca tcgacggtgc    420
gtcgcgacag gggcggtggt cactctgttt gaggtggaga gagccttgta tttgactttt    480
ctaggccggc cctgggggcg cgcgcgggcg gggggctcac atctctgagg actgcaagga    540
ttatttacag ggtattcacc aaccaaacac aacagtctaa tttaaccttt ccaagtcctc    600
ataaattttt acagggagcc acagcgaggc aaacgaatct gttggtcgct cctgactttc    660
caccagcctg tgtggcttcc gaaacaataa ctccttatga aatatcataa atatagattt    720
aaatacagta gagtgagaat gcgatttggc tgctttttta tggcttcaat tattgtctaa    780
ttttatgtga ggggctctgc tggccgtgct cacacgcggg acccgcgcct tcctgatggc    840
gtgattaatt gtgatataaa atagtccgct taagaagtgt gtgtgtctgg tatgtgtgtg    900
tgttgggggg gtggcaaggg agagtacaga ggcaaggcca gatttgatct tttaatcttc    960
gttggccaca attaaaacaa accagatcgt ggagctgcgc gatcccttg cataaaaaca    1020 tatgctttt gctataaaaa ttatgactgc aaaacaccgg gccattaata gcgtgcggag    1080
tgatttacgc gttattgttc tgccgggcgg acacgtgacg cgcgtggcca atggggcgc    1140 gggcgccggc aacttattag gtgactgtac ttcaccccc cctggtgcca ccaagttgtt    1200
acatgaaatc tgcagtttca taatttcggc gggtcgggct gggccggcca ggcgcgggct    1260
actgcaatgg ccaccaccgg ggccctgggc aactactatg tggactcctt cctgctgggc    1320
gccgacgctg ctgatgagct gggtgcggga cgctacgctc cagggaccct gggtcaaccc    1380
ccaaggcagg cggcagctct ggccgaacac cccgacttca gtccttgcag cttccagtcc    1440
aaggcggcgg tgtttggtgc ctcgtggaac ccagtgcacg cggcgggcgc caatgcggtg    1500
cctgctgcag tgtatcatca ccaccaccac ccctacgtgc atcccaggc gcccgtggcg    1560 gcggcggcgc cggacggcag gtatatgcgc tcctggctgg aacccacgcc cggtgcgctc    1620
tccttcgcgg gcttaccctc cagccggcct tatggcatta aacctgaacc gctctcggcc    1680
agaaggggtg actgtcccac gcttgacact cacactttgt ccctgactga ctatgcttgt    1740
ggttctcctc cagttgatag agaaaaacaa cccagcgaag gcgccttctc cgaaaacaat    1800
gccgagaatg agagcggcgg agacaagccc cccatcgatc ccaataaccc ggctgccaac    1860
tggctacatg ctcgctccac tcggaagaag cgatgccctt acacaaaaca ccagacgctg    1920
gaactggaga aggagtttct gtttaacatg tacctcacac gggaccgcag gtacgaggtg    1980
gcccggctgc tcaacctcac cgaaaggcag gtcaagatct ggttccagaa ccgcaggatg    2040
aaaatgaaga aaatcaacaa ggaccgagca aagacgagt gagccttta ggggctcatc    2100 taaaagaga gcaagctaga agaaaaaga aaggactgtc cgtctccctc tgtctcctct    2160
cccccaaacc cagcctccac ccgcacaaag gggctctaaa tcccaggcct catctcccca    2220
ctggcagtcc gtgctcaggc tggctcttag cgtgcggctt tgatggagga g            2271
```

<210> SEQ ID NO 5
<211> LENGTH: 271
<212> TYPE: PRT
<213> ORGANISM: Mus musculus

<400> SEQUENCE: 5

```
Met Ala Thr Thr Gly Ala Leu Gly Asn Tyr Tyr Val Asp Ser Phe Leu
1               5                   10                  15
Leu Gly Ala Asp Ala Ala Asp Glu Leu Gly Ala Gly Arg Tyr Ala Pro
            20                  25                  30
Gly Thr Leu Gly Gln Pro Pro Arg Gln Ala Ala Ala Leu Ala Glu His
        35                  40                  45
Pro Asp Phe Ser Pro Cys Ser Phe Gln Ser Lys Ala Ala Val Phe Gly
    50                  55                  60
Ala Ser Trp Asn Pro Val His Ala Ala Gly Ala Asn Ala Val Pro Ala
65                  70                  75                  80
Ala Val Tyr His His His His Pro Tyr Val His Pro Gln Ala Pro
                85                  90                  95
Val Ala Ala Ala Pro Asp Gly Arg Tyr Met Arg Ser Trp Leu Glu
            100                 105                 110
Pro Thr Pro Gly Ala Leu Ser Phe Ala Gly Leu Pro Ser Ser Arg Pro
        115                 120                 125
Tyr Gly Ile Lys Pro Glu Pro Leu Ser Ala Arg Arg Gly Asp Cys Pro
    130                 135                 140
Thr Leu Asp Thr His Thr Leu Ser Leu Thr Asp Tyr Ala Cys Gly Ser
145                 150                 155                 160
Pro Pro Val Asp Arg Glu Lys Gln Pro Ser Glu Gly Ala Phe Ser Glu
                165                 170                 175
Asn Asn Ala Glu Asn Glu Ser Gly Gly Asp Lys Pro Pro Ile Asp Pro
            180                 185                 190
Asn Asn Pro Ala Ala Asn Trp Leu His Ala Arg Ser Thr Arg Lys Lys
        195                 200                 205
Arg Cys Pro Tyr Thr Lys His Gln Thr Leu Glu Leu Glu Lys Glu Phe
    210                 215                 220
Leu Phe Asn Met Tyr Leu Thr Arg Asp Arg Arg Tyr Glu Val Ala Arg
225                 230                 235                 240
Leu Leu Asn Leu Thr Glu Arg Gln Val Lys Ile Trp Phe Gln Asn Arg
                245                 250                 255
Arg Met Lys Met Lys Lys Ile Asn Lys Asp Arg Ala Lys Asp Glu
            260                 265                 270
```

<210> SEQ ID NO 6
<211> LENGTH: 1804
<212> TYPE: DNA
<213> ORGANISM: Artificial sequence
<220> FEATURE:
<223> OTHER INFORMATION: Synthetic construct: fusion protein

<400> SEQUENCE: 6

```
gaattcacca tggaagaata tatgcctatg gaagcggcca ccacgcgttc tgctggagac      60
atgagagctg ccaacctttg gccaagcccg ctcatgatca aacgctctaa gaagaacagc    120
ctggccttgt ccctgacggc cgaccagatg gtcagtgcct tgttggatgc tgagcccccc    180
atactctatt ccgagtatga tcctaccaga cccttcagtg aagcttcgat gatgggctta    240
ctgaccaacc tggcagacag ggagctggtt cacatgatca ctgggcgaa gagggtgcca    300
ggctttgtgg atttgacccc tccatgatcag gtccaccttc tagaatgtgc ctggctagag    360
atcctgatga ttggtctcgt ctggcgctcc atggagcacc cagtgaagct actgtttgct    420
cctaacttgc tcttggacag gaaccaggga aaatgtgtag agggcatggt ggagatcttc    480
```

-continued

| | |
|---|---|
| gacatgctgc tggctacatc atctcggttc cgcatgatga atctgcaggg agaggagttt | 540 |
| gtgtgcctca aatctattat tttgcttaat tctggagtgt acacatttct gtccagcacc | 600 |
| ctgaagtctc tggaagagaa ggaccatatc caccgagtcc tggacaagat cacagacact | 660 |
| ttgatccacc tgatggccaa ggcaggcctg accctgcagc agcagcacca gcggctggcc | 720 |
| cagctcctcc tcatcctctc ccacatcagg cacatgagta acaaaggcat ggagcatctg | 780 |
| tacagcatga agtgcaagaa cgtggtgccc ctctatgacc tgctgctgga gatgctggac | 840 |
| gcccaccgcc tacatgcgcc cactagccgt ggaggggcat ccgtggagga cacggaccaa | 900 |
| agccacttgg ccactgcggg ctctacttca tcgcattcct tgcaaaagta ttacatcacg | 960 |
| ggggaggcag agggtttccc tgccacagtc acgcgtggcc ctgggcaact actatgtgga | 1020 |
| ctccttcctg ctgggcgccg acgctgctga tgagctgggt gcgggacgct acgtccagg | 1080 |
| gaccctgggt caaccccaa ggcaggcggc agctctggcc gaacaccccg acttcagtcc | 1140 |
| ttgcagcttc cagtccaagg cggcggtgtt tggtgcctcg tggaacccag tgcacgcggc | 1200 |
| gggcgccaat gcggtgcctg ctgcagtgta tcatcaccac caccacccct acgtgcatcc | 1260 |
| ccaggcgccc gtggcggcgg cggcgccgga cggcaggtat atgcgctcct ggctggaacc | 1320 |
| cacgcccggt gcgctctcct tcgcgggctt accctccagc cggccttatg gcattaaacc | 1380 |
| tgaaccgctc tcggccagaa ggggtgactg tcccacgctt gacactcaca ctttgtccct | 1440 |
| gactgactat gcttgtggtt ctcctccagt tgatagagaa aaacaaccca gcgaaggcgc | 1500 |
| cttctccgaa acaatgccg agaatgagag cggcggagac aagccccca tcgatcccaa | 1560 |
| taacccggct gccaactggc tacatgctcg ctccactcgg aagaagcgat gcccttacac | 1620 |
| aaaacaccag acgctggaac tggagaagga gtttctgttt aacatgtacc tcacacggga | 1680 |
| ccgcaggtac gaggtggccc ggctgctcaa cctcaccgaa aggcaggtca agatctggtt | 1740 |
| ccagaaccgc aggatgaaaa tgaagaaaat caacaaggac cgagcaaaag acgagtgaga | 1800 |
| attc | 1804 |

<210> SEQ ID NO 7
<211> LENGTH: 1950
<212> TYPE: DNA
<213> ORGANISM: Mus musculus

<400> SEQUENCE: 7

| | |
|---|---|
| agtgcttaga aaggtgaagc cgcgggatct gggtggcccc tagaaagggc tcccttattc | 60 |
| gcttttattg tctcctaaag aactgggggtt ccacaatgag ctacagcacc caggtcctga | 120 |
| gattacctct cctgtctcta atccagctct aaaactgtta ccggcccaca gggtggaagg | 180 |
| cttgcttgcc tgagagctgc caggagtgta tgacggatgt gttttaaaat ttgtggagcc | 240 |
| gagtttctcc caaactgaat gaggataccc cagttttgt catccagggg gtaactaggg | 300 |
| gttgtggcaa ggacaaagcg ggtgttgagc tatctctgga gttgctgcca gccagccagg | 360 |
| tgcccaggag caaatgcaga gaaactgcca gggccgcagt gtccggagag ccgggggaat | 420 |
| cccatggtag tatatctgat ggcaaatgag gctcattaat agataaatat ttcactgctt | 480 |
| cccctttaggg cagataaaca gtgcgccgcc gatttaaagt aggaagctga gagacgttga | 540 |
| ctttattcga accacatggt tccagtttgt ggcagcggtc tctccgctcg gctagaggag | 600 |
| acaccgcgcc tgcggtgttg acgctggatc accaaatcag gtcttaaagg tttccctgct | 660 |
| tatagagaga ggtgggcaaa gagtggattt ccctctctag accatctttg gcggacagg | 720 |
| ttacagagac cctgggtctt ggaccctcag agagggcccg aacaggggga atccacacag | 780 |

-continued

```
tggatctggg gttcaggaat aggtatgagg ttgtcggggg aggggcgag atccctgcct    840
ccaggcttcg gcggctggga cggggctctg gcggagccta gggtctgat tgcgtcgggc    900
gccctggcag cccggtgcag gcaggccgcg tctgtgagcc tcttcccctt ccattctagg    960
agccggcggc ccgtggcgcg ggaccacctg tgagggctgc tgagattggc ggagcgggtc   1020
atgtgggcgg tcacgtgccg cggcgagctc cgtccaaaag aaaatggggt ttggtgtaaa   1080
tctgggggtg taatgttatc atatatcacg ctacctcgta aaccgacac tgaaagctgc    1140
cggacaacaa atcacaggtc aaaattatga gttcttcgta ttatgtgaac gcgcttttta   1200
gcaaatatac ggcggggct tctctcttcc aaaatgccga ccgacttct tgctcctttg    1260
cacccaactc gcagagaagc ggctacgggc cgggcgccgg cgccttcgcc tccactgtgc   1320
cgggcttata caatgtcaac agccccctct atcagagccc cttcgcgtcc ggctatggcc   1380
tgggagccga cgcctacaac ctgccctgcg cctcctacga ccaaaacatc cccgggctct   1440
gcagtgacct cgccaaaggc gcctgcgaca aggcggacga gggcgtgctt cacggcccgg   1500
ccgaagccag tttccgcatc taccctgga tgcgcagttc aggacccgac aggaagcggg    1560
gacgccagac ctacacgcgc taccagacgc tggaactgga gaaggaattc catttcaacc   1620
gctacctgac gcggcgccgc cgcatcgaga tcgctcacgc gctctgcctc actgagcgcc   1680
agatcaagat ctggttccag aatcggcgca tgaagtggaa gaaagagcat aaagatgaga   1740
gccaggctcc cactgcagcc ccggaagacg cggtgccctc cgtttccaca gctgctgaca   1800
aggcggacga ggaggaagag gaggaagagg aggaagaaga ggaggaagag gagtaaaggg   1860
ccaggcacag gaccctggct gcacaggaca gttggaaaag cgtctttaag agactcattg   1920
attttagtta caaaaatggg gggaaataaa                                    1950
```

<210> SEQ ID NO 8
<211> LENGTH: 229
<212> TYPE: PRT
<213> ORGANISM: Mus musculus

<400> SEQUENCE: 8

```
Met Ser Ser Tyr Tyr Val Asn Ala Leu Phe Ser Lys Tyr Thr Ala
1               5                   10                  15

Gly Ala Ser Leu Phe Gln Asn Ala Glu Pro Thr Ser Cys Ser Phe Ala
                20                  25                  30

Pro Asn Ser Gln Arg Ser Gly Tyr Gly Pro Gly Ala Gly Phe Ala
            35                  40                  45

Ser Thr Val Pro Gly Leu Tyr Asn Val Asn Ser Pro Leu Tyr Gln Ser
    50                  55                  60

Pro Phe Ala Ser Gly Tyr Gly Leu Gly Ala Asp Ala Tyr Asn Leu Pro
65                  70                  75                  80

Cys Ala Ser Tyr Asp Gln Asn Ile Pro Gly Leu Cys Ser Asp Leu Ala
                85                  90                  95

Lys Gly Ala Cys Asp Lys Ala Asp Glu Gly Val Leu His Gly Pro Ala
            100                 105                 110

Glu Ala Ser Phe Arg Ile Tyr Pro Trp Met Arg Ser Ser Gly Pro Asp
        115                 120                 125

Arg Lys Arg Gly Arg Gln Thr Tyr Thr Arg Tyr Gln Thr Leu Glu Leu
    130                 135                 140

Glu Lys Glu Phe His Phe Asn Arg Tyr Leu Thr Arg Arg Arg Ile
145                 150                 155                 160
```

Glu Ile Ala His Ala Leu Cys Leu Thr Glu Arg Gln Ile Lys Ile Trp
            165                 170                 175

Phe Gln Asn Arg Arg Met Lys Trp Lys Lys Glu His Lys Asp Glu Ser
        180                 185                 190

Gln Ala Pro Thr Ala Ala Pro Glu Asp Ala Val Pro Ser Val Ser Thr
        195                 200                 205

Ala Ala Asp Lys Ala Asp Glu Glu Glu Glu Glu Glu Glu Glu Glu Glu
    210                 215                 220

Glu Glu Glu Glu Glu
225

<210> SEQ ID NO 9
<211> LENGTH: 1796
<212> TYPE: DNA
<213> ORGANISM: Artificial sequence
<220> FEATURE:
<223> OTHER INFORMATION: Synthetic construct: fusion protein

<400> SEQUENCE: 9
gctctcttcc tcatccgccc cgtctctccc ccttgaacct cctcgttcga ccccgcctcg      60
atcctccctt tatccagccc tcactccttc tctaggcgcc ggaattcgcc accatgggat     120
acccatacga tgttccggat tacgctacgc gtatgagttc ttcgtattat gtgaacgcgc     180 ttttatctg ctggagacat gagagctgcc aacctttggc caagcccgct catgatcaaa      240
cgctctaaga gaacagcct ggccttgtcc ctgacggccg accagatggt cagtgccttg       300
ttggatgctg agccccccat actctattcc gagtatgatc ctaccagacc cttcagtgaa     360
gcttcgatga tgggcttact gaccaacctg gcagacaggg agctggttca catgatcaac     420
tgggcgaaga gggtgccagg ctttgtggat ttgaccctcc atgatcaggt ccaccttcta     480
gaatgtgcct ggctagagat cctgatgatt ggtctcgtct ggcgctccat ggagcaccca     540
gtgaagctac tgtttgctcc taacttgctc ttggacagga accagggaaa atgtgtagag     600
ggcatggtgg agatcttcga catgctgctg gctacatcat ctcggttccg catgatgaat     660
ctgcagggag aggagtttgt gtgcctcaaa tctattattt tgcttaattc tggagtgtac     720
acatttctgt ccagcaccct gaagtctctg gaagagaagg accatatcca ccgagtcctg     780
gacaagatca gagacacttt gatccacctg atggccaagg caggcctgac cctgcagcag     840
cagcaccagc ggctggccca gctcctcctc atcctctccc acatcaggca catgagtaac     900
aaaggcatgg agcatctgta cagcatgaag tgcaagaacg tggtgcccct ctatgacctg     960
ctgctggaga tgctggacgc ccaccgccta catgcgccca ctagccgtgg aggggcatcc    1020
gtggaggaga cggaccaaag ccacttggcc actgcgggct ctacttcatc gcattccttg    1080
caaaagtatt acatcacggg ggaggcagag ggtttccctg ccacagtcac gcgtgcaaat    1140
atacggcggg ggcttctctc ttccaaaatg ccgagccgac ttcttgctcc tttgcaccca    1200
actcgcagag aagcggctac gggcggggcg ccggcgcctt cgcctccact gtgccgggct    1260
tatacaatgt caacagcccc ctctatcaga gcccccttcgc gtccggctat ggcctgggag    1320
ccgacgccta aacctgccc tgcgcctcct acgaccaaaa catccccggg ctctgcagtg      1380
acctcgccaa aggcgcctgc gacaaggcgg acgagggcgt gcttcacggc ccggccgaag    1440
ccagtttccg catctacccc tggatgcgca gttcaggacc cgacaggaag cggggacgcc    1500
agacctacac gcgctaccag acgctggaac tggagaagga attccatttc aaccgctacc    1560
tgacgcggcg ccgccgcatc gagatcgctc acgcgctctg cctcactgag cgccagatca    1620

```
agatctggtt ccagaatcgg cgcatgaagt ggaagaaaga gcataaagat gagagccagg      1680
ctcccactgc agccccggaa gacgcggtgc cctccgtttc cacagctgct gacaaggcgg      1740
acgaggagga agaggaggaa gaggaggaag aagaggagga agaggagtaa gaattc          1796
```

<210> SEQ ID NO 10
<211> LENGTH: 314
<212> TYPE: PRT
<213> ORGANISM: Homo sapiens

<400> SEQUENCE: 10

```
Ser Ala Gly Asp Met Arg Ala Ala Asn Leu Trp Pro Ser Pro Leu Met
1               5                   10                  15

Ile Lys Arg Ser Lys Lys Asn Ser Leu Ala Leu Ser Leu Thr Ala Asp
            20                  25                  30

Gln Met Val Ser Ala Leu Leu Asp Ala Glu Pro Pro Ile Leu Tyr Ser
        35                  40                  45

Glu Tyr Asp Pro Thr Arg Pro Phe Ser Glu Ala Ser Met Met Gly Leu
    50                  55                  60

Leu Thr Asn Leu Ala Asp Arg Glu Leu Val His Met Ile Asn Trp Ala
65                  70                  75                  80

Lys Arg Val Pro Gly Phe Val Asp Leu Thr Leu His Asp Gln Val His
                85                  90                  95

Leu Leu Glu Cys Ala Trp Leu Glu Ile Leu Met Ile Gly Leu Val Trp
            100                 105                 110

Arg Ser Met Glu His Pro Val Lys Leu Leu Phe Ala Pro Asn Leu Leu
        115                 120                 125

Leu Asp Arg Asn Gln Gly Lys Cys Val Glu Gly Met Val Glu Ile Phe
    130                 135                 140

Asp Met Leu Leu Ala Thr Ser Ser Arg Phe Arg Met Met Asn Leu Gln
145                 150                 155                 160

Gly Glu Glu Phe Val Cys Leu Lys Ser Ile Ile Leu Leu Asn Ser Gly
                165                 170                 175

Val Tyr Thr Phe Leu Ser Ser Thr Leu Lys Ser Leu Glu Glu Lys Asp
            180                 185                 190

His Ile His Arg Val Leu Asp Lys Ile Thr Asp Thr Leu Ile His Leu
        195                 200                 205

Met Ala Lys Ala Gly Leu Thr Leu Gln Gln Gln His Gln Arg Leu Ala
    210                 215                 220

Gln Leu Leu Leu Ile Leu Ser His Ile Arg His Met Ser Asn Lys Gly
225                 230                 235                 240

Met Glu His Leu Tyr Ser Met Lys Cys Lys Asn Val Val Pro Leu Tyr
                245                 250                 255

Asp Leu Leu Leu Glu Met Leu Asp Ala His Arg Leu His Ala Pro Thr
            260                 265                 270

Ser Arg Gly Gly Ala Ser Val Glu Glu Thr Asp Gln Ser His Leu Ala
        275                 280                 285

Thr Ala Gly Ser Thr Ser Ser His Ser Leu Gln Lys Tyr Tyr Ile Thr
    290                 295                 300

Gly Glu Ala Glu Gly Phe Pro Ala Thr Val
305                 310
```

<210> SEQ ID NO 11
<211> LENGTH: 74
<212> TYPE: DNA
<213> ORGANISM: Artificial sequence
<220> FEATURE:
<223> OTHER INFORMATION: Primer

<400> SEQUENCE: 11
ggaattcgcc accatggact acaaggacga cgatgacaaa ggaacgcgtg gaagctctta    60
tttcgtcaac tcac                                                     74

<210> SEQ ID NO 12
<211> LENGTH: 77
<212> TYPE: DNA
<213> ORGANISM: Artificial sequence
<220> FEATURE:
<223> OTHER INFORMATION: Primer

<400> SEQUENCE: 12
ggaattcgcc accatgggat acccatacga tgttccggat tacgctacgc gtggaagctc    60
ttatttcgtc aactcac                                                  77

<210> SEQ ID NO 13
<211> LENGTH: 35
<212> TYPE: DNA
<213> ORGANISM: Artificial sequence
<220> FEATURE:
<223> OTHER INFORMATION: Primer

<400> SEQUENCE: 13
ccgctcgagt tactacttct tgtcaccctt ctgcg                              35

<210> SEQ ID NO 14
<211> LENGTH: 9
<212> TYPE: PRT
<213> ORGANISM: Artificial sequence
<220> FEATURE:
<223> OTHER INFORMATION: Synthetic construct: FLAG peptide (epitope tag)

<400> SEQUENCE: 14

Asp Tyr Lys Asp Asp Asp Asp Lys Gly
1               5

<210> SEQ ID NO 15
<211> LENGTH: 9
<212> TYPE: PRT
<213> ORGANISM: Artificial sequence
<220> FEATURE:
<223> OTHER INFORMATION: Synthetic construct: Hemaglutinin peptide
      (epitope tag)

<400> SEQUENCE: 15

Tyr Pro Tyr Asp Val Pro Asp Tyr Ala
1               5

<210> SEQ ID NO 16
<211> LENGTH: 560
<212> TYPE: PRT
<213> ORGANISM: Artificial sequence
<220> FEATURE:
<223> OTHER INFORMATION: Synthetic construct: fusion protein

<400> SEQUENCE: 16

Tyr Pro Tyr Asp Val Pro Asp Tyr Ala Ser Ala Gly Asp Met Arg Ala
1               5                   10                  15

Ala Asn Leu Trp Pro Ser Pro Leu Met Ile Lys Arg Ser Lys Lys Asn
            20                  25                  30

Ser Leu Ala Leu Ser Leu Thr Ala Asp Gln Met Val Ser Ala Leu Leu

```
                35                  40                  45
Asp Ala Glu Pro Pro Ile Leu Tyr Ser Glu Tyr Asp Pro Thr Arg Pro
    50                  55                  60

Phe Ser Glu Ala Ser Met Met Gly Leu Leu Thr Asn Leu Ala Asp Arg
 65                  70                  75                  80

Glu Leu Val His Met Ile Asn Trp Ala Lys Arg Val Pro Gly Phe Val
                 85                  90                  95

Asp Leu Thr Leu His Asp Gln Val His Leu Glu Cys Ala Trp Leu
            100                 105                 110

Glu Ile Leu Met Ile Gly Leu Val Trp Arg Ser Met Glu His Pro Val
            115                 120                 125

Lys Leu Leu Phe Ala Pro Asn Leu Leu Leu Asp Arg Asn Gln Gly Lys
        130                 135                 140

Cys Val Glu Gly Met Val Glu Ile Phe Asp Met Leu Leu Ala Thr Ser
145                 150                 155                 160

Ser Arg Phe Arg Met Met Asn Leu Gln Gly Glu Glu Phe Val Cys Leu
                165                 170                 175

Lys Ser Ile Ile Leu Leu Asn Ser Gly Val Tyr Thr Phe Leu Ser Ser
            180                 185                 190

Thr Leu Lys Ser Leu Glu Glu Lys Asp His Ile His Arg Val Leu Asp
        195                 200                 205

Lys Ile Thr Asp Thr Leu Ile His Leu Met Ala Lys Ala Gly Leu Thr
    210                 215                 220

Leu Gln Gln Gln His Gln Arg Leu Ala Gln Leu Leu Leu Ile Leu Ser
225                 230                 235                 240

His Ile Arg His Met Ser Asn Lys Gly Met Glu His Leu Tyr Ser Met
                245                 250                 255

Lys Cys Lys Asn Val Val Pro Leu Tyr Asp Leu Leu Leu Glu Met Leu
            260                 265                 270

Asp Ala His Arg Leu His Ala Pro Thr Ser Arg Gly Gly Ala Ser Val
        275                 280                 285

Glu Glu Thr Asp Gln Ser His Leu Ala Thr Ala Gly Ser Thr Ser Ser
290                 295                 300

His Ser Leu Gln Lys Tyr Tyr Ile Thr Gly Glu Ala Glu Met Ser Ser
305                 310                 315                 320

Tyr Phe Val Asn Ser Leu Phe Ser Lys Tyr Lys Thr Gly Glu Ser Leu
                325                 330                 335

Arg Pro Asn Tyr Tyr Asp Cys Gly Phe Ala Gln Asp Leu Gly Gly Arg
            340                 345                 350

Pro Thr Val Val Tyr Gly Pro Ser Gly Gly Ser Phe Gln His Pro
        355                 360                 365

Ser Gln Ile Gln Glu Phe Tyr His Gly Pro Ser Ser Leu Ser Thr Ala
    370                 375                 380

Pro Tyr Gln Gln Asn Pro Cys Ala Val Ala Cys His Gly Asp Pro Gly
385                 390                 395                 400

Asn Phe Tyr Gly Tyr Asp Pro Leu Gln Arg Gln Ser Leu Phe Gly Ala
                405                 410                 415

Gln Asp Pro Asp Leu Val Gln Tyr Ala Asp Cys Lys Leu Ala Ala Ala
            420                 425                 430

Ser Gly Leu Gly Glu Glu Ala Glu Gly Ser Glu Gln Ser Pro Ser Pro
        435                 440                 445

Thr Gln Leu Phe Pro Trp Met Arg Pro Gln Ala Ala Ala Gly Arg Arg
    450                 455                 460
```

Arg Gly Arg Gln Thr Tyr Ser Arg Tyr Gln Thr Leu Glu Leu Glu Lys
465                 470                 475                 480

Glu Phe Leu Phe Asn Pro Tyr Leu Thr Arg Lys Arg Ile Glu Val
            485                 490                 495

Ser His Ala Leu Gly Leu Thr Glu Arg Gln Val Lys Ile Trp Phe Gln
                500                 505                 510

Asn Arg Arg Met Lys Trp Lys Lys Glu Asn Asn Lys Asp Lys Phe Pro
            515                 520                 525

Ser Ser Lys Cys Glu Gln Glu Leu Glu Lys Glu Lys Leu Glu Arg
530                 535                 540

Ala Pro Glu Thr Ala Glu Gln Gly Asp Ala Gln Lys Gly Asp Lys Lys
545                 550                 555                 560

<210> SEQ ID NO 17
<211> LENGTH: 588
<212> TYPE: PRT
<213> ORGANISM: Artificial sequence
<220> FEATURE:
<223> OTHER INFORMATION: Synthetic construct: fusion protein

<400> SEQUENCE: 17

Asp Tyr Lys Asp Asp Asp Asp Lys Gly Ser Ala Gly Asp Met Arg Ala
1               5                   10                  15

Ala Asn Leu Trp Pro Ser Pro Leu Met Ile Lys Arg Ser Lys Lys Asn
            20                  25                  30

Ser Leu Ala Leu Ser Leu Thr Ala Asp Gln Met Val Ser Ala Leu Leu
        35                  40                  45

Asp Ala Glu Pro Pro Ile Leu Tyr Ser Glu Tyr Asp Pro Thr Arg Pro
50                  55                  60

Phe Ser Glu Ala Ser Met Met Gly Leu Leu Thr Asn Leu Ala Asp Arg
65                  70                  75                  80

Glu Leu Val His Met Ile Asn Trp Ala Lys Arg Val Pro Gly Phe Val
                85                  90                  95

Asp Leu Thr Leu His Asp Gln Val His Leu Leu Glu Cys Ala Trp Leu
            100                 105                 110

Glu Ile Leu Met Ile Gly Leu Val Trp Arg Ser Met Glu His Pro Val
        115                 120                 125

Lys Leu Leu Phe Ala Pro Asn Leu Leu Leu Asp Arg Asn Gln Gly Lys
130                 135                 140

Cys Val Glu Gly Met Val Glu Ile Phe Asp Met Leu Leu Ala Thr Ser
145                 150                 155                 160

Ser Arg Phe Arg Met Met Asn Leu Gln Gly Glu Glu Phe Val Cys Leu
                165                 170                 175

Lys Ser Ile Ile Leu Leu Asn Ser Gly Val Tyr Thr Phe Leu Ser Ser
            180                 185                 190

Thr Leu Lys Ser Leu Glu Glu Lys Asp His Ile His Arg Val Leu Asp
        195                 200                 205

Lys Ile Thr Asp Thr Leu Ile His Leu Met Ala Lys Ala Gly Leu Thr
210                 215                 220

Leu Gln Gln Gln His Gln Arg Leu Ala Gln Leu Leu Leu Ile Leu Ser
225                 230                 235                 240

His Ile Arg His Met Ser Asn Lys Gly Met Glu His Leu Tyr Ser Met
                245                 250                 255

Lys Cys Lys Asn Val Val Pro Leu Tyr Asp Leu Leu Leu Glu Met Leu
            260                 265                 270

-continued

```
Asp Ala His Arg Leu His Ala Pro Thr Ser Arg Gly Gly Ala Ser Val
        275                 280                 285

Glu Glu Thr Asp Gln Ser His Leu Ala Thr Ala Gly Ser Thr Ser Ser
        290                 295                 300

His Ser Leu Gln Lys Tyr Tyr Ile Thr Gly Glu Ala Glu Met Ala Thr
305                 310                 315                 320

Thr Gly Ala Leu Gly Asn Tyr Tyr Val Asp Ser Phe Leu Leu Gly Ala
                325                 330                 335

Asp Ala Ala Asp Glu Leu Gly Ala Gly Arg Tyr Ala Pro Gly Thr Leu
                340                 345                 350

Gly Gln Pro Pro Arg Gln Ala Ala Leu Ala Glu His Pro Asp Phe
        355                 360                 365

Ser Pro Cys Ser Phe Gln Ser Lys Ala Ala Val Phe Gly Ala Ser Trp
        370                 375                 380

Asn Pro Val His Ala Ala Gly Ala Asn Ala Val Pro Ala Ala Val Tyr
385                 390                 395                 400

His His His His His Pro Tyr Val His Pro Gln Ala Pro Val Ala Ala
                405                 410                 415

Ala Ala Pro Asp Gly Arg Tyr Met Arg Ser Trp Leu Glu Pro Thr Pro
                420                 425                 430

Gly Ala Leu Ser Phe Ala Gly Leu Pro Ser Ser Arg Pro Tyr Gly Ile
                435                 440                 445

Lys Pro Glu Pro Leu Ser Ala Arg Arg Gly Asp Cys Pro Thr Leu Asp
        450                 455                 460

Thr His Thr Leu Ser Leu Thr Asp Tyr Ala Cys Gly Ser Pro Pro Val
465                 470                 475                 480

Asp Arg Glu Lys Gln Pro Ser Glu Gly Ala Phe Ser Glu Asn Asn Ala
                485                 490                 495

Glu Asn Glu Ser Gly Gly Asp Lys Pro Pro Ile Asp Pro Asn Asn Pro
                500                 505                 510

Ala Ala Asn Trp Leu His Ala Arg Ser Thr Arg Lys Lys Arg Cys Pro
        515                 520                 525

Tyr Thr Lys His Gln Thr Leu Glu Leu Glu Lys Glu Phe Leu Phe Asn
        530                 535                 540

Met Tyr Leu Thr Arg Asp Arg Arg Tyr Glu Val Ala Arg Leu Leu Asn
545                 550                 555                 560

Leu Thr Glu Arg Gln Val Lys Ile Trp Phe Gln Asn Arg Arg Met Lys
                565                 570                 575

Met Lys Lys Ile Asn Lys Asp Arg Ala Lys Asp Glu
                580                 585
```

US 8,795,650 B2

DERIVATION OF UNLIMITED QUANTITIES OF NEUTROPHILS OR MONOCYTE/DENDRITIC CELLS

RELATED APPLICATION

This application is a 35 USC §371 National Stage application of PCT Application No. PCT/US2005/044673 filed Dec. 9, 2005; and claims the benefit under 35 USC §119(e) to U.S. Application Ser. No. 60/635,264 filed Dec. 9, 2004, now abandoned. The disclosure of each of the prior applications is considered part of and is incorporated by reference in the disclosure of this application.

STATEMENT OF GOVERNMENT SUPPORT

This invention was made with government support under Grant No. CA56876 awarded by The National Institute of Health (NIH NCI). The government may has certain rights in the invention.

BACKGROUND OF THE INVENTION

1. Field of the Invention

The present invention relates generally to immunology and more specifically to immune responses and diseases involving chronic inflammation.

2. Background Information

Molecular pathways of normal hematopoietic cell differentiation, as well as the mechanisms by which oncogenes disrupt this process, remain poorly understood. In normal hematopoietic progenitor cells, a program of specific gene expression orchestrates commitment and differentiation of mature cells to multiple different lineages. In acute leukemias, however, oncoproteins interfere with this genetic program, resulting in the unregulated proliferation of cells that no longer retain the capacity to differentiate normally. In acute myeloid leukemias (AMLs) many known myeloid oncoproteins can block the differentiation of normal progenitors cultured in vitro in the presence of granulocyte-macrophage colony stimulating factor (GM-CSF) or interleukin-3 (IL-3). However, neither the genetic events that underlie normal hematopoietic cell differentiation nor the mechanism through which leukemic oncoproteins interfere with the execution of the program of lineage differentiation are well understood.

Macrophages and neutrophils orchestrate the inflammatory response, communicating with each other and with T and B cells to induce cell activation and cell proliferation, to recruit more inflammatory cells, to kill the invader, to protect the surrounding tissue, to induce longer-term protective immunity, and to down regulate the response once the microorganism has been eliminated. These same processes can become chronically activated, leading to a variety of human diseases, such as autoimmune disease, multiple sclerosis, liver cirrhosis, arthritis, atherosclerosis, vascular disease, and even cancer. Academic and industrial concerns have large research programs devoted to understanding processes of inflammation that arises from various insults. Determining how microorganisms evade the immune system (immune evasion) can lead to the development of microbial-specific inhibitors. Determining how innate immune cells (macrophage/dendritic cells and neutrophils) mount an immune attack to different microbes can lead to the development of drugs that promote specific responses. Characterizing how specific microbes, such as HIV, live within macrophage/dendritic cells and respond to drugs within that context can identify new therapeutic avenues. And finally, inhibiting inflammatory responses that cause the devastating non-microbial human diseases (listed above) comprises a vast potential to relieve human suffering and generate highly profitable drugs.

Research within this field is expensive and time-consuming. Because macrophage/dendritic cells and neutrophils are non-mitotic, they need to be derived from large numbers of mice when laboratories are knocking out a single gene to look at the effect. If the knockout is embryonic lethal, day 13 or 14 mice can still be used as a sources of these cells, but the labor, time, and costs increase if cells are derived from such embryos. Once a knockout mouse has been derived for a specific protein, the goal of characterizing the specific domains of the protein that are important for its function are difficult because one can not restore production of the protein, or specific mutants of the protein, within mature inflammatory cells.

SUMMARY OF THE INVENTION

The present invention relates to the discovery that estrogen receptor (ER)-fusion oncoproteins produce neutrophil-committed progenitors. Accordingly, the invention includes a method of using conditional forms of the HOX protein to immortalize monocyte/dendritic progenitor cells, In one embodiment, a method of modulating differentiation and immortalization of progenitor cells is provided including isolating progenitor cells from a subject, contacting the isolated cells with a fusion protein comprising a HOX oncoprotein and an estrogen receptor binding domain (ERBD), culturing the contacted cells with a combination of one or more multilineage cytokines, a myeloid-specific cytokine, and an estrogen agonist, whereupon culturing, the progenitor cells become immortalized and exhibit commitment to neutrophil and/or macrophage/dendritic lineage or exhibit multi-lineage differentiation potential.

In one aspect, the HOX oncoprotein is Hoxb8, Hoxa9, or Hoxa7. In a further related aspect, the fusion protein comprises an in-frame nucleic acid sequence encoding the general structure: $X_n$-ERBD-HOX, where ERBD is an estrogen receptor binding domain, $X_n$ is a nucleic acid residue and n is an integer from 0-24, and HOX is Hoxb8, Hoxa9, or Hoxa7.

In one aspect, the $X_n$-ERBD-HOX comprises Hoxb8, and includes a sequence as set forth in SEQ ID NO: 3.

In another aspect, the $X_n$-ERBD-HOX comprises Hoxa9, and includes a sequence as set forth in SEQ ID NO: 6.

In another aspect, the $X_n$-ERBD-HOX comprises Hoxa7, and includes a sequence as set forth in SEQ ID NO: 9.

In one aspect, the estrogen agonist is β-estradiol.

In another aspect, the method includes removing the estrogen agonist upon expression of genes indicative of a neutrophil or macrophage/dendritic cell progenitor phenotype, thereby committing the cells to differentiate into mature neutrophils and/or macrophages/dendritic cells.

In one aspect, the multilineage cytokines are selected from stem cell factor, IL-6, IL-3, GM-CSF and combinations thereof or any cytokine that functions to sustain the proliferation of myeloid progenitors. In another aspect, the myeloid specific cytokine is IL-5 or G-CSF.

In one aspect, the method includes isolating cells from bone marrow or fetal liver cells. Moreover, the cells are obtained from wild-type or genetically-altered organisms.

In one embodiment, an immortalized, isolated neutrophil, macrophage/dendritic, biphenotypic neutrophil/macrophage/dendritic, and/or multipotent neutrophil/macrophage/dendritic/eosinophil/mast cell is provided, which is obtained from a bone marrow or fetal liver cell cultured in the presence of a combination of one or more multilineage and myeloid cytokines and infected with a vector comprising a fusion protein having a HOX oncoprotein and an estrogen receptor binding domain, where the infected cell becomes immortalized in the presence of an estrogen agonist and exhibits differentiation potential to the neutrophil, macrophage/dendritic, biphenotypic neutrophil/macrophage/dendritic, and/or multipotent neutrophil/macrophage/dendritic/eosinophil/mast lineage.

In another embodiment, an isolated neutrophil, macrophage/dendritic, biphenotypic neutrophil/macrophage/dendritic, and/or multipotent neutrophil/macrophage/dendritic/eosinophil/mast cell is provided which is obtained from a bone marrow or fetal liver cell infected with a vector comprising a fusion protein having a HOX oncoprotein and an estrogen receptor binding domain and cultured in the presence of an estrogen agonist and a combination of one or more multilineage and myeloid cytokines, wherein the cultured cell differentiates into a mature neutrophil, macrophage/dendritic, biphenotypic neutrophil/macrophage/dendritic, and/or multipotent neutrophil/macrophage/dendritic/eosinophil/mast cell after removal of the estrogen agonist.

In a related aspect, the cells are obtained from a wild-type or genetically-altered organism.

In one embodiment, a method of evaluating the effect of a genetically-altered gene on a neutrophil or a macrophage/dendritic cell is provided, including knocking-out or transferring a gene of interest to a subject animal, obtaining a sample of bone marrow or fetal liver cells from the subject animal and a wild-type animal, infecting the cells from each animal with a vector comprising a fusion protein having a HOX oncoprotein and an estrogen receptor binding domain and culturing the cells in the presence of an estrogen agonist and a combination of one or more multilineage and myeloid cytokines, removing estrogen from the cultured cells upon expression of genes indicative of a neutrophil or macrophage/dendritic cell progenitor phenotype, culturing the cells in the absence of the agonist and assaying the cells for one or more inflammatory responses associated with neutrophil or macrophage/dendritic cells, where differences in one or more inflammatory responses between the cells from the knock-out/transgenic subject animal and wild-type animal correlate with the altered gene of interest.

In one aspect, the method includes culturing the cells in the presence of an agent of interest and evaluating the agent for one or more responses associated with neutrophil or macrophage/dendritic cells. In another aspect, the method includes culturing the cells with a microbial pathogen.

In another aspect, the method includes transplanting the cultured cells into model animals presenting one or more inflammatory disease symptoms or a microbial infection and determining one or more differences in behavior between the cultured cells and endogenous wild-type neutrophils or macrophages, where determined differences are indicative of the function of the knockout gene in the inflammatory process.

In one aspect, the behavior is associated with the ability of cells to mediate steps in the disease pathology related to inflammation, where the behavior includes, migration to inflammatory sites, microbial phagocytosis, cytokine release, recruitment of phagocytes, presentation of antigen to lymphoid cells, recruitment of lymphoid cells, or a combination thereof.

In one aspect, the disease symptoms are associated with autoimmune diseases, multiple sclerosis, liver cirrhosis, arthritis, or atherosclerosis.

In one embodiment, a method of identifying processes in immune cells undergoing differentiation or maturation is provided including obtaining a sample of bone marrow or fetal liver cells from a genetically altered or a wild-type control subject, infecting the cells from the subject with a vector comprising a fusion protein having a HOX oncoprotein and an estrogen receptor binding domain and culturing the cells in the presence of an estrogen agonist and a combination of one or more multilineage and myeloid cytokines, removing samples of cells from the culture at various time points, and assaying the cells for changes in morphology, physiology, and/or gene expression, where the changes observed at different time-points correlate with different processes associated with neutrophil and/or macrophage/dendritic cell differentiation or maturation.

In a related aspect, the method includes removing the estrogen agonist upon expression of one or more gene markers associated with an immune cell exhibiting a neutrophil and/or macrophage/dendritic cell progenitor phenotype and culturing the cells in the absence of the agonist.

In one embodiment, an isolated nucleic acid encoding an amino acid sequence as set forth in SEQ ID NO: 16 or SEQ ID NO: 17 is provided. In a related aspect, the nucleic acid comprises SEQ ID NO: 3 or SEQ ID NO: 6.

In another embodiment, an expression vector is provided including an operably linked nucleic acid encoding a fusion protein comprising an in-frame nucleic acid sequence encoding the general structure: $X_n$-ERBD-HOX. In a related aspect, a host cell is provided including the vector encoding a fusion protein of the general structure: $X_n$-ERBD-HOX.

In one embodiment, a method of treating an inflammatory disorder is provided including administering to a subject in need thereof a pharmaceutical composition comprising the isolated cells of the present invention and a pharmaceutically acceptable carrier.

Exemplary methods and compositions according to this invention are described in greater detail below.

DETAILED DESCRIPTION OF THE INVENTION

Figure 1:
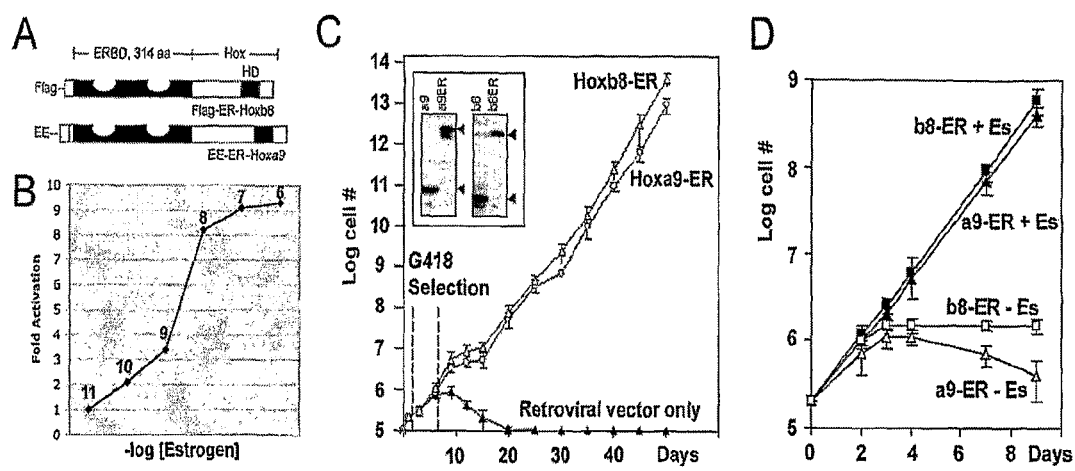
FIGS. 1A-D show that Hoxb8-ER and Hoxa9-ER function conditionally at the biochemical and cellular levels. Panel A: Estrogen-binding domain (ERBD) of the estrogen receptor fused to Hoxa9 or Hoxb8. Epitope tags are indicated at left. HD represents the homeodomain. Panel B: Estrogen-responsive transcriptional function of Hoxa9-ER, measured as coactivation through TGAT-TTAT motifs in conjunction with E2a-Pbx1 in 293T cells. Hoxb8-ER yielded an estrogen-induced concentration curve that was superimposable on Hoxa9-ER. Panel C: Proliferation of GM-CSF-dependent progenitors immortalized by Hoxa9-ER or Hoxb8-ER. Retroviral infection was performed at day 0, followed by a 4-day selection in G418. Inserted panel represents a Western blot using anti-Hoxa9 (left) and anti-Flag antibodies (right) on G418-selected progenitors immortalized by Hoxa9-ER or Hoxb8-ER, respectively. Immortalization kinetics and progenitor doubling times were somewhat faster for under SCF culture conditions. Panel D: Proliferation of GM-CSF-dependent progenitors immortalized by Hoxa9-ER or Hoxb8-ER following estrogen withdrawal. Proliferation of SCF-dependent progenitors continued for 4 to 5 days, while that of GM-CSF-dependent progenitors was rapidly terminated by day 2.

Before the present compositions, methods, and computational methodologies are described, it is to be understood that this invention is not limited to particular compositions, methods, and experimental conditions described, as such compositions and methods may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "a nucleic acid" includes one or more nucleic acids, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure. All publications mentioned herein are incorporated herein by reference in their entirety.

As used herein "immortalized," including grammatical variations thereof, means a cell population changed from having a finite life span to one possessing an infinite life span.

As used herein "differentiation," including grammatical variations thereof, means a process whereby relatively unspecialized cells acquire specialized structure and/or functional features that characterize the cells, tissues, or organs of the mature organism or some other relatively stable phase of the organism's life history.

As used herein "progenitors," including grammatical variations thereof, are the more differentiated progeny of stem cells that give rise to distinct subsets of mature blood cells and lack the capacity for self-renewal possessed by true stem cells.

As used herein "oncoprotein," including grammatical variations thereof, means any protein associated with the causation of cancer.

As used herein "multi-lineage differentiation potential," including grammatical variations thereof, means a progenitor cell having the capability of development into a neutrophil, macrophage/dendritic, biphenotypic neutrophil/macrophage/dendritic, and/or eosinophil/mast cell.

In the context of destroying pathogens, complexed receptor systems are used to migrate toward invaders, recognize invaders, respond to invaders, and activate the maturation and division of T and B cells that also respond to the same foreign organism. Migration toward the site of inflammation is mediated by chemokine receptors (e.g., CCR2 and CCR5) in response to ligands such as MIP1 alpha and MIP1 beta, which are secreted by activated macrophages at the site of the inflammatory response. Recognition of pathogens involved receptors that bind bacterial products (e.g., Toll pattern-recognition receptors TLR2 and TLR4 or FPR and FPRL2 receptors that bind bacterial peptides such as fMLP), lectins that bind sugars on the surface of the pathogen (e.g. Dectin-1, DCIR, DCAR, DCL-1, MCL, MGL2, MRC1), and receptors that recognize the Fc region of antibodies that are bound to the pathogen (IgG and IgE Fc receptors, more than 5 genes encode these proteins). The response of a macrophage/dendritic cell or neutrophil to a pathogen is controlled by a complex system of receptors that transmit "activating" or "inhibiting" signals and that also tell the cell whether there is evidence of "self" MHC class I antigens (e.g. PIR-A and PIR-B receptors). Macrophage/dendritic cells and neutrophils then engage in a measured inflammatory response, which includes phagocytosis/killing of the microbe using NAPH oxidase, proteinases such as cathepsin and metalloproteinases, and enzymes that break down lipid (lipoprotein lipase) and bacterial cell walls (lysozyme), which are stored in phagocytic vesicles of the mature macrophage/dendritic cell or neutrophil. To prevent broad tissue damage, macrophage/dendritic cells and neutrophils also secrete specific inhibitors of their own intracellular proteases, such as cystatins and serpins to prevent broad tissue damage). Activation of monocyte/dendritic cells and neutrophils results in the induction of a broader inflammatory gene response that is designed to recruit and activated more cells and prepare the surrounding tissue for ensuing inflammatory response. This response produces factors that activate the maturation and proliferation of killer T cells (e.g., TNF9, ICOS-L, IL12, IL23), factors that recruit more inflammatory cells (e.g. MCP1, MCP3, MIP1alpha, RANTES), and factors that elicit a broad general response within both hematopoietic and non-hematopoietic cells (e.g., IL1alpha, IL1beta, IL6, TNFalpha, and IFN-beta). Dendritic cells are intimately involved in the activation of T cells responsive to foreign antigens. Dendritic cells uniquely express MHC Class II antigens, as well as CD11c and CD86. Each of these markers is upregulated in Hoxb8-immortalized macrophage/dendritic cells (Table 3). Dendritic cells present foreign antigens on their MHC Class II complexes to T cells, and the T cell clones containing T cell receptors that recognize the same antigen are activated by interacting with both the MHC Class II/antigen complex and the co-stimulatory signals derived from the dendritic cells.

By using genomic or other profiling tools, the genetic program of progenitor differentiation can be defined by comparing gene expression in immature progenitors growing in the presence of estrogen vs. cells maturing in the absence of estrogen. The cell system can then be used to identify the mechanisms that control stage-specific gene expression by determining the transcriptional mechanisms required to activate stage-specific gene expression.

By allowing immature proliferating progenitors immortalized by Hoxb8-ER or by Hoxa9-ER to mature in the absence of estrogen, the desired number of macrophage/dendritic cells or neutrophils can be obtained. Any protein component can then be purified by classical mechanisms. Large numbers of mature macrophage/dendritic cells or neutrophils can be derived for large-scale screening efforts. Homogeneity from batch to batch is ensured by the clonal nature of the cells used for the assay.

As disclosed herein, progenitors committed to the macrophage/dendritic lineage or neutrophil lineage can be immortalized by Hoxb8-ER or Hoxa9-ER, respectively. The effect of the target gene elimination can then be observed in mature macrophage/dendritic cells or in neutrophils following their differentiation after withdrawal of estrogen. One can then go on to determine the specific domain requirements of the knockout protein by re-expressing a panel of mutants of the knockout gene. Factors that interact with functionally-important domains can then be defined by interaction with the wild-type protein, but not with specific mutants that disrupt function in the knockout macrophage/dendritic cells or neutrophils. For example, human atherosclerosis involves the accumulation of macrophages into vascular lesions. A mouse model for atherosclerosis exists. One could ask the question, is the CCR2 chemokine receptor important for homing of macrophages to atherosclerotic lesions in vivo. If this was essential, then CCR2 inhibitors might be therapeutic agents in atherosclerosis. Wild-type and CCR2 knockout macrophage/dendritic progenitors would be immortalized by Hoxb8-ER. Mature cells would be generated and infused into mice in which atherosclerotic lesions were present. By measuring the difference in homing of wild-type vs. CCR2 knockout macrophage/dendritic cells to the lesion, one can determine the role of CCR2 in macrophage accumulation in the lesion.

Herein is described a rapid and convenient method to produce unlimited macrophages or neutrophils from mice surviving past embryonic d13, a method that overcomes the significant time, cost and animal mortality involved in using mice as a source of mature phagocytes. The functional properties of macrophages derived by maturation of Hoxb8-ER GM-CSF progenitors are at least as good as those produced by cell lines, such as TPA-induce macrophage differentiation of HL60 cells, IL6-induced macrophage differentiation of M1 AML cells, or unstimulated macrophages represented by the RAW1 cell line. These models of macrophage differentiation are also accompanied by up-regulation of Egr-1, Egr-2, ATF3, c-fos, cjun, Rel-B and down-regulation of c-Myb, c-Myc transcription [Krishnaraju, K., B. Hoffman, and D. A.

Liebermann, Blood, 1998. 92 (6): p. 1957-66; Liebermann, D. A. and B. Hoffman, Stem Cells, 1994. 12 (4): p. 352-69; Kharbanda, S., et al., J Clin Invest, 1991. 88 (2): p. 571-7;]. The functional maturation of neutrophils derived from Hoxb8-ER SCF progenitors is stronger than that produced by G-CSF-induced differentiation of either 32D progenitors or Hoxa9 progenitors. 32D progenitors fail to up-regulate secondary granule genes such as lactoferrin, and Hoxa9 progenitors fail to down-regulate e-Myb and the promyelocytic genes, neutrophil elastase and MPO, and fail to up-regulate the secondary granule gene lactoferrin [Calvo, K. R., et al., Mol Cell Biol, 2000. 20 (9): p. 3274-85]. The incomplete transcriptional modeling of these inducible cell lines is likely due to the persistent oncoprotein activity during differentiation induction, which contrasts the complete inactivation in oncoprotein-ER fusions. ATRA-induced differentiation of GM-CSF-dependent EPRO promyelocytes [Gaines, P., J. Chi, and N. Berliner, J Leukoc Biol, 2005. 77 (5): p. 669-79] yields results comparable to those observed in with Hoxb8-ER, and interestingly also inactivates the intrinsic oncoprotein (a dominant-negative retinoic acid receptor a), using supra-physiologic levels of ATRA.

Conditional oncoproteins described to date have not evidenced reproducible derivation of lineage-specific progenitors that execute normal differentiation. Avian v-Myb-ER immortalizes primary chicken monocyte progenitors that differentiated, unexpectedly, into multinucleated giant cells similar bone-marrow-derived osteoclasts [Engelke, U., D. M. Wang, and J. S. Lipsick, J Virol, 1997. 71 (5): p. 3760-6]. Their expansion in the presence of estrogen is also limited to $10^7$. Mll-Enl-ER (tamoxifen-regulated) immortalizes a biphenotypic progenitor that requires 14 days to exit the cell cycle following removal of tamoxifen and to differentiate into neutrophils and monocytes [Zeisig, B. B., et al., Mol Cell Biol, 2004. 24 (2): p. 617-28]. Terminal differentiation of progenitors immortalized by E2a-ER-Pbx1 is variable (5 to 12 days), and while derivation of neutrophil-committed progenitors is common using the Δ1 E2a-Pbx1 mutant, derivation of macrophage-committed progenitors is rare [Sykes, D. B. and M. P. Kamps, Blood, 2001. 98 (8): p. 2308-18], an observation somewhat akin to the behavior of Hoxa9-ER in the present disclosure, which yielded mostly biphenotypic progenitors, a lower number of neutrophil-committed progenitors, and rare monocyte-committed progenitors. Therefore, while neutrophils and macrophages produced by inactivation of conditional oncoproteins appear more normal than those produced by many inducible systems, oncoprotein-specific functions dictate the expansion potential, the differentiation stage, and the differentiation potential of the immortalized progenitor. When matched with appropriate cytokine conditions, Hoxb8-ER simply has a useful property of generating progenitors that execute differentiation to pure populations of neutrophils or macrophages, a technique that can be used to produce unlimited supply of genetically-defined macrophages or neutrophils for bioassays, gene expression analysis, conventional protein purification protocols, and other methods used to investigate the differentiation, signaling, and effector functions of phagocytes.

One application of the Hoxb8-ER systems is understanding how Hox oncoproteins block differentiation in myeloid leukemia. Hoxb8 was the prototypic Hox oncoprotein in leukemia, first discovered due to its transcription activation by an integrated provirus in WEHI-3B leukemia cells [Perkins, A., et al., Proc Natl Acad Sci USA, 1990. 87 (21): p. 8398-402]. Based on genomic analysis, it is clear that Hoxb8 controls a switch between progenitor proliferation, characterized by expression of c-Myb, c-Myc, Pontin, Reptin, Gfi-1, and HMGB3, and cell cycle arrest/terminal differentiation, characterized by expression of ATF3, JunB, c-fos, RelB, c-Jun, JunD1, Egr-1, Egr2. From a mechanistic standpoint, c-Myb, c-Myc, Pontin, Reptin, Gfi-1, and HMGB3 are likely to be essential targets that sustain expansion of Hox-immortalized progenitors. C-Myb, the cellular homologue of the Avian Myeloblastosis virus oncogene v-Myb, is a transcriptional activator required for self-renewal of short-term reconstituting hematopoietic stem cells, is transcriptionally activated by proviral integrations in both myeloid and lymphoid leukemias [Lipsick, J. S. and D. M. Wang, Oncogene, 1999. 18 (19): p. 3047-55], and inhibits IL-6 induced macrophage differentiation of M1 AML progenitors. Removal of c-Myb down-regulates the cell cycle and induces red cell differentiation in erythroleukemia progenitors [Chen, J., C. S. Kremer, and T. P. Bender, Oncogene, 2002. 21 (12): p. 1859-69, Lyon, J. J. and R. J. Watson, Differentiation, 1995. 59 (3): p. 171-8] and induces granulocyte/macrophage differentiation in myeloid progenitors (FDCP-mix A4, [White, J. R. and K. Weston, Oncogene, 2000. 19 (9): p. 1196-205]). c-Myc overexpression is one of the most common oncogenic events in human malignancy, and its expression is required for Myb-mediated transformation, [Kumar, A., C. M. Lee, and E. P. Reddy, J Biol Chem, 2003. 278 (13): p. 11480-8]. Pontin and Reptin are DNA helicases involved in chromatin remodeling and transcriptional activation [Kurokawa, Y., et al., DNA Seq, 1999. 10 (1): p. 37-42], and expression of Pontin is required for transformation by c-Myc [Wood, M. A., S. B. McMahon, and M. D. Cole, Mol Cell, 2000. 5 (2): p. 321-30] and by beta-catenin [Feng, Y., N. Lee, and E. R. Fearon, Cancer Res, 2003. 63 (24): p. 8726-34]. Gfi-1 and Hmgb3 are also implicated in stem cell expansion. Gfi-1 is a transcriptional repressor that promotes T cell proliferation [Zhu, J., et al., Immunity, 2002. 16 (5): p. 733-44], is activated in murine T cell lymphoma [Scheijen, B., et al., J Virol, 1997. 71 (1): p. 9-16], and is normally expressed in hematopoietic stem cells (HSC), common lymphoid progenitors (CLP), and CFU-GM [Hock, H., et al., Immunity, 2003. 18 (1): p. 109-20]. Hmgb3 is related to the High Mobility Group (HMG) family of non-histone, chromatin-binding proteins that facilitate nucleosome remodeling, and its expression is also high in Lin−, c-kit+, Sca-1+, IL-7Ralpha− long-term repopulating HSC, in Ter119+erythroid progenitors, CLP, and common myeloid progenitors (CMP [Nemeth, M. J., et al., Blood, 2003. 102 (4): p. 1298-306]), and it is essential for the expansion of CLPs and CMPs from HSCs [Nemeth, M. J., et al., Blood, 2005. 105 (2): p. 627-34]. Determining how Hox oncoproteins maintain transcription of c-Myb, c-Myc, Pontin, Reptin, Gfi-1, and Hmgb3 is one application of this cell system that may explain how Hox proteins immortalize myeloid progenitors and contribute to AML.

A second application of the Hoxb8-ER system is to study transactivation mechanisms in terminal differentiated phagocytes, such as those controlling activation of the secondary granule gene Lactoferrin, the pattern recognition gene Formyl peptide receptor, or the antimicrobial gene Cathelin. This field has been encumbered by the unavailability of appropriate model systems [Gaines, P., J. Chi, and N. Berliner, J Leukoc Biol, 2005. 77 (5): p. 669-79]. Understanding such transcriptional mechanisms will also provide insight into the oncogeneic mechanism of differentiation-arrest and myeloid leukemogenesis. New genes controlling phagocyte differentiation or function may also be identified. One candidate is MKP1 (MAP kinase phosphatase 1), which was up-regulated 30-fold coincident with neutrophil or monocyte differentiation. MKP1 is a duel specificity phosphatase that negatively regulates the cell cycle by dephosphorylating and inactivating MAP kinases, and is activated by p53 during G1 arrest in response to DNA-damage [Li, M., et al., J Biol Chem, 2003. 278 (42): p. 41059-68]. Transactivation of MKP1 represents a mechanism by which Hox down-regulation could induce terminal differentiation by dephosphorylating multiple cellular targets.

Although not to be bound by theory, the accuracy of the Hoxb8-ER model predicts a broader conceptual application-cognate differentiation models of other myeloid lineages, lymphoid lineages, or even of epithelial stem cells that control ductal formation in the breast or microvillar development in the colon should be able to be derived by expressing conditional oncogenes in their tissue-specific stem cells cultured in the presence of cytokines that support the their expansion/differentiation programs. In considering this hypothesis, it would be important to use oncogenes found specifically in cancers of the cell type for which the model is being generated, and that have been proven to alter differentiation of its corresponding stem cell. Such models of tissue differentiation would be useful both in understanding how oncogenes enforce the stem cell phenotype in cancer, as well as in understanding differentiated cell functions.

In one embodiment, a method of evaluating the effect of a genetically-altered gene on a neutrophil or a macrophage/dendritic cell is provided, including knocking-out or transferring a gene of interest to a subject animal, obtaining a sample of bone marrow or fetal liver cells from the subject animal and a wild-type animal, infecting the cells from each animal with a vector comprising a fusion protein having a HOX oncoprotein and an estrogen receptor binding domain and culturing the cells in the presence of an estrogen agonist and a combination of one or more multilineage and myeloid cytokines, removing estrogen from the cultured cells upon expression of genes indicative of a neutrophil or macrophage/dendritic cell progenitor phenotype, culturing the cells in the absence of the agonist and assaying the cells for one or more inflammatory responses associated with neutrophil or macrophage/dendritic cells, where differences in one or more inflammatory responses between the cells from the knock-out/transgenic subject animal and wild-type animal correlate with the altered gene of interest.

In one aspect, the method includes culturing the cells in the presence of an agent of interest and evaluating the agent for one or more responses associated with neutrophil or macrophage/dendritic cells. In another aspect, the method includes culturing the cells with a microbial pathogen.

In another aspect, the method includes transplanting the cultured cells into model animals presenting one or more inflammatory disease symptoms or a microbial infection and determining one or more differences in behavior between the between the cultured cells and endogenous wild-type neutrophils or macrophages, where determined differences are indicative of the function of the knockout gene in the inflammatory process.

In one aspect, the behavior is associated with the ability of cells to mediate steps in the disease pathology related to inflammation, where the behavior includes, migration to inflammatory sites, microbial phagocytosis, cytokine release, recruitment of phagocytes, presentation of antigen to lymphoid cells, recruitment of lymphoid cells, or a combination thereof.

In one aspect, the disease symptoms are associated with autoimmune diseases, multiple sclerosis, liver cirrhosis, arthritis, or atherosclerosis.

Hox genes are developmental regulators whose persistent expression has been found to underlie myeloid leukemia, a disease in which the progenitors of macrophages, dendritic cells, and neutrophils are blocked in their differentiation, and can continue to divide as progenitor cells. Here in described is the use of the ability of Hox proteins to block differentiation to control cell differentiation and immortalize specific types of progenitor cells. Using a conditional form of HOX, a means of generating unlimited numbers of immature progenitors that can differentiate into mature, normal macrophage/dendritic cells when directed to do so is disclosed.

In one embodiment, a method of modulating differentiation and immortalization of progenitor cells is provided including isolating progenitor cells from a subject, contacting the isolated cells with a fusion protein comprising a HOX oncoprotein and an estrogen receptor binding domain (ERBD), culturing the contacted cells with a combination of one or more multilineage cytokines, a myeloid-specific cytokine, and an estrogen agonist, whereupon culturing, the progenitor cells become immortalized and exhibit commitment to neutrophil and/or macrophage/dendritic lineage or exhibit multi-lineage differentiation potential.

In a related aspect, the HOX oncoprotein is Hoxb8, Hoxa9, or Hoxa7. In a further related aspect, the fusion protein comprises an in-frame nucleic acid sequence encoding the general structure: $X_n$-ERBD-HOX, where ERBD is an estrogen receptor binding domain, $X_n$ is a nucleic acid residue and n is an integer generally between 0-24, where n is sufficient to encode an immunologic tag for the purposes of identifying the fusion protein using anti-epitope antibodies, and HOX is Hoxb8, Hoxa9, or Hoxa7.

In one aspect, the $X_n$-ERBD-HOX comprises Hoxb8, and includes the sequence as set forth in SEQ ID NO: 3. In another aspect, the $X_n$-ERBD-HOX comprises Hoxa9, and includes the sequence as set forth in SEQ ID NO: 6. In another aspect, the $X_n$-ERBD-HOX comprises Hoxa7, and includes the sequence as set forth in SEQ ID NO: 9.

These cell lines can be made from any normal mouse or any genetic mutant of a mouse that survives birth, using bone marrow as the source of cells subjected to the cell line derivation procedure. These cell lines can be made from any normal mouse or any genetic mutant of a mouse that survives to day 13, using fetal liver progenitors as the source of cells for the immortalization procedure. The mature macrophage/dendritic cells or neutrophils are functionally normal by all criteria. They express a vast complement of receptors involved in immune function, and produce a wide spectrum of pro-inflammatory cytokines in response to activation by pathogens. In a related aspect, such animals may be transgenic, knockin, or knockout animals. In one embodiment, the knockin animal is a mouse. In another embodiment, the animal is a knockout mouse. One embodiment comprises a disruption in an endogenous alleles encoding a gene of interest thought to be associated with inflammation or an immune response.

Transgenic/knockin/knockout animals may be mice, rats and rabbits, or mammals such as pigs, goats, sheep, and monkeys. Other standard animals used in the act for transgenic knockin or knockout models an be used in the present invention. For example, such a transgenic, knock-out or knockin animal can be used as a control, when identifying and testing drugs that can be useful treating an inflammatory disorder. Thus the transgenic, knockin, and knockout animals of the present invention can be used in drug screens and the like. Cells from the transgenic, knockin and knockout mice are also part of the present invention.

Transgenic vectors, including viral vectors, or cosmid clones (or phage clones) corresponding to the wild type locus of candidate gene, can be constructed using the isolated gene of interest. Cosmids may be introduced into transgenic mice using published procedures (Jaenisch, *Science*, 240:1468-1474 (1988)).

Gene expression is disrupted, according to the invention, when no functional protein is expressed. One standard method to evaluate the phenotypic effect of a gene product is to employ knock-out technology to delete a gene as described in U.S. Pat. No. 5,464,764, Issued Nov. 7, 1995; and U.S. Pat. No. 5,777,195, Issued Jul. 7, 1998 (both of which are hereby incorporated by reference herein in their entireties).

Monocyte/dendritic progenitor cell lines immortalized by HOX fusion proteins are disclosed using CCR2 knockout cells, demonstrating the prediction that progenitors from mice harboring genetic mutations will also be susceptible to immortalization by the disclosed methods. Further, the present invention demonstrates that day 13 fetal liver cells can be immortalized by HOX containing fusion oncoproteins, permitting the derivation of either macrophage/dendritic or neutrophil progenitor cells lines, respectively, from knockout mice having embryonic lethal phenotypes produce by ablation of genes controlling the immune system. In one case, progenitors from a mouse in which the DAP12 gene was removed were immortalized. DAP12 signals downstream of Toll receptors, which bind bacterial components.

The function of the HOX oncoprotein is made conditional by fusing it to the estrogen-binding domain of the estrogen receptor (e.g, SEQ ID NO: 10). The Hoxb8-ER cDNA is inserted into a retroviral vector, and the Hoxb8-ER retrovirus are used to infect mouse marrow progenitors expanded from marrow by culturing in one or more multi-lineage cytokines (e.g., but not limited to, stem cell factor, IL-6, and IL-3). In one aspect, a viral vector that comprises a nucleic acid encoding a fusion protein is provided. For example, but not limited to, such fusion proteins may comprise the amino acid sequence as set forth in SEQ ID NO: 16 or SEQ ID NO: 17.

In one aspect, the viral vector is a herpes simplex viral vector, an adenoviral vector, or an adeno-associated viral vector (AAV). In another aspect, the viral vector is a retroviral vector, for example but not limited to, an HIV retroviral vector, a VL 30 vector, a MSCV retroviral vector, or a Harvey Murine Sarcoma Vector. In a related aspect, a progenitor cell is transduced by being co-cultured with a retroviral producer cell line. In another aspect, transducing a progenitor cell with $X_n$-ERBD-HOX is performed with a DNA vector (i.e., a naked DNA) that comprises a nucleic acid encoding the fusion protein.

Infected/transfected progenitors can then be cultured in the presence of tissue culture medium containing an estrogen agonist (to keep the fusion protein active) and a myeloid specific cytokine (e.g., GM-CSF, G-CSF and Fl.T-3), which maintains proliferation of progenitors committed to the neutrophil or macrophage/dendritic lineage. In one aspect, the agonist may be β-estradiol, raloxifene, tamoxifen, toremifene, and clomiphene. Such agonists may be present at about 0.1 to about 0.5, about 0.5 to about 1.0, or about 1 to about 5 micromolar.

Subsequent to infection, populations of immortalized progenitors emerge (FIG. 1A, pictures grow in the presence of estrogen are designated with a "+") that express numerous genes indicative of their macrophage/dendritic cell progenitor phenotype (Table 1).

These progenitors proliferate indefinitely. Following oncoprotein inactivation, they stop dividing and mature into cells having the typical morphology of macrophage/dendritic cells (FIG. 1A, lanes designated "−" estrogen for 1, 4, or 6 days). The progenitors stop cell division using a well-orchestrated process that involves downregulation of genes involved in cell cycle control, nucleotide biosynthesis, DNA replication, and RNA maturation (FIG. 2, Table 2). In one embodiment, a method of identifying processes in immune cells undergoing differentiation or maturation is provided including obtaining a sample of bone marrow or fetal liver cells from a genetically altered or a wild-type control subject, infecting the cells from the subject with a vector comprising a fusion protein having a HOX oncoprotein and an estrogen receptor binding domain and culturing the cells in the presence of an estrogen agonist and a combination of one or more multilineage and myeloid cytokines, removing samples of cells from the culture at various time points, and assaying the cells for changes in morphology, physiology, and/or gene expression, where the changes observed at different time-points correlate with different processes associated with neutrophil and/or macrophage/dendritic cell differentiation or maturation.

In a related aspect, the method includes removing the estrogen agonist upon expression of one or more gene markers associated with an immune cell exhibiting a neutrophil and/or macrophage/dendritic cell progenitor phenotype and culturing the cells in the absence of the agonist.

Figure 3:
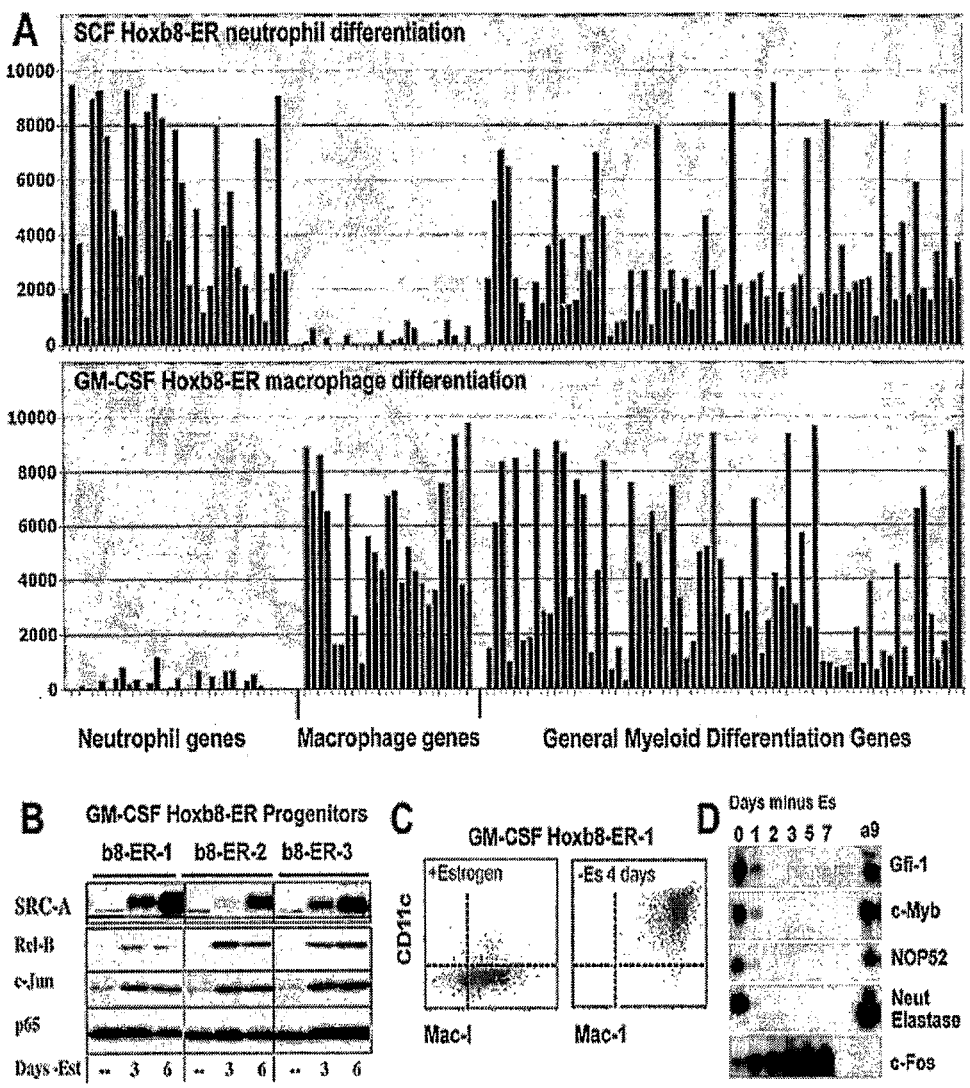
FIGS. 3A-3D demonstrate lineage-specific gene up-regulation in Hoxb8-ER SCF neutrophil progenitors and Hoxb8-ER GM-CSF macrophage progenitors. Panel A: Affymetrix gene arrays were used to quantitate the expression levels of 128 myeloid genes in a Hoxb8-ER SCF neutrophil cell line (top panel) and a Hoxb8-ER GM-CSF macrophage cell line (lower panel) in the presence of estradiol (blue) and at 6 days of differentiation following estradiol withdrawal (red). X-axis was plotted with three different subsets of genes: neutrophi-restricted (left section), macrophage-restricted (middle section) and general myeloid differentiation genes (right section). The names of the genes plotted here are underscored in Table 4. The Y-axis plots the relative abundance of RNA, with blue designating basal levels in undifferentiated progenitors and red designating levels following 6 days of differentiation. Panels B-D: Verification of changes observed on Affymetrix arrays, using immunoblotting for the macrophage scavenger receptor (SCR-A) and the transcription factors Rel-B and c-Jun three and six days following removal of estradiol from Hoxb8-ER GM-CSF macrophage progenitors (panel B), FACS analysis for CD11c in Hoxb8-ER GM-CSF progenitors in the presence of estradiol and 4 days after withdrawal of estradiol (panel C), and by Northern blotting (panel D).

Coincident with ceasing proliferation, progenitors immortalized by fusion proteins of the present invention differentiate into mature macrophage/dendritic cells, down-regulating genes expressed specifically during the middle stages of myeloid differentiation (Table 2) and up-regulating a large number of cell surface receptors characteristic of macrophage/dendritic cells (FIG. 3, Table 3). Note, for example, specific expression of the MHC class II genes, of CD83, and of CD11c, all of which are markers for the dendritic cell, a specialized antigen-presenting cell derived from the monocyte lineage.

Figure 2:
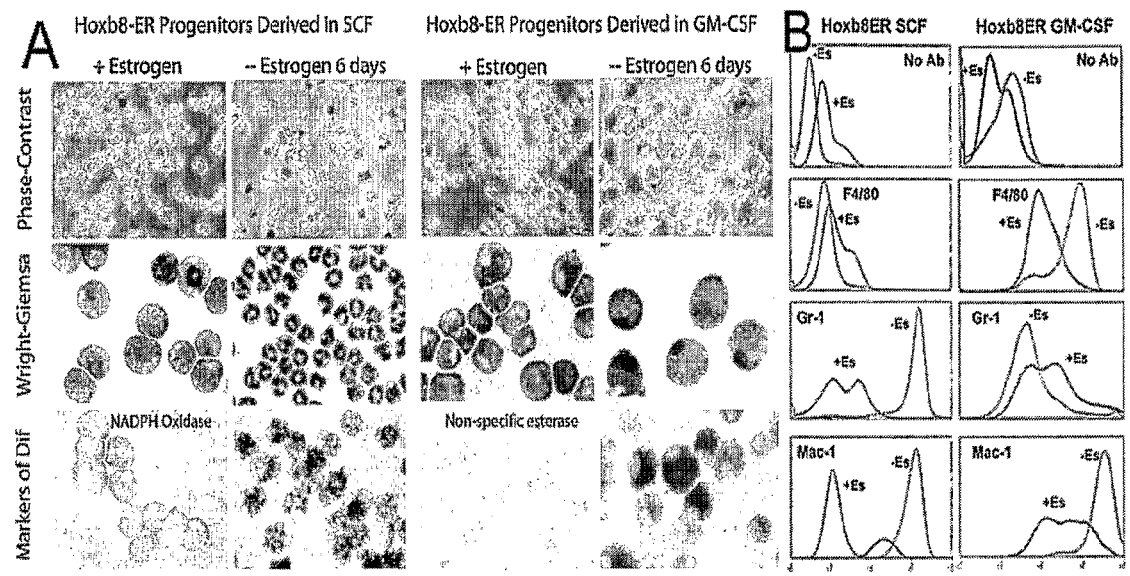
FIGS. 2A and 2B show that Hoxb8-ER SCF progenitors execute neutrophil differentiation while Hoxb8-ER GM-CSF progenitors execute macrophage differentiation. Panel A: Morphologic changes of Hoxb8-ER SCF neutrophil progenitors (left) and Hoxb8-ER GM-CSF macrophage progenitors (right) following estrogen withdrawal. Immortalized progenitors were washed twice in 10 mL of PBS, and then cultured in Myeloid Cell Medium without added β-estradiol. Cells were collected after 6 days and subject to Wright-Giemsa staining, NBT reduction assay (for neutrophils), NSE assay (for macrophages) after cytocentrifuge preparation of cells. Panel B: FACS analysis of expression of neutrophil or macrophage-specific surface markers by Hoxb8-ER progenitors before and after differentiation. Expression of Gr-1 (neutrophil differentiation antigen), F4/80 (macrophage differentiation antigen) and Mac-1 (general myeloid differentiation antigen), in Hoxb8-ER SCF neutrophil progenitors (left) or Hoxb8-ER GM-CSF macrophage progenitors (right) cultured in the presence of estradiol (blue tracing) or following the removal of estradiol for 6 days (red tracing).

The progenitors immortalized by the method of the present invention mature visually into cells that look identical to normal macrophage/dendritic cells (FIG. 1). In one embodiment, an immortalized, isolated neutrophil, macrophage/dendritic, biphenotypic neutrophil/macrophage/dendritic, and/or multipotent neutrophil/macrophage/dendritic/eosinophil/mast cell is provided, which is obtained from a bone marrow or fetal liver cell cultured in the presence of a combination of one or more multilineage and myeloid cytokines and infected with a vector comprising a fusion protein having a HOX oncoprotein and an estrogen receptor binding domain, wherein the infected cell becomes immortalized in the presence of an estrogen agonist and exhibits differentiation potential to the neutrophil, macrophage/dendritic, biphenotypic neutrophil/macrophage/dendritic, and/or multipotent neutrophil/macrophage/dendritic/eosinophil/mast lineage.

In another embodiment, an isolated neutrophil, macrophage/dendritic, biphenotypic neutrophil/macrophage/dendritic, and/or multipotent neutrophil/macrophage/dendritic/eosinophil/mast cell is provided which is obtained from a bone marrow or fetal liver cell infected with a vector comprising a fusion protein having a HOX oncoprotein and an estrogen receptor binding domain and cultured in the presence of an estrogen agonist and a combination of one or more multilineage and myeloid cytokines, where the cultured cell differentiates into a mature neutrophil, macrophage/dendritic, biphenotypic neutrophil/macrophage/dendritic, and/or multipotent neutrophil/macrophage/dendritic/eosinophil/mast cell after removal of the estrogen agonist.

Figure 4:
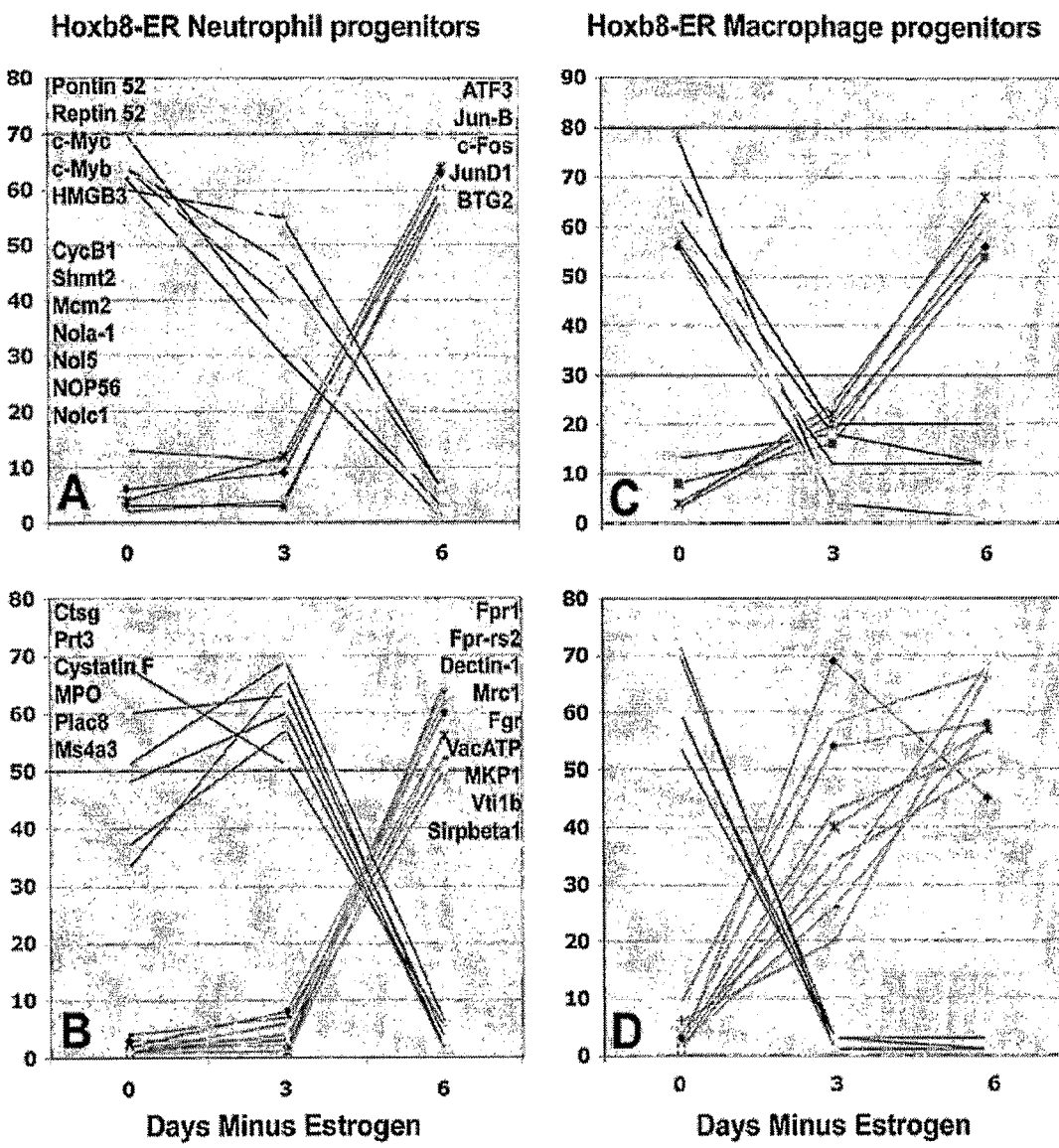
FIGS. 4A-4D demonstrate that a concerted program of phagocytic differentiation follows inactivation of Hoxb8-ER. Panels A and C: Down-regulation kinetics of c-Myb, c-Myc, Hmgb3, Pontin 52 and Reptin 52 (blue tracing) mirrors down-regulation of the cell cycle genes CycB1, Shmt2, Mcm2, Nola-1, Nol5, NOP56, and Nolc1 (described in Table 1) in both Hoxb8-ER SCF neutrophil progenitors (panel A) and Hoxb8-ER GM-CSF macrophage progenitors (panel C). In each case, up-regulation of the transcription factors ATF3, Jun-B, e-Fos, JunD1, and BTG2 (purple tracings) follows cell cycle arrest. Panels B and D: Down-regulation of the promyelocytic genes Ctsg, Prt3, Cystatin F, MPO, Plac8, and Ms4a3 (brown tracings) mirrors c-Myb downregulation, while up-regulation of the terminal differentiation genes Fpr1, Fpr-rs2, Dectin-1, Mrc1, Fgr, VacATP, MKP1, Vti1b, and Sirpbeta1 (green tracings) coincides with up-regulation of the leucine zipper transcription factors (purple tracings). The X-axis designates days post estrogen withdrawal, and the Y-axis designates relative expression level of mRNA, as measured by Affymetrix arrays.

Following oncoprotein inactivation the mature macrophage/dendritic cells can be activated by pro-inflammatory stimuli such as bacterial lipopolysaccharide (LPS). When activated, these mature macrophage/dendritic cells secrete the normal broad array of pro-inflammatory cytokines (FIG. 4, Table 4).

Figure 5:
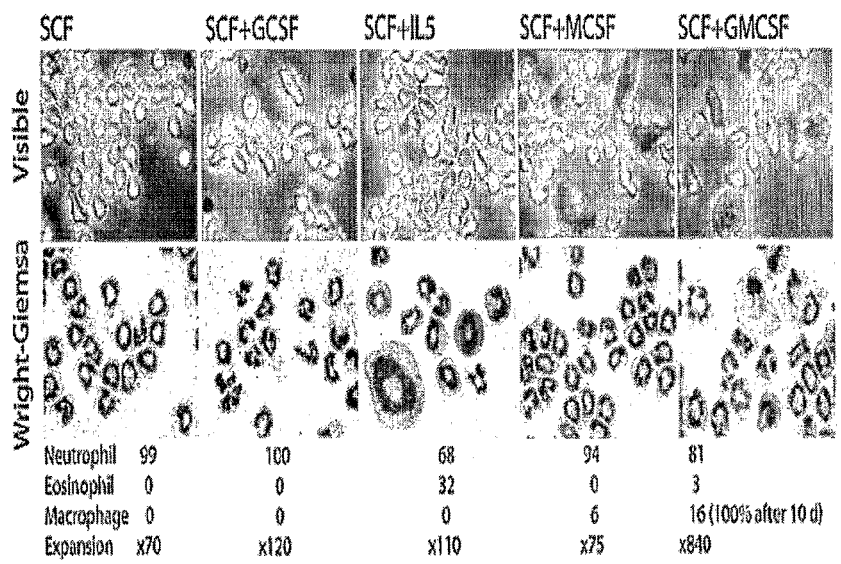
FIG. 5 demonstrates that Hoxb8-ER SCF progenitors behave as GMP, retaining an ability to differentiate into eosinophils and macrophages. Hoxb8-ER SCF progenitors were permitted to differentiate in SCF medium supplemented with the lineage-specific cytokines GCSF, IL5, MCSF, and GM-CSF, as indicated above the photographs. Cells were photographed 6 days after differentiation was initiated by removal of estradiol. In the column demarcated "SCF+IL5", a developing eosinophil is magnified at lower left. Distribution of mature cell types is indicated below each column, as measured at the end of the 6 day differentiation.

Using a different HOX oncoproteins (e.g., but not limited to, Hoxa9 and Hoxa7) fusion proteins were found to immortalize progenitors that are committed to principally to neutrophil differentiation. Half of the clones exhibited principally, but not exclusively, neutrophilic differentiation. Approximately one-third of clones exhibit exclusive or >95% differentiation to neutrophils. For example, for Hoxa9, the differentiation outcomes of analysis of 23 clones is listed in Table 5, and the morphology of representative clones committed to the neutrophil, macrophage, or bi-phenotypic (both neutrophils and macrophages) is represented in FIG. 5.

Figure 6:
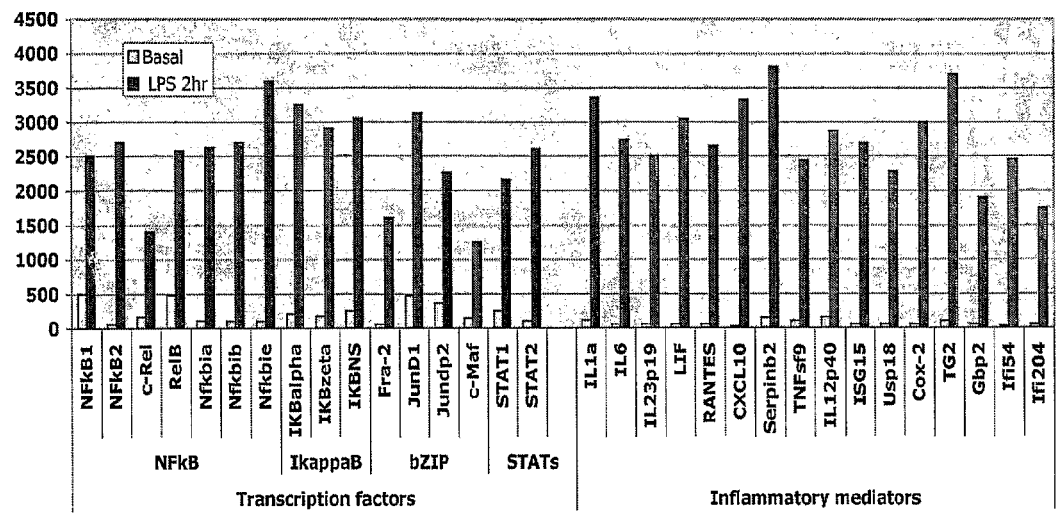
FIG. 6 shows that inflammatory signaling pathways are preserved in macrophages derived from Hoxb8-ER GM-CSF progenitors. LPS induces rapid activation of NfkB, IkB, bZIP, and STAT transcription factors in Hoxb8-ER-derived macrophages, as well as strong activation of the mediators of inflammation. Basal levels of mRNA are represented by the first bar, and LPS-induced levels (2 hour treatment) by the second bar of each set. mRNA levels are indicated on left and gene designations at the sides or beneath each panel.

These progenitors can be expanded indefinitely and differentiate into mature neutrophils following removal of estrogen (i.e., inactivation of HOX fusion protein), based on morphologic criteria. They exhibit normal morphologic differentiation, suggesting they have executed a normal genetic program of normal neutrophils. They die within 5 days of maturation, the same lifespan as normal neutrophils have in vivo. For example, using Affymetrix, for example, genomic arrays show that Hoxa9-ER progenitors down-regulate their cell-cycle within 48 hrs of estrogen withdrawal (FIG. 6), evidencing the same genomic fingerprint evidenced by progenitors immortalized by Hoxb8-ER. For example, genomic analysis over a shorter time-frame, examining changes after 24, 48, and 72 hours following estrogen withdrawal. It is evident that the process of downregulating cell division and executing the program of differentiation gene expression occurs rapidly, being significantly underway within 24 hours following estrogen withdrawal.

The Hoxb8-ER and Hoxa9-ER cell technology of the present invention forms a rapid and convenient means to study the role of the immune system in microbial pathogenesis or in inflammatory human diseases. The system is extremely cost-effective when considering the comparable costs involved in housing mice and deriving mature monocyte/dendritic cells or neutrophils from adult mice. The system eliminates the needless death of mice, and its use should be encouraged in all contexts of studying innate immunity and the role of macrophage/dendritic cells and neutrophils to the stimulation of the acquired immune system (B and T cells). Applying these systems to marrow from genetically modified (transgenic or gene knockout) mice provides a convenient system to delineate biochemical signaling pathways by reconstituting pathways with normal or mutant versions of the knockout cDNA, introduced into progenitors prior to their differentiation, and functionally assessed after maturation.

The invention also provides a system for the testing of various pharmacological compounds and therapeutic reagents for the treatment of disease. The ability of a therapeutic agent to promote differentiation induced by a variety of single oncoproteins in a defined background could only be studied using the system of the instant invention. Expression of a heterologous oncogenes in a cell line of the invention allows for the direct comparison of the efficacy of a single compound on cells with identical genetic backgrounds other than the single oncogene. Alternatively, a series of compounds can be tested on cells containing a defined genetic alteration to determine if they are capable of inducing differentiation.

In a related aspect, a method of treating an inflammatory disorder is provided including administering to a subject in need thereof a pharmaceutical composition comprising the isolated cells of the present invention and a pharmaceutically acceptable carrier.

The following examples are intended to illustrate but not limit the invention.

Example 1

Methods

Construction of Tagged, Estrogen Receptor Fusions of Hoxb8 and Hoxa9.

A murine stem cell provirus (Mscv) expressing Hoxb8-ER or Hoxa9-ER was generated by inserting estrogen-binding domain (ERBD) of estrogen receptor (ER) at an N-terminal MluI restriction site engineered into epitope-tagged murine Hoxb8 or Hoxa9 proteins. Tagged Hoxb8 was generated by PCR using the 5' primers (FLAG tag: g gaa ttc gcc acc ATG GAC TAC AAG GAC GAC GAT GAC AAA GGA ACG CGT GGA AGCTCTTATTTCGTCAACTCAC (SE ID NO:11); HA tag: g gaa ttc gcc acc ATG GGA TAC CCA TAC GAT GTT CCG GAT TAC GCT ACG CGT GGA AGCTCTTATTTCGTCAACTCAC (SEQ ID NO: 12)) and the common 3' primer: ccg ctc gag tta CTA CTTCTTGTCACCCTTCTGCG (SEQ ID NO: 13). Underlined sequences complement the 5' sense strand sequences for amino acid positions 2 to 7 and the 3' antisense strand sequences encoding the last 7 amino acids. Sequences encoding the Flag (DYKDDDDKG) (SEQ ID NO: 14) or HA (YPYDVPDYA) (SEQ ID NO: 15) tags are in italics. There is a unique EcoRI site (bold lower case) followed by canonical Kozac sequence (gcc ace) preceding the initiating ATG (first capitalized codon), and a unique XhoI site (bold lower case) after the stop codon (bold upper case). Following sequences encoding the tag (italics), there is a unique in-frame MluI site in each 5' PCR primer (bold upper case) as well as an additional GGA codon encoding glycine which could facilitate flexibility between the tag and Hox protein domains. This is an important consideration, because the N-terminal domain of Hox proteins is critical for their immortalizing function. In preparation for cloning, the PCR product was digested by EcoRI and XhoI, and ligated into the pMscvNeo proviral vector (Clontech). To generate ER fusions of Hoxb8, in-frame sequences encoding the estrogen-binding domain of the human estrogen receptor (residues 282 to 595; ERBD, see, e.g., SEQ ID NO: 10) containing a Gly400Val mutation were produced by PCR using primers containing in-frame MluI sequences at their 5' ends followed by digestion with MluI and ligation into the MluI site of each tagged Hoxb8 construct. The Gly400Val mutant ER was used because this point mutation renders the receptor insensitive to the low levels of estrogen found in fetal bovine serum (FBS) as well as to the estrogenic effects of other compounds, such as phenol red.

To generate conditional Hoxa9 proteins, codons encoding amino acids 4 to 5 of Hoxa9 were mutated into an MluI site in pGEM3zf-EE-Hoxa9 [Calvo, K. R., et al., Mol Cell Biol, 2000. 20 (9): p. 3274-85], and the same fragment encoding the mutant human ERBD described above was ligated into the Hoxa9 MluI site. The EE-ER-Hoxa9 coding sequence was excised by EcoRI and inserted into pMscvPuro (Clontech). All plasmids were sequenced over their cloning junctions to verify integrity.

Retrovirus preparation. Helper-free retrovirus was collected as culture supernatant following calcium phosphate cotransfection (Invitrogen, Carlsbad, Calif.) of 293T cells with MSCV tag-ER-Hox retroviral constructs and an ecotropic packaging construct.

Producing Retrovirus by CaPO4 Transfection of 293T Cells.

Helper-free retrovirus is produced in 293T cells by $CaPO_4$ co-transfection of the retroviral construct with an ecotropic or amphotropic packaging construct (CellGenesys), using Invitrogen's $CaPO_4$ Transfection Kit (#44-0052).

At day 0, $2\times10^6$ 293T were seeded cells into a 10 cm dish with 10 ml DMEM (High glucose)+10% FBS+penicillin/streptomycin/glutamine. At day 1, the media was removed and replaced with 10 ml of fresh, pre-warmed media. Cells should be at ~60-70% confluence. 10 μg of retroviral construct+10 μg of packaging construct as per protocol was used to transfect the cells, and the cells were incubated overnight.

At day 2, media was removed and replaced with 6 ml of fresh, pre-warmed media. At day 3 6 ml of virus was harvested to a 15 ml conical tube. The tube was centrifuged briefly to pellet all cell debris. 1-2 ml aliquots were frozen in 2 ml freezing tubes and stored at –80° C.

Alternatively, the virus supernatant can be filtered and used immediately, where another 6 ml of fresh, pre-warmed media was added to transfected cells.

Depending on the size of the insert, viral titers between $10^5$-$10^6$/ml are routinely obtained.

Spin Infection Protocol—for Infection in 12-Well Plates.

A non-TC treated plate was coated with Fibronectin (Falcon, 12-well #351153 or 6-well #351146) supplied as a 1 mg/ml solution from Sigma (F-0895). The fibronectin was diluted 1:100 in PBS to a final 10 μg/ml solution, 1 ml of the solution was aliquoted into each well of a 12-well non-tissue treated plate (or 2 ml per well in a 6-well plate), and the plates were incubated at 37° for 1-4 hrs or at 4° overnight.

Cells were counted and resuspend at $10^5$-$10^6$/ml in "Progenitor Outgrowth Medium" (OptiMem 10% FBS 1% PSG, 10 ng/ml stem cell factor or 1% culture supernatant from an SCF-producing cell line 30 uM beta mercapto ethanol (1 ul neat into 500 mls medium) 1 uM estradiol). 1 μl of Lipofectamine was added per ml of cells. The fibronectin was aspirated and 250 μl (~25,000 to 250,000 cells) were aliquoted into each well. 1-2 ml of virus were added to each well of the 12-well plate. The final Lipofectamine concentration was $1\times$ (1:1000).

Spinoculation.

The plate(s) were wrapped in Saran Wrap with an equivalent balance plate, the plates were then spun in plate carriers at 1500 g for 60-90 minutes at 22°-32° in a Gernot Walter's Beckman JS5.2 rotor at 2800 rpm (r=20 cm, ~1300 g). The Lipofectamine/Polybrene was diluted with 3 ml of fresh "Progenitor Outgrowth Media" and the cells were incubated at 37° C.

Progenitor Outgrowth Medium.

Virus was stored at –80° C. after filtration through a 0.45 μM membrane. Virus titers ranged from $10^5$ to $10^6$, as calculated by the outgrowth of G418-resistant clones on NIH3T3 fibroblasts.

Cytokine Pre-Stimulation of the Cells.

For a good retroviral infection, the cells must be actively cycling. Therefore, the cells from either negatively-selected progenitors, some of which may be quiescent in marrow, should be transferred to a cytokine-rich media for 2 days. Stem Cell Media (IMDM (Iscove's)+15% FBS+1% pen/strep/glutamine, 10 ng/ml murine IL-3 (5 ng/ml) 20 ng/ml murine IL-6 25 ng/ml murine SCF (up to 100 ng/ml)) is very effective, however, other media is equally effective, especially those that include G-CSF, Flt3-ligand, and the like.

Derivation of Neutrophil Progenitors.

Derivation of neutrophil progenitors is dependent upon the cytokine conditions used during pre-expansion of target stem cells and during selection of immortalized progenitors following infection with Hoxb8-ER retrovirus. Bone marrow was harvested from the femur and tibia of female Balb/c mice, as described. Lineage-negative progenitors obtained by negative selection using an antibody cocktail reactive against MacI, B220, and Thy1.2 followed by removal of lin+ cells on a magnetic column (Stemcell Technologies, Vancouver, BC, Canada). Progenitors were pre-stimulated for 48 hours in Iscoves modified Dulbecco medium (IMDM) containing 15% FBS, 1% PSE, 50 ng/mL stem cell factor (SCF), 25 ng/mL IL-3, and 25 ng/mL IL-6 (also in Methods Supplement 4). 25,000 marrow progenitors were infected with 1 mL ER-Hoxb8 retrovirus by spinoculation (2,500 g, 2 hours, 22° C.) in the presence of lipofectamine (1:1000, Gibco BRL), as described. Infected progenitors were cultured in OptiMem medium containing 10% FBS, 1% PSE, 10 ng/ml SCF, 30 uM beta mercaptoethanol (1 ul into 500 mls medium), and 1 uM β-estradiol (Sigma). An infection efficiency of 10% was approximated based on comparison of the initial rates of progenitor outgrowth in the presence or absence of G418 selection. Immortalized myeloid progenitors were enriched by the serial passage of non-adherent cells every 3 days into new 12-well tissue culture plates. Immortalized progenitors predominated cultures infected by Hox-ER retroviruses by day 14, while control cultures evidenced reduce proliferation and stopped dividing by day 21. ER-Hox proteins continued to divide with a generation time of 18-20 hours. Recombinant SCF was replace by a 1% culture supernatant (approximately 10 ng/ml) from an SCF-producing cell line immediately following infection with Hoxb8-ER retrovirus. SCF-dependent Hoxb8-ER progenitors have proliferated over 9 months, maintaining a normal 40, XX karyotype in 19 of 20 chromosome spreads in an analysis done after 8 months (analysis for Hoxb8-ER macrophage progenitors is illustrated in FIG. 1).

Derivation of Macrophage Progenitors.

Harvesting Marrow.

Female Balb/c mice were sacrificed (generally 8-12 weeks) and intact femurs and tibia were removed into sterile dishes of PBS on ice. The ends of the bones were cut off and 10 ml syringes (filled with RPMI 10%) and 25 G needles were used to shoot the marrow into 50 ml conical tubes. The tubes were topped off up at 50 ml with PBS and the cells pelleted. The cells were resuspended in 10 ml ACK red blood cell lysis buffer (150 mM $NH_4Cl$ 10 mM $KHCO_3$ 0.1 mM $Na_2EDTA$ Adjust to pH 7.2-7.4 with 1N HCl Filter sterilize and store at 4° C.), followed by incubation for 5 min at RT. The tube was topped off at 50 ml with PBS and the cells are pelleted. The cells are finally resuspended in 4 ml of PBS.

Harvesting Fetal Liver Cells.

Pregnant mice were sacrificed, and subsequently, embryos were removed (can be used as early as day 11). Using a plunger from a 5 ml syringe, the cells are dispersed through a 70μ cell strainer (Falcon #352350) and pelleted. Pelleted cells are resuspended in 10 ml of ACK red blood cell lysis buffer and subsequently incubated 5 min at RT. 50 ml centrifuge tubes are Topped off at 50 ml with PBS and the cells are pelleted. Pelleted cells are rinsed $1\times$ in PBS, and resuspended in 4 ml of PBS.

Using 5-Flurouracil Prior to Isolation of Marrow and Progenitors.

Mice can be injected with 5-Flurouracil (5-FU) 3-5 days prior to harvesting the bone marrow. Injections are done at 100-150 mg/kg I.P. The 5-FU reduces the total cellularity of the marrow with an increased % of progenitors. The advantage of the 5-FU is that the marrow from more mice can be processed on the same Ficoll gradient and on the same Stem-Cell Technology column (using less reagent).

Bone marrow was isolated from the femurs of mice following ammonium sulfate lysis of red cells and centrifugation onto a cushion of Ficoll-Paque (Pharmacia, Piscataway, N.J.) as described. 100,000 Ficoll-purified mononuclear cells were subjected to spinoculation with one ml of Hoxb8-ER or Hoxa9-ER retrovirus. Infected progenitors were cultured in "Myeloid Cell Medium" (RPMI 1640 with 10% FBS, 1% Pen-Strep-Glut (PSQ, Gibco BRL, Rockville, Md.), 1% GM-CSF-conditioned media from B16 melanoma expressing the GM-CSF cDNA (approximately 10 ng/mL GM-CSF) and 1 uM β-estradiol (Sigma)). β-estradiol was kept as 1,000× (1 mM) or 10,000× (10 mM) stocks in 100% ethanol and stored at −20° C. An infection efficiency of 10% was approximated based on comparison of rates of progenitor outgrowth in the presence or absence of G418, which selects for expression of the neomycine phosphotransferase gene encoded by the MSCV retroviral vector.

Purifying early progenitors using Ficoll-Hypaque centrifugation for derivation of macrophage-committed progenitors immortalized by Hoxb8-ER or biphenotypic, neutrophil, or macrophage progenitors immortalized by Hoxa9-ER.

In a 15 ml conical tube, 3 ml of room-temperature Ficoll-Paque (Pharmacia, Piscataway, N.J.) was added and 4 ml of total marrow cells in PBS was gently layered on top. The cells were spun for 30 minutes at 1500 rpm at 20° in a Sorvall 6000B rotor (450 g). The cells were harvested from the interface and all supernatant within ~0.5 ml of the pellet were collected. The collected supernatant was diluted to 50 ml in Myeloid Medium (RPMI 1640 \10% FBS, 1% Pen-Strep-Glut (PSQ, Gibco BRL, Rockville, Md.), 20 ng/ml GMCSF or 1% culture supernatant from a GM-CSF-producing cell line and 1 uM β-estradiol (Sigma)). The cells were subsequently pelleted and counted.

Figure 8:
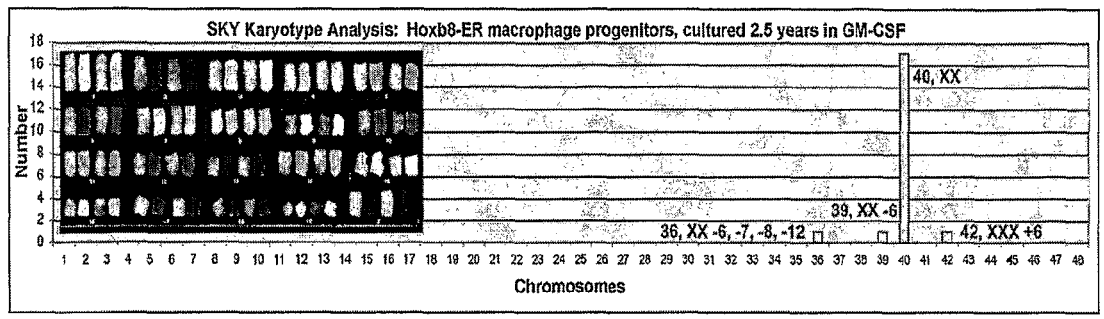
FIG. 8 shows a SKY karyotype analysis of Hoxb8-ER macrophage progenitors. The karyotype of 20 cells was analyzed and the frequency of cells plotted as a function of their chromosome number. 17 cells exhibit the normal 40, XX karyotype and 3 cells exhibited abnormal karyotypes, listed adjacent to their histogram bars. A typical analysis is inset at left.

Immortalized myeloid progenitors were selected by removal of non-adherent progenitor cells every 3 days to a new well in a 6-well culture plate. This protocol was continued over 3 weeks, at which time cultures contained immortalized macrophage progenitors (detailed protocol in Methods Supplement 7). Selection for G418 resistance permitted derivation of immortalized progenitors in a shorter timeframe (10 to 14 days). Eleven lines were derived from Black/6 and Balb-c mice using this protocol and each differentiated quantitatively into macrophages. Differentiation to macrophages is achieved by removal of estrogen with continued culture in the same medium. Macrophage chromosome analysis using chromosome painting demonstrated that greater than 85% of progenitors exhibited a normal karyotype (FIG. 8). Cells were maintained in a 37° C. humidified incubator with 5% CO2. Progenitors can be store in liquid nitrogen.

Cell Culture.

Cell lines 293T, Nalm6, 3T3 and cytokine-producing cell lines (for SCF and GM-SCF) were cultured and maintained as previously described [Calvo et al., (2000), Sykes, D. B. and M. P. Kamps, Mol Cell Biol, 2004. 24 (3): p. 1256-69].

Luciferase Reporter Assay.

Estradiol-responsiveness was evaluated by the ability of Hox-ER and activated form of E2a-Pbx1 (or Vp16-Pbx1) to induce cooperative activation of a luciferase reporter gene driven by tandem repeats of TGAT-TTAT motifs in Nalm6 (for Hoxa9-ER) or 293T (for Hoxb8-ER) cells cultured in medium supplemented with a wide range of concentration of β-estradiol (10-11M to 10-5 M), as previously described [Calvo et al., (2000), Sykes and Kamps (2001)]. Transcription activation was calculated as the value of relative light units for firefly luciferase versus that for a control *renilla* luciferase construct that was cotransfected in all samples.

Spectral Karyotyping (SKY) Analysis.

SKY analysis of myeloid progenitors were performed as previously described [Yang, A. H., et al., J Neurosci, 2003. 23 (32): p. 10454-62].

Western Blot and Northern Blot.

Antibodies α-Hoxa9, α-Flag, α-HA, α-RelB, α-c-Jun, α-p65, α-p38, and a-SRC-A were used for western blot as previously described [Calvo et al., (2000), Sykes and Kamps (2001), Wang, G. G., M. P. Pasillas, and M. P. Kamps, Blood, 2005, Park, J. M., et al., Immunity, 2005. 23 (3): p. 319-29]. Northern blot was performed as described previously [Sykes, D. B. and M. P. Kamps, Leuk Lymphoma, 2003. 44 (7): p. 1131-9].

Affymetrix Array Analysis.

Gene expression profiling analysis was performed and analyzed using affymetrix mouse total genome array as previously described [Wang et al., (2005)].

Flow Cytometric Analysis (FACS), Wright-Giemsa Staining, Nitroblue Tetrazolium Reduction Assay (NBT) & Nonspecific Esterase Assay (NSE).

Phenotypic characterization of myeloid progenitors and differentiated cells analyzed by FACS, Wright-Giemsa staining, and use of the NBT and NSE assays was performed as described previously [Sykes and Kamps (2001)].

ER fusions of Hoxb8 and Hoxa9 exhibit estrogen-regulated transcriptional function. The estrogen-binding domain of the estrogen receptor (ER) was fused to the N-terminus of Hoxb8 and Hoxa9, and the fusion cDNA's expressed in the retroviral vector MSCV (FIG. 1A). N-terminal epitope tags were added to facilitate subsequent identification. While Hoxa9 nor Hoxb8 exhibit independent transcriptional activation through their TAAT or TTAT DNA recognition motifs, both heterodimerize with Pbx on the composite TGAT-TTAT Pbx-Hox motif, and their binding to DNA can be measured indirectly through their ability to cooperate with a transcriptionally activated forms of Pbx (oncoprotein E2a-Pbx1) to activate transcription of a reporter driven by TGAT-TTAT elements. Using this assay, ER-Hoxa9 and ER-Hoxb8 co-activated transcription 10- and 3-fold, respectively, in response to β-estradiol. Half-maximal activation occurred at 10 nM β-estradiol (FIG. 1B). Therefore, Hoxb8-ER and Hoxa9-ER exhibit estradiol-regulated access to DNA.

Hoxb8-ER immortalizes neutrophil-committed or monocyte-committed progenitors, which can be selected based on their cytokine-dependent properties. In the presence of 1 uM estradiol, infection of primary marrow cultured in interleukin 3 (IL3), stem cell factor (SCF), or granulocyte-macrophage colony-stimulating factor (GM-CSF) with retrovirus expressing Hoxb8-ER or Hoxa9-ER resulted in production of immortalized factor-dependent progenitors (FIG. 1C; ER fusion proteins identified by Western blotting in insert), while infection in the presence of granulocyte colony stimulating factor (G-CSF) or macrophage colony stimulating factor (M-CSF) did not. The lineage-commitment of immortalized progenitors was tested by observing cell fate after withdrawal of estradiol. SCF-dependent Hoxb8-ER progenitors differentiated into 99% neutrophils (1% mast cells) while GM-CSF-dependent Hoxb8-ER progenitors differentiated to macrophages at levels >99% (FIG. 2A). By contrast, Hoxa9-ER progenitors exhibited principally biphenotypic neutrophil/macrophage differentiation regardless of the cytokine that was used during their derivation. After cloning, 20% of clones executed neutrophil-restricted differentiation and rare clones (1 in 30) executed macrophage-restricted differentiation. Because the use of Hoxb8-ER obviated the need for cloning, characterization of the Hoxb8-ER-immortalized progenitors was pursued.

Neutrophil or macrophage progenitors immortalized by Hoxb8-ER were next characterized for surface antigens and enzyme activities characteristic of neutrophils or macrophages. Neutrophils produced by differentiation of SCF-dependent Hoxb8-ER progenitors up-regulated NADPH oxidase (FIG. 2A), the neutrophil surface antigen Gr-1 and the myeloid integrin Mac-1, and down-regulated the macrophage marker F4/80 (FIG. 2B). By contrast, macrophages produced by differentiation of GM-CSF-dependent Hoxb8-ER macrophage progenitors exhibited activation of macrophage non-specific esterase (FIG. 2A), up-regulation of F4/80 and Mac1, and down-regulation of Gr-1 (FIG. 2B).

Hoxb8-ER SCF neutrophil progenitors have proliferated continuously for 8 months with a cell division time of approximately 21 hours and Hoxb8-ER GM-CSF have a generation time of approximately 23 hours. Throughout this time-frame, progenitors exhibited stable karyotypes and differentiation responses. 19 of 20 metaphase spreads from neutrophil progenitors cultivated for 8 months yielded a normal karyotype (40, XX) (FIG. 8). Therefore, Hoxb8-ER progenitors do not become aneuploidy as a requirement for immortalization, they do not become aneuploidy at a significant rate over long durations of passage, and there is no selection for karyotypically abnormal cells. Progenitors also retained stable differentiation phenotype. Hoxb8-ER SCF progenitors have differentiated quantitatively into neutrophils for 8 months. In one testing (8 months) one of two lines yielded 5% adherent monocytes following differentiation.

Transcription profiling defines the differentiation program and the mature characteristics of neutrophil and macrophage progenitors immortalized by Hoxb8-ER. Affymetrix genome arrays (430 2.0 Array; probe sets for 39,000 transcripts including over 34,000 for characterized mouse genes) were interrogated with RNA from SCF Hoxb8-ER progenitors undergoing neutrophil differentiation and from GM-CSF Hoxb8-ER progenitors undergoing macrophage differentiation (Summary in Table 1; Down-regulated genes in Table 2, up-regulated genes in Table 3, LPS-induced genes in Table 4).

TABLE 1

Expression of diagnostic myeloid and cell cycle genes in SCF Hoxb8-ER neutrophil differentiation and in GM-CSF Hoxb8-ER macrophage differentiation

| Gene | Comment | Neutrophil Prog | Diff | Macrophage Prog | Diff | Genbank |
|---|---|---|---|---|---|---|
| Myeloid lineage markers (unchanged) | | | | | | |
| Fcgr2b | IgG Fc gamma receptor 2 beta, low affinity | 32 | 34 | 34 | 52 | BM224327 |
| Fcgr3 | IgG Fc gamma receptor 3, low affinity | 38 | 38 | 32 | 58 | NM_010188 |
| CCR2 | Receptor for macrophage chemotactic protein (MCP1) | 138 | 62 | 84 | 192 | U47035 |
| Fcer1g | IgE Fc receptor 1 gamma, high affinity | 32 | 30 | 44 | 103 | NM_010185 |
| Neutrophil markers up-regulated | | | | | | |
| IL8Rbeta | IL8 Receptor beta, neutrophil chemokine receptor | <1 | 94 | <1 | <1 | NM_009909 |
| LF | Lactoferrin | <1 | 138 | <1 | <1 | NM_008522 |
| LRG1 | Leucine-rich alpha-2-glycoprotein, granulocyte marker of unknown function | <1 | 50 | 2 | 1 | NM_029796 |
| NB-1 | CD177, Neutrophil marker of unknown function | <1 | 22 | 1 | <1 | BC027283 |
| Cnlp | Cathelin, anti-bacterial peptide | 4 | 56 | <1 | <1 | NM_009921 |
| Lip2 | Lipocalin 2. Neutrophil granual protein. Function unknown. | 3 | 62 | 3 | 5 | X14607 |
| Itgb2l | Integrin beta 2-like. Neutrophil granual protein released on activation. Function unknown. | <1 | 75 | <1 | <1 | NM_008405 |
| MMP9 | Neutrophil gelatinase, Gelatinase B | <1 | 104 | <1 | 9 | NM_013599 |
| Pglyrp1 | Peptidoglycan recognition protein 1. In neutrophil granulas in traps. Hydrolyzes peptidoglycan. | 4 | 140 | 8 | 8 | NM_009402 |
| Stefin A1 | Cystein proteinase inhibitor. Aka Cathepsin, Stefin 3, Cystatin A | 4 | 214 | 2 | 11 | AW146083 |
| Arginase 1 | Arginase 1, inflammation modulation. Hydrolysis of L-arginine into ornithine. | <1 | 330 | <1 | <1 | NM_007482 |
| Ceacam1 | CEA-related cell adhesion molecule 1. Expressed on leukocytes, epithelia, and endothelia mediates homophilic cell adhesion. Promotes motility. Matrix-dependent binding to talin. Carcinoembryonic antigen-related cell adhesion molecule 1 (CEACAM1) is expressed on epithelia, blood vessel endothelia, and leukocytes. A variety of physiological functions have been assigned to CEACAM1. It is involved in the formation of glands and blood vessels, in immune reactions, and in the regulation of tumor growth. As a homophilic and heterophilic adhesion receptor, it signals through different cellular pathways. CEACAM1 is a tumor suppressor whose expression is known to be lost in the great majority of early adenomas and carcinomas. CEACAM1 and alpha(v)beta(3) integrin are functionally interconnected with respect to the invasive growth of melanomas. Can bind SHP1 and SHP2 and suppress activation in T cells. | 3 | 41 | 4 | 6 | BC016891 |
| Ceacam10 | CEA-related cell adhesion molecule 10. Highly related to Ceacam1. Expressed in placenta, colon, marrow. | <1 | 160 | <1 | 1 | NM_007675 |

TABLE 1-continued

Expression of diagnostic myeloid and cell cycle genes in SCF Hoxb8-ER neutrophil differentiation and in GM-CSF Hoxb8-ER macrophage differentiation

| Gene | Comment | Neutrophil Prog | Diff | Macrophage Prog | Diff | Genbank |
|---|---|---|---|---|---|---|
| Olfactomedian 4 | Secreted neutrophil glycoprotein. Aka pDP4. Function unknown. | <1 | 112 | 8 | 6 | AV290148 |
| Monocyte markers up-regulated | | | | | | |
| ICSBP/IRF-8 | Interferon Consensus Sequence binding protein. Macrophage commitment transcription factor | 4 | <1 | 18 | 16 | NM_008320 |
| MMP12 | Macrophage elastase, Matrix metalloproteinase 12. | <1 | 8 | 36 | 196 | NM_008605 |
| Macrosialin | CD68, Class D scavenger receptor | 6 | 5 | 26 | 120 | BC021637 |
| Dectin-2beta | Dendritic cell C-type lectin, Clecsf10. Marker of inflammatory monocytes. Function unknown. | <1 | <1 | 72 | 360 | NM_020001 |
| CD11c | Integrin alpha X, ItgaX, Dendritic marker | <1 | 5 | 14 | 117 | NM_021334 |
| Msr1 | Macrophage scavenger receptor 1 (SR-A) | <1 | <1 | 3 | 30 | NM_031195 |
| Msr2 | Macrophage scavenger receptor 2 | <1 | <1 | <1 | 32 | BC016551 |
| mMGL2 | Macrophage galactose N-acetyl-galactosamine specific lectin | <1 | 7 | 12 | 132 | AW494220 |
| CCL17 | CCR4 ligand, T cell chemokine produced by macrophages | <1 | <1 | 5 | 48 | NM_011332 |
| CCL22 | CCR4 ligand, T cell chemokine produced by macrophages | <1 | <1 | <1 | 17 | BC012658 |
| Plet1 | Unknown function, 285aa | <1 | <1 | 4 | 116 | BC022950 |
| Myeloid differentiation markers up-regulated in both neutrophils and monocytes | | | | | | |
| Fpr1 | Formyl peptide receptor 1 | <1 | 86 | <1 | 30 | NM_013521 |
| Fpr-rs2 | Formyl peptide receptor-related sequence 2 | 1 | 104 | 4 | 118 | NM_008039 |
| Dectin-1 | Clecsf12, beta glucan receptor, fungal recognition | 4 | 278 | 20 | 147 | NM_020008 |
| CD300lf | CD300-like factor, Pigr3, CLIM1, Polymeric Ig Receptor III | <1 | 260 | 5 | 35 | BM230330 |
| Mrc1 | Mannose receptor. Binds bacterial C-terminal mannose | <1 | 80 | 13 | 226 | NM_008625 |
| TLR2 | Toll-like receptor 2 | <1 | 28 | 10 | 25 | NM_011905 |
| CD14 | TLR coreceptor | 6 | 92 | 40 | 136 | NM_009841 |
| MMP8 | Matrix metalloproteinase 8 | 6 | 154 | 74 | 154 | NM_008611 |
| Mac1 | CD11b/Integrin alpha M/CD18 | <1 | 24 | 9 | 48 | NM_008401 |
| Fgr | Src-family myeloid tyrosine protein kinase | <1 | 36 | 2 | 52 | NM_010208 |
| Lgmn | Legumain. Specific protease. Activates cathepsins B, H, L | <1 | 29 | 1 | 65 | NM_011175 |
| SHPS-1 | Adhesion receptor coupled to SHP-2. Cytoskeleton reorganization. Apoptotic cell engulfment | 6 | 63 | 17 | 128 | |
| Sirpbeta1 | Receptor. Activates macrophage/MAP kinase. Promotes phagocytosis. Binds DAP12 | <1 | 140 | 4 | 82 | AI662854 |
| Vti1b | Vesicle transport through interaction with tSNAREs, facilitates exocytosis | <1 | 54 | <1 | 26 | AV002218 |
| MKP1/dusp1 | Ptpn16. Inactivates Jun. Prevents re-entry into cell cycle. Negative regulator of inflammation. | 7 | 109 | 5 | 114 | NM_013642 |
| Myeloid differentiation markers down-regulated in both neutrophils and monocytes | | | | | | |
| MPO | Myeloperoxidase. In azurophilic (primary) granuals | 340 | 4 | 240 | <1 | NM_010824 |
| Prtn3 | Proteinase 3, myeloblastin, serine proteinase, in azurophilic (primary) granuals | 294 | 4 | 400 | 2 | U97073 |
| Ela2 | Elastase 2, Neutrophil elastase, serine proteinase | 20 | <1 | 300 | <1 | NM_015779 |
| Cnn3 | Calponin 3, actin-binding protein | 136 | 3 | 46 | <1 | BB724741 |
| Nedd4 | Ubiquitination regulation. Developmentally regulated. | 110 | 12 | 9 | <1 | NM_010890 |
| Plac8 | Placental 8, unknown function | 240 | 4 | 180 | 1 | AF263458 |
| Ms4a3 | Membrane-spanning 4-domains A3, HTm4, unknown function | 56 | 3 | 144 | 3 | NM_133246 |
| Common myeloid differentiation markers upregulated in SCF Hoxb8-ER neutrophil progenitors and expressed persistantly in GM-CSF Hoxb8-ER progenitors | | | | | | |
| Lyzs | Lysozyme | 6 | 260 | 200 | 380 | AW208566 |
| Gsn | Gelsolin, involved in podosome formation | 2 | 30 | 74 | 80 | NM_010354 |
| CD14 | TLR coreceptor | 5 | 40 | 40 | 136 | NM_009841 |
| Lilrb4 | Leukocyte Ig-like inhibitory receptor B4 | <1 | 54 | 30 | 121 | U05264 |
| Pira1 | Paired-Ig-like activating receptor A1, binds FcRgamma | <1 | 24 | 34 | 58 | NM_011087 |
| Pira6 | Paired-Ig-like activating receptor A6, binds FcRgamma | <1 | 14 | 44 | 86 | NM_011093 |
| Pilrb1 | Paired-Ig-like type II activating receptor beta | 2 | 158 | 24 | 90 | NM_133209 |
| Gp49b1 | Ig inhibitory receptor | <1 | 54 | 30 | 120 | NM_013532 |
| DC-HIL | Dendritic cell transmembrane protein, adhesion, binds RGD/proteoglycans | 4 | 104 | 108 | 266 | NM_053110 |

TABLE 1-continued

Expression of diagnostic myeloid and cell cycle genes in SCF Hoxb8-ER neutrophil differentiation and in GM-CSF Hoxb8-ER macrophage differentiation

| Gene | Comment | Neutrophil Prog | Diff | Macrophage Prog | Diff | Genbank |
|---|---|---|---|---|---|---|
| Progenitor Genes correlating with high expansion potential of SCF Hoxb8 neutrophil progenitors | | | | | | |
| Sox4 | HMG protein, oncoprotein | 32 | <1 | <1 | <1 | NM_009238 |
| HMG14 | HMGN1, High mobility group protein 14 | 94 | 6 | <1 | <1 | NM_008251 |
| HMGa2 | High mobility group protein a2 | 44 | 6 | <1 | <1 | NM_010441 |
| Transcription factors up-regulated | | | | | | |
| c-fos | FBJ osteosarcoma proto-oncogene, bZIP transcription factor | 8 | 116 | 12 | 256 | NM_010234 |
| c-Jun | bZIP transcription factor | 2 | 40 | 2 | 13 | BC002081 |
| ATF3 | c-jun-related bZIP transcription factor | <1 | 32 | 3 | 56 | NM_007498 |
| JunD1 | Jun family member D, bZIP transcription factor | 9 | 168 | 22 | 100 | NM_010592 |
| JunB | Jun family member B, bZIP transcription factor | 16 | 80 | 8 | 54 | NM_008416 |
| CEBP beta | upregulated in myeloid differentiation | 14 | 102 | 82 | 136 | NM_009883 |
| Btg2 | B-cell translocation gene 2. Downregulates Cyclin D1 and cell cycle. Promotes differentiation. | 3 | 52 | 12 | 200 | BG965405 |
| Mad | Max dimerization protein | 4 | 88 | 7 | 15 | BB036846 |
| Transcription factors down-regulated | | | | | | |
| c-Myc | Myelocytomatosis proto-oncogene | 88 | <1 | 37 | 3 | BC006728 |
| Pontin52, Tip49, Ruvb1 | Tip 49, Helicase, binds TATA-binding protein, Myc, E2F, and b-catenin activation complexes | 30 | <1 | 14 | 4 | NM_019685 |
| Reptin52, Tip48, Ruvb2 | Tip 48, Helicase, transcription regulation | 43 | 3 | 29 | 6 | NM_011304 |
| c-Myb | Myelocytomatosis proto-oncogene | 5 | 1 | 156 | <1 | NM_033597 |
| B-Myb | Myb-like 2, regulates cell cycle via E2F-binding protein p107, maintains ES cell stem-likeness | 8 | <1 | 14 | <1 | NM_008652 |
| Rbb4 | Retinoblastoma binding protein 4 | 62 | <1 | 36 | 10 | BF011461 |
| Hmgb3/Hmg4 | High mobility group member b3, Embryonic expression, hemopoietic stem cells, inhibits dif. | 72 | 4 | 12 | 2 | NM_008253 |
| TSC22d1 | Tgfb1i4, Growth factor inducible, HLH transcription factor | 44 | 2 | 96 | 9 | AU016382 |
| Cell division genes down-regulated | | | | | | |
| cycB1 | cyclin B1, binds cdk1/cdc2, G2/M progression | 40 | <1 | 18 | 3 | X58708 |
| Shmt2 | Serine hydroxymethyltransferase. Nucleotide biosynthesis | 21 | <1 | 37 | 4 | BM222403 |
| Rrm2 | Ribonucleotide reductase m2. Nucleotide biosynthesis | 46 | <1 | 52 | 4 | NM_009104 |
| mcm2-G1/S peak | Mini chromosome maintenance deficient 2-DNA replication licensing helicase | 84 | 2 | 38 | <1 | NM_008564 |
| cdc6-G1/S peak | Cell division cycle 6 (loads MCM7), licensing factor. DNA replication | 40 | 7 | 12 | <1 | NM_011799 |
| CDT1 | DNA replication licensing--loads mcm2-7. Oncoprotein in 3T3 | 27 | 8 | 60 | 8 | AF477481 |
| Nola1 | Nucleolar protein family A, member 1, snRNP. RNA maturation. | 32 | 10 | 30 | <1 | NM_026578 |
| Nol5 | Nucleolar protein 5, Nop5. RNA maturation. | 44 | <1 | 24 | <1 | BB729616 |
| U50snoRNA | mU50, snoRNA. RNA maturation. | 42 | 4 | 23 | <1 | AK012825 |
| NOP56 | Nucleolar protein 56. RNA maturation, ribosome Biogenesis. | 66 | 6 | 28 | 1 | BM249243 |
| Nolc1 | Nucleolar and coiled body phosphoprotein 1. RNA maturation, ribosome Biogenesis | 22 | <1 | 24 | 2 | BM236574 |
| SET | PP2A inhibitor. High in cancer/regenerating cells. Early development. translocated in leukemia | 104 | 15 | 72 | 6 | BF134272 |

TABLE 2

Gene down-regulation in SCF Hoxb8-ER neutrophil progenitors and in GM-CSF Hoxb8-ER macrophage progenitors

| Gene | Comment | Neut Prog 0 | 6d | Mac Prog 0 | 6d | Genbank |
|---|---|---|---|---|---|---|
| Cell cycle genes | | | | | | |
| cycB1 | cyclin B1, binds cdk1/cdc2, G2/M progression | 40 | <1 | 18 | 130 | X58708 |

TABLE 2-continued

Gene down-regulation in SCF Hoxb8-ER neutrophil progenitors and in GM-CSF Hoxb8-ER macrophage progenitors

| Gene | Comment | Neut Prog 0 | Neut Prog 6d | Mac Prog 0 | Mac Prog 6d | Genbank |
|---|---|---|---|---|---|---|
| Cenph | Centromere protein H | 14 | 2 | 8 | <1 | NM_021886 |
| Wee-1 | Inhibits cdk1 | 10 | <1 | 12 | 2 | BC006852 |
| ARD1 homologue | N-acetyltransferase (maintains HIF1a instability) | 20 | 5 | 14 | 3 | NM_019870 |
| Cdc20 | Promotes cyclin B ubiquitination and degradation (M phase arrest) | 42 | 20 | 60 | 12 | BB041150 |
| Cyclin B1-related | cyclin-D dependent kinase 4, c-Myc target gene | 48 | 6 | 60 | 17 | NM_007629 |
| cdk4 | | 25 | 6 | 13 | 4 | NM_009870 |
| cycD2 | | 46 | 1 | 8 | 7 | NM_009829 |
| Nucleotide biosynthesis | | | | | | |
| Apex | Apurinicapyrimidinic endonuclease | 32 | 6 | 30 | 3 | AV263745 |
| Shmt2 | Serine hydroxymethyltransferase | 21 | <1 | 37 | 4 | BM222403 |
| PRAT | Phosphoribosyl pyrophosphate amidotransferase | 33 | 2 | 8 | <1 | BG064988 |
| Rrm2 | Ribonucleotide reductase m2 | 46 | <1 | 52 | 4 | NM_009104 |
| Tmk | Thymidylate kinase | 52 | 10 | 27 | 3 | NM_023136 |
| Prps1 | Phosphoribosyl pyrophosphate synthetase 1 | 28 | 2 | 12 | 3 | NM_021463 |
| Gart | Phosphoribosylglycinamide formyltransferase | 19 | 6 | 40 | 10 | NM_010256 |
| Impdh2 | inosine 5-phosphate dehydrogenase 2, rate-limiting step in guanosine biosynthesis | 106 | 3 | 40 | 4 | NM_011830 |
| DNA replication | | | | | | |
| mcm2-G1/S peak | Mini chromosome maintenance deficient 2-replication licensing helicase | 84 | 2 | 38 | <1 | NM_008564 |
| Srm | Spermidine synthase | 48 | 2 | 52 | 2 | NM_009272 |
| dUTPase | Deoxyuridine triphosphatase, eliminates dUTP to prevent incorporated into DNA | 38 | 9 | 17 | <1 | AF091101 |
| Hells | Helicase, lymphoid specific | 18 | 10 | 17 | <1 | NM_008234 |
| cdc6-G1/S peak | Cell division cycle 6 (loads MCM7), licensing factor | 40 | 6 | 12 | <1 | NM_011799 |
| CDT1 | DNA replication licensing. Loads mcm2-7. Oncoprotein in 3T3 | 27 | 8 | 60 | 8 | AF477481 |
| mcm3-G1/S peak | Mini chromosome maintenance deficient 3 | 24 | 4 | 19 | 3 | BF606890 |
| mcm5-G1/S peak | Mini chromosome maintenance deficient 5-replication licensing helicase | 42 | 3 | 27 | 4 | NM_008566 |
| mcm6-G1/S peak | Mini chromosome maintenance deficient 6-replication licensing helicase | 90 | 4 | 50 | 7 | NM_008567 |
| mcm7-G1/S peak | Mini chromosome maintenance deficient 7-replication licensing helicase | 134 | 20 | 100 | 15 | BB464359 |
| Rpa2 | replication protein A2 | 30 | 1 | 19 | 4 | AK011530 |
| priA | DNA polymerase primase p49 subunit | 24 | 6 | 14 | 3 | NM_008921 |
| Smu1 | DNA replication, activation of cdc2 kinase, spindle assembly, chromosome integrity | 26 | 3 | 20 | 12 | |
| Ribosome biogenesis, RNA maturation | | | | | | |
| Nola1 | Nucleolar protein family A, member 1, snRNP | 32 | 10 | 30 | <1 | NM_026578 |
| Nol5 | Nucleolar protein 5, Nop5 | 44 | <1 | 24 | <1 | BB729616 |
| U50snoRNA | mU50, snoRNA | 42 | 4 | 23 | <1 | AK012825 |
| NOP56 | Nucleolar protein 56 | 66 | 6 | 28 | 70 | BM249243 |
| Nolc1 | Nucleolar and coiled body phosphoprotein 1 | 22 | <1 | 24 | 2 | BM236574 |
| p38-2G4 | Proliferation-associated nuclear non-nucleolar factor PA2G4 | 44 | 3 | 46 | 5 | NM_011119 |
| Lyar | Zinc-finger nucleolar protein that promotes oncogenesis | 54 | 10 | 24 | 4 | NM_025281 |
| U22snRNP | U22 small nucleolar ribonuclear protein | 50 | 6 | 40 | 7 | BQ177137 |

TABLE 2-continued

Gene down-regulation in SCF Hoxb8-ER neutrophil progenitors and in GM-CSF Hoxb8-ER macrophage progenitors

| Gene | Comment | Neut Prog 0 | Neut Prog 6d | Mac Prog 0 | Mac Prog 6d | Genbank |
|---|---|---|---|---|---|---|
| Hnrnpa1 | heterogeneous nuclear ribonucleoprotein A1 | 92 | 10 | 90 | 24 | AK007802 |
| ASF/SF2 | splicing factor, arginine/serine-rich 1 | 32 | 3 | 30 | 7 | NM_173374 |
| SF3a | splicing factor 3a | 30 | 2 | 10 | 4 | BC009141 |
| *Differentiation-related or unknown functions* | | | | | | |
| Ela2 | Elastase 2, Neutrophil elastase, serine proteinase | 20 | <1 | 156 | <1 | NM_015779 |
| MPO | Myeloperoxidase | 320 | 3 | 176 | 3 | NM_010824 |
| Prtn3 | Proteinase 3, myeloblastin, serine proteinase, in azurophilic granuals | 294 | 4 | 188 | <1 | U97073 |
| Ctsg | Cathepsin G, granual protein, serine proteinase | 400 | 20 | 194 | 2 | NM_007800 |
| Cystatin F | Cystein proteinase inhibitor, hematopoietic-specific | 82 | 8 | 82 | <1 | NM_009977 |
| Cnn3 | Calponin 3, actin-binding protein | 136 | 3 | 54 | <1 | BB724741 |
| Bcrp1 | Responsible for Hoechst 33342 exclusion of "side population" of stem cells | 48 | 3 | 28 | 14 | |
| Ms4a3 | Membrane-spanning 4-domains subfamily A, member 3,, HTm4 | 50 | 4 | 154 | 1 | NM_133246 |
| Plac8 | Placental 8, unknown function | 240 | 4 | 180 | 1 | AF263458 |
| Igfbp4 | Insulin-like growth factor binding protein 4 | 32 | 3 | 34 | 2 | BC019836 |
| Slc16a1, MCT1 | monocarboxylate transporter | 66 | 5 | 41 | 4 | NM_009196 |
| Cyclophilin D | Peptidylprolyl isomerase D | 48 | 8 | 28 | 3 | BC011499 |
| Slc19a1 | Folate carrier, methotrexate importer | 26 | 2 | 32 | 4 | AI323572 |
| F13a1 | Coagulation factor XIII, A1 subunit | 112 | 20 | 170 | 25 | NM_028784 |
| FKBP4 | FK506 binding protein 4, FKBP52 | 34 | 4 | 31 | 5 | NM_010219 |
| ICAM2 | Intercellular adhesion molecule 2 | 26 | 6 | 17 | 4 | NM_010494 |
| Timm8a | Translocase of inner mitochondrial membrane | 30 | 7 | 24 | 7 | NM_013898 |
| Csda | Cold shock domain protein | 50 | 10 | 30 | 9 | AV216648 |
| Icdh | Isocitrate dehydrogenase 3, subunit alpha | 31 | 3 | 34 | 6 | AK003393 |
| Nedd4 | Ubiquitination (developmentally regulated) | 38 | 1 | 9 | <1 | NM_010890 |
| Tilz1b | TSC22-related, Tgfb1i4, Growth factor inducible | 44 | 2 | 94 | 9 | AU016382 |
| Unknown | hematopoietic-specific | 72 | 2 | 30 | <1 | BC035044 |
| *Transcription factors* | | | | | | |
| c-Myc | Myelocytomatosis proto-oncogene | 102 | 2 | 65 | 11 | BC006728 |
| Pontin52, Tip49, Ruvb1 | Helicase, binds TATA-binding protein, Myc, E2F, and b-catenin transactivation complexes | 24 | <1 | 20 | 6 | NM_019685 |
| Reptin52, Tip48, Ruvb2 | Helicase, transcription regulation | 75 | 4 | 31 | 6 | NM_011304 |
| c-Myb | Myelocytomatosis proto-oncogene | 116 | 28 | 62 | <1 | NM_033597 |
| B-Myb | Myeloblastosis oncogene-like 2, regulates cell cycle through interaction with E2F-binding protein p107, maintains ES cell stem-likeness | 8 | <1 | 14 | <1 | NM_008652 |
| Gfi-1 | Growth factor independent--Zinc finger transcriptional repressor | 33 | 8 | 41 | <1 | NM_010278 |
| Nsbp1, NBP-45, GARP45 | Nucleosome binding protein 1, has transactivation function, embryonic expression | 21 | 3 | 18 | 2 | NM_016710 |
| Hmgb3/Hmg4 | High mobility group member b3, Embryonic expression, hemopoietic stem cells | 70 | 5 | 48 | 11 | NM_008253 |
| Rbb4 | Retinoblastoma binding protein 4 | 61 | <1 | 36 | 10 | BF011461 |
| Sox4 | HMG protein, oncoprotein | 36 | <1 | <1 | <1 | NM_009238 |
| HMG14 | HMGN1 | 94 | 6 | <1 | <1 | NM_008251 |
| Unknown | | | | | | |

FIG. 3. Gene up-regulation in SCF Hoxb8-ER neutrophil progenitors and in GM-CSF Hoxb8-ER macrophage progenitors

| Gene | Comment | Neutrophil Prog | Diff | Macrophage Prog | Diff | Genbank |
|---|---|---|---|---|---|---|
| Early myeloidmarkers | | | | | | |
| Fcgr2b | IgG Fc gamma receptor 2 beta, low affinity | 32 | 34 | 34 | 52 | BM224327 |
| Fcgr3 | IgG Fc gamma receptor 3, low affinity | 38 | 38 | 32 | 58 | NM_010188 |
| CCR2 | Receptor for macrophage chemotactic protein (MCP1) | 138 | 62 | 84 | 192 | U47035 |
| Fcer1g | IgE Fc receptor 1 gamma, high affinity | 32 | 30 | 44 | 104 | NM_010185 |
| Neutrophil markers | | | | | | |
| IL8Rbeta | IL8 Receptor beta | <1 | 38 | <1 | <1 | NM_009909 |
| IL17R | IL17 Receptor | 11 | 60 | <1 | 2 | NM_008359 |
| LF | Lactoferrin/Lactotransferrin | <1 | 190 | <1 | <1 | NM_008522 |
| LRG1 | LRG1, Leucine-rich alpha-2-glycoprotein | <1 | 74 | 2 | 1 | NM_029796 |
| NB-1 | NB-1 | <1 | 20 | 1 | <1 | BC027283 |
| Cnlp | Cathelin, anti-bacterial peptide | <1 | 440 | <1 | <1 | NM_009921 |
| Lip2 | Lipocalin 2, In granulocytic precursors and epithelia cells | 3 | 240 | 3 | 5 | X14607 |
| MMP9 | Neutrophil gelatinase, Gelatinase B | <1 | 152 | <1 | <1 | NM_013599 |
| NG | Neutrophil gelatinase, MMP9 | <1 | 196 | 2 | 14 | NM_013599 |
| Pglyrp | Peptidoglycan recognition protein, neutrophil granual protein | 4 | 76 | 8 | 9 | NM_009402 |
| Stefin A1, Cystatin A | Cystein proteinase (Cathepsin) inhibitor, Stefin 3 | 10 | 520 | 2 | 10 | AW146083 |
| Stefin A2-like 1 | Cystein proteinase inhibitor | 4 | 460 | 1 | 17 | BB667930 |
| Itgb2l, Pactolus | Neutrophil-specific Integrin beta 2-like | <1 | 50 | <1 | <1 | NM_008405 |
| Stefin A3 | Cystein proteinase inhibitor | <1 | 340 | <1 | 10 | NM_025288 |
| Ngp, Bactinecin | Neutrophilic granual protein, Cathelin- and Cystatin-homology | 13 | 170 | 22 | 2 | NM_008694 |
| Arg1 | Arginase 1 | <1 | 330 | <1 | <1 | NM_007482 |
| Bcl6 | Zn-finger transcriptional repressor | <1 | 76 | <1 | 2 | NM_009744 |
| Rnf11 | Ring Finger 11, Ubiquitination specificity | 8 | 224 | 4 | 7 | BI150320 |
| Rnf144 | Ring Finger 144, Ubiquitination specificity | 16 | 102 | <1 | <1 | BB125275 |
| Pdi4 | Histone H3 specific pepdidyl arginine deiminase, transcriptional repression | <1 | 44 | <1 | <1 | NM_011061 |
| CDCRel1 | GTP-binding protein | 3 | 96 | 10 | 4 | AF033350 |
| Trim12 | Tripartite motif protein 12 | 1 | 22 | <1 | <1 | BM244351 |
| Ceacam1 | CEA-related cell adhesion molecule 1 | 3 | 41 | 4 | 6 | BC016891 |
| Ceacam10 | CEA-related cell adhesion molecule 2 | <1 | 160 | <1 | 1 | NM_007675 |
| Wdnm1 | Proteinase inhibitor | 2 | 173 | 15 | 11 | AV006463 |
| Olfactomedian4 | Secreted neutrophil glycoprotein, pDP4 | <1 | 112 | 8 | 6 | AV290148 |
| Crispld2 | cysteine-rich secretory protein LCCL domain containing 2 | <1 | 56 | <1 | <1 | BB558800 |
| mDia1 | Diaphanous protein homolog 1, Rho effector, cell motility | <1 | 44 | 2 | 4 | AW554652 |
| Olfl1 | Olfactomedian-like1 | <1 | 22 | 5 | 6 | AV230978 |
| Slc2a3 | Facilitated glucose transporter | 20 | 274 | 3 | 2 | BB414515 |
| Olfml2b | Olfactomedian-like 2b, photomedian 2 | <1 | 19 | <1 | <1 | BC025654 |
| St3gal4 | ST3 beta-galactoside alpha-2, 3-sialyltransferase 4, neutrophil rolling | 2 | 50 | <1 | <1 | BE954474 |
| Mcp8 | Mast cell protease 8 | 58 | 164 | <1 | <1 | NM_008572 |
| Syne1 | Nuclear organization | <1 | 54 | <1 | <1 | BI734306 |
| cyp450 4f18 | Cytochrome p450 4f18, unknown function | 2 | 54 | <1 | <1 | |
| Stk17b | Serine-threonine kinase, apoptosis-inducing | <1 | 32 | <1 | 2 | NM_133810 |
| Cd73 | ecto-5'-nucleotidase | <1 | 30 | <1 | <1 | AV273591 |
| Unknown | 1691 aa, Protein ID BAE42230 | <1 | 17 | <1 | <1 | BG070087 |
| Unknown | 216 aa, | | | | | |
| Unknown | 786 aa, Denn and Madd domains. Conserved to C. Elegans, Gene 1437121 | 3 | 52 | <1 | 5 | BB168293 |
| Unknown | 463 aa, conserved to C. elegans, Gene 1424463 | 2 | 64 | <1 | <1 | NM_133829 |
| Unknown | 537 aa, conserved to C. elegans, PL48, Up in neuts from HL60, Gene 1460555 | 8 | 66 | 2 | 2 | NM_178658 |
| Monocyte/Dendritic markers | | | | | | |
| F4/80 | Emr1 | <1 | 1 | 10 | 26 | U66888 |
| ICSBP/IRF-8 | Interferon Consensus Sequence binding protein | 4 | <1 | 18 | 16 | NM_008320 |
| MMP12 | Macrophage elastase, Matrix metalloproteinase 12, | <1 | 5 | 56 | 300 | NM_008605 |

FIG. 3. Gene up-regulation in SCF Hoxb8-ER neutrophil progenitors and in GM-CSF Hoxb8-ER macrophage progenitors

| Gene | Comment | Neutrophil Prog | Diff | Macrophage Prog | Diff | Genbank |
|---|---|---|---|---|---|---|
| Macrosialin | CD68, Class D scavenger receptor | 333 | 5 | 26 | 120 | BC021637 |
| Dectin-2beta | Dendritic cell-associated C-type lectin, Clecsf10 | <1 | <1 | 72 | 360 | NM_020001 |
| CD11c | Integrin alpha X, ItgaX, Dendritic marker | <1 | 5 | 14 | 117 | NM_021334 |
| Msr1 | Macrophage scavenger receptor 1 (SR-A) | <1 | <1 | 2 | 30 | NM_031195 |
| Msr2 | Macrophage scavenger receptor 2 | <1 | <1 | <1 | 32 | BC016551 |
| mMGL2 | Macrophage galactose N-acetyl-galactosamine specific lectin | <1 | 7 | 12 | 132 | AW494220 |
| CCL17 | CCR4 ligand, T cell chemokine produced by macrophages | <1 | <1 | 5 | 48 | NM_011332 |
| CCL22 | CCR4 ligand, T cell chemokine produced by macrophages, aka MDC | <1 | <1 | <1 | 19 | BC012658 |
| MHC-H2-Ealpha | Histocompatibility 2, class II, antigen E alpha | <1 | <1 | 2 | 109 | NM_010381 |
| MHC-H2-Abeta1 | Histocompatibility 2, class II antigen A, beta 1 | <1 | <1 | 5 | 95 | BC008168 |
| MHC-H2-Aalpha | Histocompatibility 2, class II antigen A, alpha | <1 | 20 | 9 | 164 | AV018723 |
| MHC-H2-Ealpha | Histocompatibility 2, class II, antigen IE alpha | <1 | <1 | 9 | 133 | AF119253 |
| MHC-H2-Ebeta1 | Histocompatibility 2, class II, antigen E beta 1 | <1 | 3 | 4 | 142 | NM_010382 |
| MHC-H2-DM beta2 | Histocompatibility 2, class II, locus DMb2 | 2 | 3 | 9 | 69 | NM_010388 |
| MHC-H2-DM alpha | Histocompatibility 2, class II, locus Dma | 15 | 2 | 10 | 94 | NM_010386 |
| Csf2rb1 | GM-CSF receptor low-affinity Beta 1 | 10 | 14 | 38 | 134 | NM_007780 |
| DCL-1 | Dendritic cell receptor, C-type lectin--unknown function | <1 | <1 | 11 | 66 | NM_025422 |
| DCAR | Dendritic cell activating immunoreceptor (FcReceptor gamma-associated) | <1 | <1 | 7 | 54 | NM_027218 |
| Car4 | Carbonic anhydrase 4 | <1 | <1 | 42 | 30 | NM_007607 |
| CD74 | Macrophage migration inhibitory factor receptor, Ia-gamma, CLIP, DHLAG | <1 | 6 | 11 | 292 | BC003476 |
| Capg | Gelsolin-like. Involved in receptor-mediated ruffling, phagocytosis | 6 | 11 | 18 | 92 | NM_007599 |
| F7 | Coagulation factor VII | <1 | 14 | 166 | 250 | NM_010172 |
| Lpl1 | Lipoprotein Lipase, Secreted, Hydrolyzes VLDL | <1 | 27 | 140 | 250 | NM_008509 |
| Lrp1 | LDL-related protein, macrophage marker | <1 | 1 | 8 | 30 | NM_008512 |
| Ifi30 | Lysosomal thiol reductase, interferon gamma inducible protein 30 | 1 | <1 | 28 | 76 | NM_023065 |
| NOV | Connective tissue growth factor | <1 | <1 | 22 | 54 | X96585 |
| CCL9 | MIP1 gamma, Scya9/Scya10 | 90 | <1 | 120 | 140 | NM_011338 |
| EST1 | 456 aa, Widely expressed | <1 | <1 | 24 | 44 | BB559293 |
| Myeloid differentiation markers upregulated in both neutrophils and monocytes | | | | | | |
| Fpr1 | Formyl peptide receptor 1 | <1 | 48 | <1 | 30 | NM_013521 |
| Fpr-rs2 | Formyl peptide receptor-related sequence 2 | 1 | 104 | 4 | 118 | NM_008039 |
| Dectin-1 | Clecsf12, beta glucan receptor, fungal recognition | 4 | 138 | 20 | 147 | NM_020008 |
| CD300lf | CD300-like factor, Pigr3, CLIM1, Polymeric Ig Receptor III | <1 | 260 | 5 | 35 | NM_145634 |
| Mrc1 | Mannose receptor, C1, macrophage/dendritic, binds bacterial C-terminal mannose | <1 | 76 | 13 | 226 | NM_008625 |
| TLR2 | Toll-like receptor 2 | <1 | 30 | 10 | 25 | NM_011905 |
| P2ry6 | Pyrimidinergic receptor P2Y activated by UDP | <1 | 18 | <1 | 38 | BC027331 |
| CD14 | TLR coreceptor | 5 | 40 | 40 | 136 | NM_009841 |
| Mac1 | CD11b/Integrin alpha M/CD18 | 2 | 28 | 9 | 48 | NM_008401 |
| Fgr | Src-family myeloid tyrosine protein kinase | 2 | 70 | 2 | 52 | NM_010208 |
| MMP8 | Matrix metalloproteinase 8 | 6 | 154 | 74 | 154 | NM_008611 |
| Lyzs | Lysozyme | 6 | 260 | 200 | 380 | AW208566 |
| Gsn | Gelsolin, involved in podosome formation | 2 | 30 | 74 | 80 | NM_010354 |
| Lgmn | Legumain, activates cathepsins B, H, L | <1 | 29 | 1 | 65 | NM_011175 |

FIG. 3. Gene up-regulation in SCF Hoxb8-ER neutrophil progenitors and in GM-CSF Hoxb8-ER macrophage progenitors

| Gene | Comment | Neutrophil Prog | Diff | Macrophage Prog | Diff | Genbank |
|---|---|---|---|---|---|---|
| Vacuolar H+ ATPase | Subunit d2 isoform | <1 | 80 | 17 | 126 | AV204216 |
| Vti1b | Vesicle transport through interaction with tSNAREs, facilitates exocytosis | <1 | 54 | <1 | 26 | AV002218 |
| Sirpbeta1 | Signal regulatory protein beta 1, activation promotes phagocytosis, induces filopodia and lamellipodia, binds DAP12 | <1 | 140 | 5 | 82 | AI662854 |
| Mcl | Macrophage C-type lectin, Clecsf8, endocytic recptor | 31 | 156 | 27 | 308 | NM_010819 |
| TLR1 | Toll-like receptor 1 | <1 | 6 | <1 | 14 | NM_030682 |
| TLR4 | Toll-like receptor 4 | 2 | 14 | 16 | 14 | NM_021297 |
| TLR6 | Toll-like receptor 6 | 3 | 14 | <1 | 6 | NM_011604 |
| Lilrb4 | Leukocyte Ig-like inhibitory receptor B4 | <1 | 54 | 30 | 121 | U05264 |
| Pira1 | Paired-Ig-like activating receptor A1, binds FcRgamma | <1 | 24 | 34 | 58 | NM_011087 |
| Pilra | Paired IG-like type II inhibitory receptor alpha | <1 | 54 | 18 | 64 | BB775785 |
| Pira6 | Paired-Ig-like activating receptor A6, binds FcRgamma | <1 | 14 | 44 | 86 | NM_011093 |
| Pilrb1 | Paired-Ig-like type II activating receptor beta | 2 | 158 | 24 | 90 | NM_133209 |
| Pirb5 | Paired-Ig-like inhibitory receptor B5, dendritic/B cells | <1 | 40 | 14 | 30 | U96693 |
| Gp49b1 | Ig inhibitory receptor | <1 | 54 | 30 | 120 | NM_013532 |
| CCR1 | CC chemokine receptor 1 | <1 | 30 | 10 | 56 | BC011092 |
| CD157 | fMLP receptor, ADP-ribosyl cyclase. Mediates adhesion, motility, and chemotaxis. In uropod | <1 | 48 | 2 | 20 | NM_009763 |
| C3aR1 | Complement component 3a receptor 1-high affinity | 1 | 24 | 6 | 28 | BC003728 |
| DCIR3 | Dendritic cell inhibitory receptor 3--unknown function | <1 | 43 | 8 | 92 | AK014135 |
| DCIR | Dendritic cell immunoreceptor-inhibitory, Clecsf6 | 2 | 92 | 10 | 94 | NM_011999 |
| DC-HIL | Dendritic cell transmembrane protein, adhesion, binds RGD/proteoglycans | 4 | 104 | 108 | 266 | NM_053110 |
| Fcgrt | IgG Fc receptor, alpha chain transporter | <1 | 2 | 34 | 60 | NM_010189 |
| IL1R2 | Interleukin 1 receptor, type II (pro-inflammatory) | 3 | 40 | 12 | 42 | NM_010555 |
| St2L | IL1-like receptor negative feedback of pro-inflammatory function | 44 | 212 | 2 | 32 | D13695 |
| IEX-1, IER-3 | Immediate early response gene 3, protects against apoptosis | 12 | 32 | 11 | 70 | NM_133662 |
| CD200 Receptor | Ig superfamily, myeloid-restricted, negative regulation of cell activation | 5 | 10 | 4 | 52 | NM_021325 |
| TNFR-1 | Tumor necrosis factor receptor 1, pro-inflammatory | 10 | 36 | 12 | 128 | M59378 |
| betaig-h3 | Integrin-binding ECM protein, adhesion, TGF beta-induced 68 kDa | 16 | 50 | <1 | 25 | NM_009369 |
| CD166 | ALCAM (activated leukocyte cell adhesion molecule) | <1 | 34 | 5 | 44 | AV315205 |
| IL1b | Interleukin 1 beta | 5 | 186 | 6 | 68 | BC011437 |
| MIP-2 | CXCL2, Scyb2, Macrophage inflammatory protein 2, dendritic cell inflammatory protein | <1 | 38 | <1 | 74 | NM_009140 |
| CCL6 | CC chemokine ligand 6, Scya6, C10, macrophage chemokine | <1 | 42 | 132 | 540 | NM_009139 |
| Tubulin, beta2 | microtubules, | <1 | 44 | 5 | 56 | BC003475 |
| Myadm | Myeloid dif. Marker, unknown function | <1 | 50 | 18 | 96 | NM_016969 |
| ADAM8 | A disintegrin and metalloproteinase 8 | <1 | 150 | 12 | 32 | NM_007403 |
| gpnmb | Osteoactivin | <1 | 54 | 66 | 320 | NM_053110 |
| Hck | Src-family tyrosine protein kinase | 9 | 28 | 5 | 14 | NM_010407 |
| YM1 | Glycosidase, chitinase 3-like 3, ECF-L | <1 | 163 | <1 | 19 | NM_009892 |
| YM2 | Secretory protein precursor | 3 | 33 | 3 | 12 | AY065557 |
| Arg2 | Arginase, type II (NO biosynthesis) | <1 | 72 | <1 | 16 | NM_009705 |
| L-Selectin | Mediates roling of leukocytes on endothelium | 2 | 36 | 2 | 10 | NM_011346 |
| CC3 | Complement component C3 | 5 | 40 | 10 | 34 | K02782 |
| Timp2 | Tissue inhibitor of metalloproteinase 2 | 2 | 44 | 2 | 17 | BF168458 |
| CD9/MRP-1 | Mobility related protein 1, tetraspanin protein | 6 | 42 | 6 | 72 | NM_007657 |

FIG. 3. Gene up-regulation in SCF Hoxb8-ER neutrophil progenitors and in GM-CSF Hoxb8-ER macrophage progenitors

| Gene | Comment | Neutrophil Prog | Diff | Macrophage Prog | Diff | Genbank |
|---|---|---|---|---|---|---|
| RhoC | Migration, organization at the leading edge | <1 | 20 | 2 | 12 | AI503490 |
| Puma-g | Interferon-gamma inducible gene | <1 | 162 | 5 | 22 | NM_030701 |
| IFITM3 | Similar to interferon-induced TM protein 3 | <1 | 66 | 4 | 19 | BB193024 |
| Zfp36 | TIS11b, Zinc finger protein 36, Brf1, ERF1, cMG1, Berg36, mRNA stability | 4 | 28 | 13 | 78 | X14678 |
| Rgs2 | Regulator of G protein signaling 2 | 9 | 80 | 6 | 24 | NM_009061 |
| ASK1 | Links TRAF6 to p38 signaling in innate immunity | 5 | 31 | 2 | 6 | AV377656 |
| Csf2ra | Colony-stimulating factor 2 receptor alpha, GM-CSF R alpha, low-affinity | 9 | 108 | 54 | 78 | NM_009970 |
| Osteopontin | Th1 immune reaction, ECM formation and Ca deposition in the bone/kidney | 6 | 96 | 202 | 148 | NM_009263 |
| Sema4a | Dentritic cell expression, immunomodulation | <1 | 32 | 20 | 34 | BB114323 |
| ifitm3 | interferon-induced transmembrane 3 | <1 | 68 | 3 | 18 | BB193024 |
| Lyst | Lysozomal trafficking regulator | 8 | 168 | 12 | 22 | BB463428 |
| Cybb | Cytochrome b-245, gp91phox | 2 | 64 | 52 | 210 | NM_007807 |
| Cathepsin S | | 7 | 217 | 108 | 457 | NM_021281 |
| Gpsm3 | G-protein signaling modulator 3, regulates Gi alpha activation | 4 | 280 | 18 | 52 | NM_134116 |
| MRP8 | S100a8; pro-inflammatory, activates endothelial cells, high in neutrophils | 6 | 312 | 140 | 258 | NM_013650 |
| MRP14 | S100a9; pro-inflammatory, activates endothelial cells, high in neutrophils | 4 | 368 | 42 | 48 | NM_009114 |
| SASPase | Skin aspartyl protease | <1 | 30 | 3 | 10 | AK004007 |
| RGS14 | Regulator of G protein signaling 14 | 3 | 25 | 10 | 18 | NM_016758 |
| Slc15a3, PHT2 | Histidine, dipeptide transporter | <1 | 37 | 2 | 35 | NM_023044 |
| TMEM23 | Sphingomyelin synthase 1, MOB, SMS1 | <1 | 32 | 3 | 40 | AV244175 |
| MKP1, dusp1 | Ptpn16, inactivates Jun kinase, prevents reentrance into the cell cycle, negative regulator of inflammation | 7 | 109 | 5 | 114 | NM_013642 |
| Samhd1 | SAM and phosphohydrolase domain, Unknown function | 2 | 68 | 6 | 31 | NM_018851 |
| Ier5 | Immediate early response 5, Unknown function | 2 | 20 | 2 | 22 | NM_010500 |
| Unknown | Unclassifiable transcript, BC025215 | 5 | 160 | 106 | 216 | AK018202 |
| Transcription factors | | | | | | |
| ICSBP | Interferon Consensus Sequence binding protein | 4 | <1 | 18 | 16 | NM_008320 |
| Mad | Max dimerization protein | 4 | 88 | 7 | 15 | BB036846 |
| ATF3 | c-jun-related bZIP transcription factor | <1 | 31 | 3 | 56 | NM_007498 |
| JunB | Jun family member B, bZIP transcription factor | 7 | 54 | 4 | 54 | NM_008416 |
| c-fos | FBJ osteosarcoma proto-oncogene, bZIP transcription factor | 8 | 72 | 12 | 214 | NM_010234 |
| Btg2 | B-cell translocation gene 2, anti-proliferative, Tis21, Pc3 | 2 | 52 | 12 | 200 | BG965405 |
| ID2 | Inhibitor of Helix-Loop-Helix differentiation proteins | 4 | 28 | 16 | 218 | NM_010496 |
| Klf2 | Krupple-like factor 2, activates p21WAF1/CIP1 | 4 | 54 | 7 | 18 | NM_008452 |
| c-Jun | bZIP transcription factor | 2 | 40 | 2 | 13 | BC002081 |
| Egr-2 | Early growth response 2, Zinc-finger transcription factor, Krox20 | 3 | 28 | 4 | 48 | X06746 |
| Egr-1 | Early growth response 1, Zinc-finger transcription factor | 44 | 120 | 18 | 135 | NM_007913 |
| JunD1 | Jun family member D, bZIP transcription factor | 4 | 52 | 22 | 100 | NM_010592 |
| Ets1 | E26 proto-oncogene | <1 | 8 | 7 | <1 | BB151715 |
| KLF6 | Krupple-like factor 6 | 6 | 76 | 4 | 20 | NM_011803 |
| CEBP beta | upregulated in myeloid differentiation | 11 | 54 | 54 | 92 | NM_009883 |
| KLF7 | Krupple-like factor 7 | 2 | 30 | 3 | 6 | BE851797 |

TABLE 4

Inflammatory genes induced by LPS or sBLP in GM-CSF Hoxb8-ER-derived macrophages.

| Gene | Comment | Genbank | Basal | LPS 2 hr | sBLP 2 hrs | Fold stim |
|---|---|---|---|---|---|---|
| | Secreted proteins/Ligands | | | | | |
| IL1a | IL1 alpha | BC003727 | 4 | 134 | 26 | >30 |
| IL6 | Interleukin 6 (signals through STAT3) | NM_031168 | <1 | 55 | <1 | >30 |
| IL23p19 | Interleukin 23 | NM_031252 | <1 | 50 | 1 | >30 |
| LIF | Leukemia inhibitory factor | BB235045 | 1 | 81 | 20 | >30 |
| RANTES | RANTES, Scya5, CCL5 | NM_013653 | <1 | 53 | <1 | >30 |
| CXCL10 | IP10, Scyb10, T cell chemoattractant (produced by Macrophages) | NM_021274 | <1 | 182 | 121 | >30 |
| Serpin b2 | PAI-2; plasminogen activator inhibitor 2 (uPA inhibitor) | NM_011111 | 2 | 76 | 19 | 25 |
| TNFsf9 | TNF ligand 9, binds 4-1BB receptor on T cells | NM_009404 | <1 | 24 | <1 | 25 |
| IL12p40 | Interleukin 12p40 (STAT4) drives T helper cell differentiation | NM_008352 | <1 | 19 | <1 | 19 |
| Serpinb9g | NK21B, Inhibits granzyme b, the killing protease of CTL, NK cells | AF425083 | 5 | 94 | 40 | 19 |
| Dermokine | Dermokine alpha/beta, secreted peptide, unknown function | BI452905 | <1 | 18 | 12 | 18 |
| IFN-beta | Interferon beta (signals through STAT1 and STAT2) | NM_010510 | <1 | 16 | <1 | 16 |
| CCR11 | A receptor for MCP-1, LPS-induced | AJ318863 | 7 | 104 | 54 | 15 |
| Hamp | Hepcidin antimicrobial peptide, iron homeostasis, LPS/IL6 upregulated | NM_032541 | <1 | 14 | <1 | 14 |
| Activin | Inhibin beta (dimer = activin) TGF-b/DPP superfamily; neg reg of inflammation, promotes differentiation), signals through smad proteins | NM_008380 | 5 | 71 | 8 | 14 |
| IL1beta | IL1 beta | BC011437 | 18 | 215 | 86 | 12 |
| TNF alpha | TNF alpha | NM_013693 | 30 | 320 | 145 | 11 |
| MCP3 | Monocyte chemotactic protein 3; MCP3, Scya7, CCL7 | AF128193 | <1 | 11 | 2 | 11 |
| MCP1 | Monocyte chemoattractant protein 1; Scya2/CCL2 | AF065933 | 4 | 51 | 9 | 11 |
| CXCL11 | IFN-inducible T cell alpha chemoattractant (I-TAC), scyb11 | AF136449 | 2 | 18 | 3 | 10 |
| Serpin e1 | PAI-1; plasminogen activator inhibitor 1 (tPA and uPA inhibitor) | NM_008871 | 11 | 110 | 23 | 10 |
| MIP1 alpha | Macrophage inflammatory protein 1 alpha; MIP1alpha, Scya3, CCL3 | NM_011337 | 26 | 254 | 114 | 10 |
| MIP2 | Macrophage inflammatory protein 2 (CXCL2) | BB829808 | 6 | 54 | 9 | 9 |
| ICOS ligand | Inducible costimulatory receptor ligand, binds B7-H2, coactivates T cells | NM_015790 | 4 | 28 | 11 | 7 |
| | Signaling regulators | | | | | |
| ISG15 | Interferon-stimulated gene 15, covalently modifies protein | AK019325 | <1 | 54 | 44 | >30 |
| Usp18 | Ubiquitin specific protease 18, aka U8P43 (hydrolyzes ISG15 from protein) | NM_011909 | <1 | 46 | 42 | >30 |
| Rtp4 | 28 kDa IFN alpha responsive protein, receptor transport protein 4 | NM_023386 | <1 | 51 | 48 | >30 |
| MIC-1 | Macrophage inhibitory cytokine 1, GDF15, TGF beta family member | NM_011819 | <1 | 80 | 58 | >30 |
| A20/Tnfaip3 | A20, removes ubiquitin from TRAF6, downregulates Toll/NF-kB signaling | NM_009397 | 2 | 42 | 17 | 21 |
| SOCS3/Cish3 | Cytokine-inducible SH2-containing protein 3, negative regulation | NM_007707 | <1 | 21 | 10 | 21 |
| TDAG51 | Signaling protein that promotes survival | NM_009344 | 4 | 60 | 24 | 13 |
| PAC1/Dusp2 | Dual (Y/T) specificity phosphatase PAC-1, Map kinase phosphatase | L11330 | 1 | 10 | 10 | 10 |
| Pellino1 | Required for NF-kB activation through IL-1R | NM_023324 | 4 | 30 | 8 | 7 |
| MKP-7/Dusp16 | Dual specificity phosphatase 16 (targets Jun kinase), MKP-7, LPS-activated | NM_130447 | 3 | 20 | 4 | 6 |
| Pde4b | phosphodiesterase 4B, inflammatory cell activation | AF326555 | 4 | 26 | 10 | 6 |
| Arhe | Ras homology gene, member E | NM_028810 | <1 | 6 | <1 | 6 |
| TLR7 | Toll-like receptor 7 | NM_133211 | 6 | 30 | 22 | 5 |
| Tnfrsf23 | Tumor necrosis factor receptor super family member 23, TRAIL decoy receptor | NM_024290 | <1 | 18 | 17 | 18 |
| | Others | | | | | |
| Cox-2 | Cyclooxygenase 2, involved in prostaglandin synthesis | M88242 | 2 | 119 | 59 | >30 |
| TG2 | Transglutaminase 2 (upreguated in inflammation) | BC016492 | 2 | 74 | 62 | >30 |
| Gbp2 | Interferon gamma-induced guanylate nucleotide binding protein 2 | NM_010260 | <1 | 38 | 26 | >30 |
| Ifit-2/Ifi54 | Interferon-induced protein with tetratricopeptide repeats 2 | NM_008332 | <1 | 98 | 56 | >30 |
| Ifi16/Ifi204 | Interferon-induced protein 204, transcriptional coactivator, induces differentiation | NM_008329 | <1 | 35 | 26 | >30 |
| Vlperin | Interferon-induced anti-viral glycoprotein | NM_021384 | <1 | 118 | 84 | >30 |
| Tyki | LPS-induced thymidylate kinase | NM_020557 | <1 | 35 | 30 | >30 |
| Ifit3/Ifi49 | Interferon-induced protein with tetratricopeptide repeats 3 | NM_010501 | <1 | 56 | 46 | >30 |
| Ifit1/Ifi56 | Interferon-induced protein with tetratricopeptide repeats 1 | NM_00833 | <1 | 116 | 48 | >30 |
| Ifi205 | Interferon-inducible gene 205, macrophage expression | AI481797 | <1 | 48 | 28 | >30 |
| MIP-2 | CXCL2, Scyb2, Macrophage inflammatory protein 2, dendritic cell inflammatory protein | NM_009140 | 2 | 118 | 85 | >30 |
| Mpa2l, GBP1 | Macrophage activation 2-like, G-protein | BM241485 | 2 | 52 | 32 | >30 |
| BimL | BimL--proapoptotic protein | AF032460 | 2 | 44 | 15 | 24 |
| Trim30 | Tripartite motif protein | BM241342 | <1 | 22 | 21 | 22 |
| Bcl2a1a | Bcl2a1a | AI326167 | <1 | 8 | 4 | 15 |
| Serpine 1 | Plasminogen activator inhibitor type I | NM_008871 | 3 | 50 | 10 | 15 |
| Irg1 | Immune-responsive gene 1, propionate catabolism | L38281 | 9 | 104 | 16 | 12 |

TABLE 4-continued

Inflammatory genes induced by LPS or sBLP in GM-CSF Hoxb8-ER-derived macrophages.

| Gene | Comment | Genbank | Basal | LPS 2 hr | sBLP 2 hrs | Fold stim |
|---|---|---|---|---|---|---|
| ICAM-1 | ICAM-1, intracellular adhesion molecule 1 | BC008626 | 2 | 28 | 10 | 12 |
| MIP-2, Dcip1 | Dedritic cell inflammatory protein 1 (LPS induced)-neutrophil chemotaxis | BB829808 | 4 | 54 | 8 | 12 |
| Saa3 | Serum amyloid A3 (LPS-activate) | NM_011315 | 5 | 55 | 6 | 11 |
| Myd116 | Myd116, induced by IL-6, PP1 regulatory subunit 16 | NM_008654 | 5 | 46 | 9 | 10 |
| FIG. 1 | L-amino acid oxidase, interleukin-4 induced (maps to autoimmune succeptibility site; lupus site) | NM_010215 | 3 | 22 | 3 | 8 |
| AdoRA2b | Adenosine A2b receptor, inflammation regulation | NM_007413 | 6 | 50 | 17 | 8 |
| Rdh11 | Retinol dehydrogenase 11 (IL4-induced) | BC018261 | 3 | 22 | 5 | 7 |
| | Transcription factors/regulators of mRNA abundance | | | | | |
| NFkB2 | Nuclear factor kappa B subunit p100 | | <1 | 54 | 28 | >30 |
| Nfkbie | Nuclear factor kappa B inhibitor epsilon | AK011965 | <1 | 36 | 24 | >30 |
| Ikbke | Inhibitor of kappaB kinase epsilon | NM_019777 | <1 | 52 | 24 | >30 |
| Fra-2 | fos-like antigen 2 | NM_008037 | <1 | 32 | 15 | >30 |
| STAT1 | Signal transducer and activator of transcription 1 (IFN signaling) | BB229853 | <1 | 51 | 48 | >30 |
| STAT2 | Signal transducer and activator of transcription 2 (IFN signaling) | AF088862 | <1 | 38 | 32 | >30 |
| Nfkbib | Nuclear factor kappa B inhibitor beta | NM_010908 | 2 | 54 | 29 | 27 |
| Nfkbia | Nuclear factor kappa B inhibitor alpha | NM_010907 | 8 | 210 | 165 | 24 |
| IkappaBzeta | IkappaB zeta, IkappaB MAIL, negative regulator of nuclear NFKB | NM_030612 | 3 | 58 | 24 | 17 |
| Six1 | Sine oculis-related homeobox 1 homolog, development | BB137929 | 1 | 24 | 9 | 17 |
| IkappaBalpha | IkappaBalpha | NM_010907 | 16 | 260 | 210 | 16 |
| I kappa BNS | I kappa BNS, Negative regulator of NF-kappa-B | AW495632 | 10 | 122 | 72 | 12 |
| c-Rel | c-Rel, required for LPS-induced transcription of IL12p40 subunit | NM_009044 | 3 | 28 | 10 | 9 |
| c-Maf | bZIP transcription factor. Activates LPS-induced IL-10 transcription | BC022952 | 3 | 25 | 12 | 9 |
| Nupr1/p8 | p8 transcription factor. Induced by LPS | NM_019738 | 6 | 42 | 10 | 7 |
| JunD1 | bZIP transcription factor | NM_010592 | 38 | 250 | 220 | 7 |
| Jundp2 | Jun dimerization protein 2, inhibits AP1, promotes differentiation | NM_030887 | 7 | 45 | 8 | 6 |
| MALT1 | MALT1, paracaspase involved in NF-Kappa-B activation | BB296321 | 8 | 44 | 28 | 6 |
| RelB | Reticuloendotheliosis oncogene related B | NM_009046 | 9 | 52 | 40 | 5 |
| NFkB1 | Nuclear factor kappa B subunit p105 | L28118 | 20 | 100 | 44 | 5 |
| Egr-1 | Early growth response 1 | NM_007913 | 10 | 38 | 26 | 4 |
| Egr-2 | Krox20, Zinc-finger transcription factor | X06746 | 6 | 25 | 22 | 4 |

The expression levels of 128 myeloid genes is plotted in FIG. 3 (genes plotted are underlined in supplement tables). IL8R-beta, LF, LRG1, NB-1, Lip2 and other neutrophil markers were up-regulated selectively during differentiation of SCF Hoxb8-ER neutrophil progenitors while MMP12, Macrosialin, Dectin-2β, CD11c, Msr1, Msr2, and other macrophage-specific markers were up-regulated coincident with differentiation of GM-CSF Hoxb8-ER macrophage progenitors, and IRF-8, a marker of macrophage lineage commitment, was expressed persistently. Fpr1, Fpr-rs2, Mrc1, TLR2, MMP8, Mac1, Fgr, Lgmn, and other common myeloid differentiation markers were up-regulated during maturation of both progenitor cell types, while common promyelocytic markers, including MPO, PRT3, Ela2, and Cnn3 were strongly down-regulated. This transcriptional profile indicates that Hoxb8-ER progenitors exhibit normal neutrophil and macrophage differentiation. Macrophage-committed GM-CSF Hoxb8-ER progenitors appeared to be positioned at a later stage of myeloid differentiation because they exhibit high basal levels of a subset of late differentiation genes, such as Lyzs, Gsn, CD14, Lilrb4, Pira1, Pira6, Pilrb1, Gp49b1, and DC-HIL (see elevated blue signals in FIG. 3), which were not expressed, but strongly up-regulated during SCF Hoxb8-ER neutrophil differentiation. Changes in gene expression predicted by Affymetrix arrays were verified by a variety of analysis. Immunoblot analysis confirmed up-regulation of the macrophage scavenger receptor (SRC-A) and transcription factors Rel-B and c-Jun (FIG. 3B), FACS analysis confirmed up-regulation of CD11c (FIG. 3C), and Northern blotting confirmed down-regulation of Gfi-1, c-Myb, NOP52, neutrophil elastase, and up-regulation of c-fos (FIG. 3D).

Inactivation of Hoxb8-ER by removal of estrogen resulted in cell cycle arrest following a 4-fold expansion of GM-CSF Hoxb8-ER macrophage progenitors (FIG. 1D) and a 90-fold expansion of SCF Hoxb8-ER neutrophil progenitors. Cell cycle arrest coincided with down-regulation of c-Myb, c-Myc, and Hmgb3, as well as the helicases Pontin 52/Tip49 and Reptin 52/Tip48, which serve as coactivators for c-Myc, TBP, β-catenin, and E2F (Blue tracings in FIGS. 4A and 4C, Table 1). Cell cycle genes (e.g. CycB1, Mcm2), as well as c-Myc target genes (e.g., Nolc1, Shmt2) fell in parallel with expression of c-Myc, Pontin52/Tip49, and Reptin 52/Tip48 (Yellow tracings in FIGS. 4A and 4C). Promyelocyte-specific expression of the c-Myb targets, ELA2 (leukocyte elastase), Ctsg (Cathepsin G), Prtn3 (Proteinase 3/myeloblastin), and MPO (myeloperoxidase) fell in parallel with c-Myb (Brown tracings in FIGS. 4B and 4D). Synchronous expression of differentiation markers (e.g., Fpr1, Fpr-rs2, Dectin-1, Mrc1, Fgr, VacATP; green tracings in FIGS. 4B and 4D) paralleled that of the leucine zipper transcription factors ATF3, Jun-B, c-Fos, and JunD1. This suggests that a broad program of cell cycle gene down-regulation (Supplement Table 2) and differentiation gene up-regulation (Supplement Table 3) is being driven by inactivating c-Myc and c-Myb and up-regulating bZIP transcription factors (ATF3, JunB, c-fos, RelB, c-Jun, JunD1, Egr-1, Egr2; [Krishnaraju et al (1998), Libermann and Hoffman (1994), Kharbanda et al., (1991)]).

Neutrophil and macrophage progenitors immortalized by Hoxb8-ER exhibit normal terminal differentiation based on expression analysis. Mature macrophages evidenced up-regulation of genes involved in adhesion (CD11c, CD11b, DC-HIL, CD157, CD166), migration (CD74, CCR1, CCR5), phagocytosis (SIRPbeta1, DCAR, DCIR3), activation (DCL1, DCIR), pathogen pattern recognition (Mgl2, Mc1, Mrc1, Dectin 1, Fpr1, Fpr-r2, CD157), recognition of necrotic cell debris (Msr1, Msr2, CD36, CD68), T cell stimulation/activation (CD83, MHC2 class II complex antigens E alpha, A beta 1, A alpha, E alpha, Ebeta1, DM loci alpha and beta2, IL-18), migration (MIP-2/CXCL2, MCP-1), bacterial killing (Bactenecin, Cathelin), opsinophagocytosis (CC3, C3aR1), proteolysis/MHC class II peptide generation (LGNM, MMP9, uPA, Cathepsin H, Cathepsin B), protease inhibition (Stefin A1, Stefin A2, Stefin A3, Timp2, PAI-2, Serpinb9 g, Wdnm1), nitric oxide biosynthesis (Arg2, Pdi4), metal ion transport (Slc11a1, LF, transferrin), and receptor signaling via tyrosine kinases (Hck, Fgr). Mature neutrophils up-regulated a largely overlapping group of myeloid maturation genes, in addition to neutrophil-specific granule genes such as lactoferrin (FIG. 4, Table 1, and Table 3).

SCF Hoxb8-ER progenitors behave as Granulocyte/Macrophage Progenitors (GMP), retaining eosinophil differentiation potential. While the strong expression of promyelocytic genes, such as MPO and Prt3, established them as myeloid, the SCF-responsiveness and negligible expression of any terminal differentiation gene in Hoxb8-ER progenitors suggested they might retain the ability to execute alternative differentiation fates in response to other lineage-specific cytokines. To test this hypothesis, SCF Hoxb8-ER progenitors were allowed to differentiate in SCF medium supplemented with GCSF, IL5, MCSF, GM-CSF, or erythropoietin (FIG. 5). Inclusion of GCSF augmented chromatin condensation and increased expansion from 70- to 120-fold. Inclusion of IL5 induced eosinophilic granules in a third of maturing granulocytes (enlarged example inset). Inclusion of GM-CSF increased expansion to 830-fold, and produced 16% macrophages, while inclusion of M-CSF did not alter expansion, but induced 6% of progenitors to mature as macrophages. Erythropoietin had no impact on neutrophil-committed differentiation. Therefore, SCF Hoxb8-ER progenitors are similar to normal granulocyte-macrophage progenitors (GMP), which retain the ability to differentiate into eosinophils, as well as neutrophils and macrophages. Hoxb8-ER progenitors execute neutrophil differentiation as a default program in SCF alone.

Macrophages produced by maturation of Hoxb8-ER GM-CSF progenitors exhibit normal inflammatory responses. The genetic inflammation response of Hoxb8-ER macrophages was evaluated in response to lipopolysaccharide (LPS), an activator of toll-like receptor 4 (TLR4) and sBLP, an activator of toll-like receptor 2 (TLR2). LPS activated strong transcription of the genes encoding NF-kappa-B, STAT, Jun, and Egr, as well as over 50 additional genes involved in inflammation (Genes responding greater than 10-fold in FIG. 6 and Table 4), including those encoding coactivators of T cell migration and proliferation (TNF9, IL12, IL23), monocyte chemokines (MCP1, MCP3, MIP1a, RANTES) and pleotropic cytokines (IFN-beta, TNFa, IL6, IL1a, IL1b, LIF).

Hoxb8-ER target progenitors can be immortalized from d13 fetal liver. The most useful application of the conditional immortalization system described above is immortalization of progenitors from genetically-engineered mice—those with transgenic or knockout alleles designed to address questions pertaining to issues of immunologic and inflammatory functions. As a simple proof of concept, TLR-induced transcription of IFN and IL-10 in Traf3−/−myeloid cells was tested by restoring Traf3 expression in Traf3−/− progenitors conditionally immortalized by Hoxb8-ER, and testing CpG-induced production of IFN and IL-10 following 6 days. TRAF3 is essential for induction of type I IFNs and the anti-inflammatory cytokine IL-10, but is dispensable for induction of pro-inflammatory cytokines. TRAF3 is also recruited to the adaptor TRIF and is required for marshalling the protein kinase TBK1/NAK into TIR signaling complexes, thereby explaining its unique role in activation of the IFN response. The Traf3−/− mice exhibit a d15 embryonic lethal phenotype, so characterizing their defective responses and restoration of those responses by expression of Traf3 is particularly challenging using the small numbers of myeloid cells that can be expanded from progenitors in fetal liver.

Figure 7:
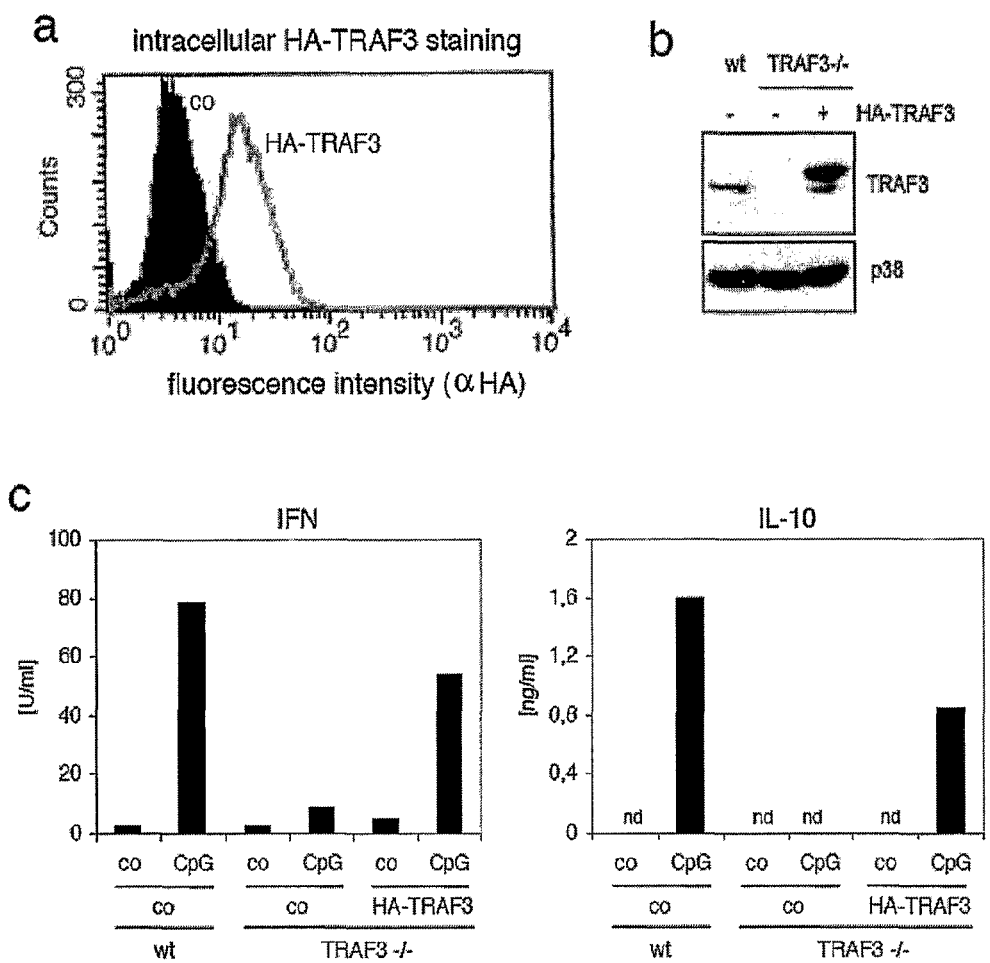
FIGS. 7A-7C demonstrate that reexpression of TRAF3 restores the signaling defect in CpG-induced transactivation of IFN and IL-10 genes in Traf3–/– macrophages produced by HoxB8-ER. Panel A: Wildtype (wt) and Traf3–/– HoxB8-ER-immortalized macrophage progenitor cells (cultured in GM-CSF) were transduced with MSCV-Puro retroviral vectors containing HA-tagged TRAF3 or a control empty vector. Transduced cells were selected with puromycin (2 μg/ml) and TRAF3 expression was measured by intracellular staining with antibodies to the HA-tag. Shown are Traf3–/– cells transduced with the control vector (co) and Traf3–/– cells transduced with the HA-TRAF3 expression construct (HA-TRAF3). For staining, cells were fixed with 2% formaldehyde/PBS and permeabilized with 0.5% saponin. A FITC-labeled antibody was used as secondary antibody to the anti-HA antibody. Cells were analyzed by flow cytometry and are presented as fluorescence intensity vs. cell number. Panel B: Wt and Traf3–/– cells, each transduced with either the control vector or the HA-TRAF3 expression vector, were differentiated for 6 days by removal of estradiol. Lysates of these cells were analyzed by immuno-blotting with antibodies to HA and p38. Panel C: Differentiated Hoxb8-ER macrophages were stimulated with CpG-DNA and analyzed for IFN and IL-10 production by bioassay and ELISA, respectively. nd=not detectable.

Traf3−/− progenitors were immortalized by infection of GM-CSF-dependent progenitors from d13 fetal liver with Hoxb8-ER retrovirus. Immortalized Traf3−/− progenitors grew from the cultures following kinetics identical to those derived from wild-type mice. Traf3−/− HoxB8-ER GM-CSF progenitors were transduced with retroviral vectors containing expression cassettes for HA-tagged TRAF3 and puromycin resistance or a control vector containing the puromycin resistance cassette only. Transduced cells were selected with puromycin (2 µg/ml) and specific expression of TRAF3 was demonstrated by intracellular staining with antibodies to the HA-tag (FIG. 7a). Progenitors transduced with either the control vector or the HA-TRAF3 expression vector, were differentiated for 6 days by withdrawing estrogen. Lysates of these cells were analyzed by immunoblotting with antibodies to HA and p38, and exhibited retention of HA-TRAF3 expression in the differentiated monocytes (FIG. 7b). Differentiated HoxB8-ER monocytes were then stimulated with CpG-DNA and analyzed for IFN and IL-10 production by bioassay and ELISA, respectively. While TRAF3−/− macrophages produced no IFN or IL-10, robust expression was detected in those expressing exogenous HA-TRAF3 (FIG. 7c). Thus, conditional immortalization of knockout progenitors using Hoxb8-ER provides an effective system to study inflammatory signal transduction based on reconstitution of essential protein functions, and can be applied in the circumstance of an embryonic lethal phenotype in order to provide an abundant source of phagocytes for experiments at the cellular or biochemical levels.

Although the invention has been described with reference to the above example, it will be understood that modifications and variations are encompassed within the spirit and scope of the invention. Accordingly, the invention is limited only by the following claims.

We claim:

1. A method of differentiating and immortalizing progenitor cells comprising:
   a) contacting isolated progenitor cells with a fusion protein comprising a HOX oncoprotein and an estrogen receptor binding domain (ERBD), wherein the ERBD consists of the sequence as set forth in SEQ ID NO: 10, wherein said isolated progenitor cells are progenitor cells that give rise to subsets of mature blood cells and wherein the contacting comprises infecting the progenitor cells with a vector comprising a nucleic acid sequence which encodes the fusion protein, and wherein the ERBD is fused to the N-terminus of the HOX oncoprotein; and
   b) culturing the progenitor cells of step a) with a combination of one or more multilineage cytokines, a myeloid-specific cytokine, and an estrogen agonist, whereupon culturing, the progenitor cells become immortalized and exhibit commitment to neutrophil, macrophage, and/or dendritic lineage or exhibit multi-lineage blood cell differentiation potential.

2. The method of claim 1, wherein the vector is a retroviral vector.

* * * * *